US012797444B2

(12) United States Patent
Kim et al.

(10) Patent No.: US 12,797,444 B2
(45) Date of Patent: Nov. 17, 2026

(54) METHOD FOR TREATING, OR REDUCING THE LIKELIHOOD OF DEVELOPING, A LUPUS-ASSOCIATED DISEASE BY ADMINISTERING A PHARMACEUTICAL COMPOSITION COMPRISING GLUCAGON/GLP-1/GIP TRIPLE AGONIST OR LONG-ACTING CONJUGATE THEREOF

(71) Applicant: HANMI PHARM. CO., LTD., Hwaseong-si (KR)

(72) Inventors: Eun Jung Kim, Hwaseong-si (KR); Jae Hyuk Choi, Hwaseong-si (KR); Jung Kuk Kim, Hwaseong-si (KR); Jeong A Kim, Hwaseong-si (KR); Euh Lim Oh, Hwaseong-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 635 days.

(21) Appl. No.: 18/031,940

(22) PCT Filed: Oct. 18, 2021

(86) PCT No.: PCT/KR2021/014468

§ 371 (c)(1),
(2) Date: Apr. 14, 2023

(87) PCT Pub. No.: WO2022/080989

PCT Pub. Date: Apr. 21, 2022

(65) Prior Publication Data

US 2023/0381281 A1 Nov. 30, 2023

(30) Foreign Application Priority Data

Oct. 16, 2020 (KR) ........................ 10-2020-0134482

(51) Int. Cl.

| | |
|---|---|
| ***A61K 38/26*** | (2006.01) |
| ***A61K 47/68*** | (2017.01) |
| ***A61P 29/00*** | (2006.01) |
| ***A61P 37/06*** | (2006.01) |

(52) U.S. Cl.

CPC .............. *A61K 38/26* (2013.01); *A61K 47/68* (2017.08); *A61P 29/00* (2018.01); *A61P 37/06* (2018.01)

(58) Field of Classification Search

CPC ........ A61K 38/26; A61K 38/16; A61K 38/22; A61K 47/68; A61K 47/6811; A61P 29/00; A61P 37/06; A61P 37/00

See application file for complete search history.

(56) References Cited

U.S. PATENT DOCUMENTS

| | | | |
|---|---|---|---|
| 10,188,703 | B2 | 1/2019 | Jung et al. |
| 2013/0203659 | A1 | 8/2013 | Miranda et al. |
| 2016/0257729 | A1 | 9/2016 | Just et al. |
| 2018/0311315 | A1 | 11/2018 | Oh et al. |
| 2018/0344814 | A1 | 12/2018 | Wilson |
| 2022/0213164 | A1 | 7/2022 | Oh et al. |

FOREIGN PATENT DOCUMENTS

| | | | |
|---|---|---|---|
| CN | 106604739 | A | 4/2017 |
| JP | 2017-503474 | A | 2/2017 |
| JP | 2019-069942 | A | 5/2019 |
| KR | 10-2017-0080522 | A | 7/2017 |
| WO | 2017/200944 | A1 | 11/2017 |
| WO | 2018/152172 | A1 | 8/2018 |

OTHER PUBLICATIONS

International Search Report for PCT/KR2021/014468 dated Jan. 24, 2022.

Al Badri Marwa R et al: "Effect of glucagon-like peptide-1 receptor agonists in patients with psoriasis", Therapeutic Advances in Endocrinology and Metabolism, Jan. 1, 2014, p. 34-38, XP093211457.

Kim Jung Kuk et al. "HM15211, a novel long-acting GLP-1/GIP/Glucagon triple agonist, exhibits anti-inflammatory and -fibrotic effects in AMLN/TAA induced liver inflammation and fibrosis mice" Jun. 16, 2020, pp. 1-9, XP093211472.

Extended European Search Report dated Oct. 22, 2024 in Application No. 21880635.4.

China Patent Office, Communication issued Sep. 11, 2026 in Application No. 202180070486.4 with English translation.

Miyake et al., "Increased Insulin Resistance and Glucagon Levels in Mild/Inactive Systemic Lupus Erythematosus Patients Despite Normal Glucose Tolerance", Arthritis Care & Research, vol. 70, No. 1, Jan. 2018, pp. 114-124.

Rashad et al., "Serum and expression profiles of glucose-dependent insulinotropic polypeptide in correlation with cardiometabolic risk factors among patients with systemic lupus erythematosus", The Egyptian Journal of Internal Medicine, 2019, 31:754-762, DOI: 10.4103/ejim.ejim_126_19.

*Primary Examiner* — Robert S Landsman

(74) *Attorney, Agent, or Firm* — Sughrue Mion, PLLC

(57) ABSTRACT

Provided is a pharmaceutical composition for preventing or treating lupus-associated disease, including a glucagon/GLP-1/GIP triple agonist, a pharmaceutically acceptable salt thereof, a solvate thereof, or a long-acting conjugate thereof.

20 Claims, 4 Drawing Sheets

Specification includes a Sequence Listing.

SEQUENCE LISTING

```
<160> NUMBER OF SEQ ID NOS: 149

<210> SEQ ID NO 1
<211> LENGTH: 30
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)

<400> SEQUENCE: 1

His Xaa Gln Gly Thr Phe Thr Ser Asp Val Ser Ser Tyr Leu Asp Gly
1               5                   10                  15

Gln Ala Ala Lys Glu Phe Ile Ala Trp Leu Val Lys Gly Cys
            20                  25                  30


<210> SEQ ID NO 2
<211> LENGTH: 30
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
```

<222> LOCATION: (2)..(2)
<223> OTHER INFORMATION: Xaa is aminoisobutyric acid (Aib)

<400> SEQUENCE: 2

His Xaa Gln Gly Thr Phe Thr Ser Asp Val Ser Ser Tyr Leu Asp Gly
1 5 10 15

Gln Ala Gln Lys Glu Phe Ile Ala Trp Leu Val Lys Gly Cys
20 25 30

<210> SEQ ID NO 3
<211> LENGTH: 41
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)

<400> SEQUENCE: 3

His Xaa Gln Gly Thr Phe Thr Ser Asp Val Ser Ser Tyr Leu Leu Gly
1 5 10 15

Gln Ala Ala Lys Gln Phe Ile Ala Trp Leu Val Lys Gly Gly Gly Pro
20 25 30

Ser Ser Gly Ala Pro Pro Pro Ser Cys
35 40

<210> SEQ ID NO 4
<211> LENGTH: 30
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)

<400> SEQUENCE: 4

His Xaa Gln Gly Thr Phe Thr Ser Asp Val Ser Ser Tyr Leu Leu Gly
1 5 10 15

Gln Gln Gln Lys Glu Phe Ile Ala Trp Leu Val Lys Gly Cys
20 25 30

<210> SEQ ID NO 5
<211> LENGTH: 41
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)

<400> SEQUENCE: 5

His Xaa Gln Gly Thr Phe Thr Ser Asp Val Ser Ser Tyr Leu Leu Gly
1 5 10 15

Gln Gln Gln Lys Glu Phe Ile Ala Trp Leu Val Lys Gly Gly Gly Pro
20 25 30

Ser Ser Gly Ala Pro Pro Pro Ser Cys
35 40

<210> SEQ ID NO 6

<211> LENGTH: 30
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)

<400> SEQUENCE: 6

```
His Xaa Gln Gly Thr Phe Thr Ser Asp Val Ser Ser Tyr Leu Asp Gly
1               5                   10                  15

Gln Ala Ala Lys Glu Phe Val Ala Trp Leu Leu Lys Gly Cys
            20                  25                  30
```

<210> SEQ ID NO 7
<211> LENGTH: 30
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)

<400> SEQUENCE: 7

```
His Xaa Gln Gly Thr Phe Thr Ser Asp Val Ser Lys Tyr Leu Asp Gly
1               5                   10                  15

Gln Ala Ala Lys Glu Phe Val Ala Trp Leu Leu Lys Gly Cys
            20                  25                  30
```

<210> SEQ ID NO 8
<211> LENGTH: 30
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)

<400> SEQUENCE: 8

```
His Xaa Gln Gly Thr Phe Thr Ser Asp Val Ser Lys Tyr Leu Asp Gly
1               5                   10                  15

Gln Ala Ala Gln Glu Phe Val Ala Trp Leu Leu Lys Gly Cys
            20                  25                  30
```

<210> SEQ ID NO 9
<211> LENGTH: 30
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)

<400> SEQUENCE: 9

```
His Xaa Gln Gly Thr Phe Thr Ser Asp Val Ser Lys Tyr Leu Asp Gly
1               5                   10                  15

Gln Ala Ala Gln Glu Phe Val Ala Trp Leu Leu Ala Gly Cys
            20                  25                  30
```

<210> SEQ ID NO 10
<211> LENGTH: 41
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)

<400> SEQUENCE: 10

```
His Xaa Gln Gly Thr Phe Thr Ser Asp Val Ser Lys Tyr Leu Asp Gly
1               5                   10                  15

Gln Ala Ala Gln Glu Phe Val Ala Trp Leu Leu Ala Gly Gly Gly Pro
            20                  25                  30

Ser Ser Gly Ala Pro Pro Pro Ser Cys
        35                  40
```

<210> SEQ ID NO 11
<211> LENGTH: 41
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (1)..(1)
<223> OTHER INFORMATION: Xaa is 4-imidazoacetyl (CA)

<400> SEQUENCE: 11

```
Xaa Gly Glu Gly Thr Phe Thr Ser Asp Leu Ser Lys Tyr Leu Asp Ser
1               5                   10                  15

Arg Arg Gln Gln Leu Phe Val Gln Trp Leu Lys Ala Gly Gly Pro Ser
            20                  25                  30

Ser Gly Ala Pro Pro Pro Ser His Gly
        35                  40
```

<210> SEQ ID NO 12
<211> LENGTH: 41
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (1)..(1)
<223> OTHER INFORMATION: Xaa is 4-imidazoacetyl (CA)

<400> SEQUENCE: 12

```
Xaa Gly Glu Gly Thr Phe Ile Ser Asp Leu Ser Lys Tyr Met Asp Glu
1               5                   10                  15

Gln Ala Val Gln Leu Phe Val Glu Trp Leu Met Ala Gly Gly Pro Ser
            20                  25                  30

Ser Gly Ala Pro Pro Pro Ser His Gly
        35                  40
```

<210> SEQ ID NO 13
<211> LENGTH: 41
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (1)..(1)
<223> OTHER INFORMATION: Xaa is 4-imidazoacetyl (CA)

<400> SEQUENCE: 13

Xaa Gly Glu Gly Thr Phe Ile Ser Asp Tyr Ser Ile Gln Leu Asp Glu
1               5                   10                  15

Ile Ala Val Gln Asp Phe Val Glu Trp Leu Leu Ala Gln Lys Pro Ser
            20                  25                  30

Ser Gly Ala Pro Pro Pro Ser His Gly
        35                  40

<210> SEQ ID NO 14
<211> LENGTH: 41
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (1)..(1)
<223> OTHER INFORMATION: Xaa is 4-imidazoacetyl (CA)

<400> SEQUENCE: 14

Xaa Gly Gln Gly Thr Phe Thr Ser Asp Tyr Ser Ile Gln Leu Asp Glu
1               5                   10                  15

Ile Ala Val Arg Asp Phe Val Glu Trp Leu Lys Asn Gly Gly Pro Ser
            20                  25                  30

Ser Gly Ala Pro Pro Pro Ser His Gly
        35                  40

<210> SEQ ID NO 15
<211> LENGTH: 41
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (1)..(1)
<223> OTHER INFORMATION: Xaa is 4-imidazoacetyl (CA)

<400> SEQUENCE: 15

Xaa Gly Gln Gly Thr Phe Thr Ser Asp Leu Ser Lys Gln Met Asp Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser His Gly
        35                  40

<210> SEQ ID NO 16
<211> LENGTH: 41
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (1)..(1)
<223> OTHER INFORMATION: Xaa is 4-imidazoacetyl (CA)

<400> SEQUENCE: 16

Xaa Gly Gln Gly Thr Phe Thr Ser Asp Leu Ser Lys Gln Met Asp Ser
1               5                   10                  15

Glu Ala Gln Gln Leu Phe Ile Glu Trp Leu Lys Asn Gly Gly Pro Ser
            20                  25                  30

Ser Gly Ala Pro Pro Pro Ser His Gly 35 40

<210> SEQ ID NO 17
<211> LENGTH: 41
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (1)..(1)
<223> OTHER INFORMATION: Xaa is 4-imidazoacetyl (CA)

<400> SEQUENCE: 17

```
Xaa Gly Gln Gly Thr Phe Thr Ser Asp Leu Ser Lys Gln Met Asp Glu
1               5                   10                  15

Glu Arg Ala Arg Glu Phe Ile Glu Trp Leu Leu Ala Gln Lys Pro Ser
            20                  25                  30

Ser Gly Ala Pro Pro Pro Ser His Gly
        35                  40
```

<210> SEQ ID NO 18
<211> LENGTH: 41
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (1)..(1)
<223> OTHER INFORMATION: Xaa is 4-imidazoacetyl (CA)

<400> SEQUENCE: 18

```
Xaa Gly Gln Gly Thr Phe Thr Ser Asp Leu Ser Lys Gln Met Asp Ser
1               5                   10                  15

Glu Arg Ala Arg Glu Phe Ile Glu Trp Leu Lys Asn Thr Gly Pro Ser
            20                  25                  30

Ser Gly Ala Pro Pro Pro Ser His Gly
        35                  40
```

<210> SEQ ID NO 19
<211> LENGTH: 41
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (1)..(1)
<223> OTHER INFORMATION: Xaa is 4-imidazoacetyl (CA)

<400> SEQUENCE: 19

```
Xaa Gly Gln Gly Thr Phe Thr Ser Asp Leu Ser Ile Gln Tyr Asp Ser
1               5                   10                  15

Glu His Gln Arg Asp Phe Ile Glu Trp Leu Lys Asp Thr Gly Pro Ser
            20                  25                  30

Ser Gly Ala Pro Pro Pro Ser His Gly
        35                  40
```

<210> SEQ ID NO 20
<211> LENGTH: 41
<212> TYPE: PRT
<213> ORGANISM: Artificial
<220> FEATURE:
<223> OTHER INFORMATION: Triple agonist
<220> FEATURE:

<221> NAME/KEY: MISC_FEATURE
<222> LOCATION: (1)..(1)
<223> OTHER INFORMATION: Xaa is 4-imidazoacetyl (CA)

<400> SEQUENCE: 20

```
Xaa Gly Gln Gly Thr Phe Thr Ser Asp Leu Ser Ile Gln Tyr Glu Glu
1               5                   10                  15

Glu Ala Gln Gln Asp Phe Val Glu Trp Leu Lys Asp Thr Gly Pro Ser
            20                  25                  30

Ser Gly Ala Pro Pro Pro Ser His Gly
        35                  40
```

<210> SEQ ID NO 21
<211> LENGTH: 39
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 21

```
Tyr Xaa Gln Gly Thr Phe Thr Ser Asp Tyr Ser Lys Tyr Leu Asp Glu
1               5                   10                  15

Cys Arg Ala Lys Glu Phe Val Gln Trp Leu Leu Asp His His Pro Ser
            20                  25                  30

Ser Gly Gln Pro Pro Pro Ser
        35
```

<210> SEQ ID NO 22
<211> LENGTH: 39
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 22

```
Tyr Xaa Gln Gly Thr Phe Thr Ser Asp Tyr Ser Lys Cys Leu Asp Glu
1               5                   10                  15

Lys Arg Ala Lys Glu Phe Val Gln Trp Leu Leu Asp His His Pro Ser
            20                  25                  30

Ser Gly Gln Pro Pro Pro Ser
        35
```

<210> SEQ ID NO 23
<211> LENGTH: 41
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)

<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 23

```
Tyr Xaa Gln Gly Thr Phe Thr Ser Asp Tyr Ser Lys Tyr Leu Asp Glu
1               5                   10                  15

Cys Arg Ala Lys Glu Phe Val Gln Trp Leu Leu Ala Gln Lys Gly Lys
            20                  25                  30

Lys Asn Asp Trp Lys His Asn Ile Thr
        35                  40
```

<210> SEQ ID NO 24
<211> LENGTH: 39
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 24

```
Tyr Xaa Gln Gly Thr Phe Thr Ser Asp Tyr Ser Lys Tyr Leu Asp Glu
1               5                   10                  15

Cys Arg Ala Lys Glu Phe Val Gln Trp Leu Lys Asn Gly Gly Pro Ser
            20                  25                  30

Ser Gly Ala Pro Pro Pro Ser
        35
```

<210> SEQ ID NO 25
<211> LENGTH: 39
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)

<400> SEQUENCE: 25

```
His Xaa Gln Gly Thr Phe Thr Ser Asp Cys Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
        35
```

<210> SEQ ID NO 26
<211> LENGTH: 39
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)

-continued

<400> SEQUENCE: 26

His Xaa Gln Gly Thr Phe Thr Ser Asp Cys Ser Lys Tyr Leu Asp Ser
1 5 10 15

Arg Ala Ala Gln Asp Phe Val Gln Trp Leu Leu Asp Gly Gly Pro Ser
20 25 30

Ser Gly Ala Pro Pro Pro Ser
35

<210> SEQ ID NO 27
<211> LENGTH: 40
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)

<400> SEQUENCE: 27

His Xaa Gln Gly Thr Phe Thr Ser Asp Tyr Ser Lys Tyr Leu Asp Glu
1 5 10 15

Arg Ala Cys Gln Asp Phe Val Gln Trp Leu Leu Asp Gln Gly Gly Pro
20 25 30

Ser Ser Gly Ala Pro Pro Pro Ser
35 40

<210> SEQ ID NO 28
<211> LENGTH: 41
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)

<400> SEQUENCE: 28

His Xaa Gln Gly Thr Phe Thr Ser Asp Tyr Ser Lys Tyr Leu Asp Glu
1 5 10 15

Lys Arg Ala Gln Glu Phe Val Cys Trp Leu Leu Ala Gln Lys Gly Lys
20 25 30

Lys Asn Asp Trp Lys His Asn Ile Thr
35 40

<210> SEQ ID NO 29
<211> LENGTH: 30
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 29

His Xaa Gln Gly Thr Phe Thr Ser Asp Tyr Ser Lys Tyr Leu Asp Glu
1 5 10 15

Lys Ala Ala Lys Glu Phe Val Gln Trp Leu Leu Asn Thr Cys 20 25 30

<210> SEQ ID NO 30
<211> LENGTH: 30
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 30

His Xaa Gln Gly Thr Phe Thr Ser Asp Tyr Ser Lys Tyr Leu Asp Glu
1 5 10 15

Lys Ala Gln Lys Glu Phe Val Gln Trp Leu Leu Asp Thr Cys
20 25 30

<210> SEQ ID NO 31
<211> LENGTH: 29
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 31

His Xaa Gln Gly Thr Phe Thr Ser Asp Tyr Ser Lys Tyr Leu Asp Glu
1 5 10 15

Lys Ala Cys Lys Glu Phe Val Gln Trp Leu Leu Ala Gln
20 25

<210> SEQ ID NO 32
<211> LENGTH: 39
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 32

His Xaa Gln Gly Thr Phe Thr Ser Asp Tyr Ser Lys Tyr Leu Asp Glu
1 5 10 15

Lys Ala Cys Lys Asp Phe Val Gln Trp Leu Leu Asp Gly Gly Pro Ser
20 25 30

Ser Gly Ala Pro Pro Pro Ser
35

<210> SEQ ID NO 33

-continued

```
<211> LENGTH: 31
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 33

His Xaa Gln Gly Thr Phe Thr Ser Asp Tyr Ser Ile Ala Met Asp Glu
1               5                   10                  15

Ile His Gln Lys Asp Phe Val Asn Trp Leu Leu Ala Gln Lys Cys
            20                  25                  30


<210> SEQ ID NO 34
<211> LENGTH: 31
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 34

His Xaa Gln Gly Thr Phe Thr Ser Asp Tyr Ser Lys Tyr Leu Asp Glu
1               5                   10                  15

Lys Arg Gln Lys Glu Phe Val Asn Trp Leu Leu Ala Gln Lys Cys
            20                  25                  30


<210> SEQ ID NO 35
<211> LENGTH: 31
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 35

His Xaa Gln Gly Thr Phe Thr Ser Asp Tyr Ser Ile Ala Met Asp Glu
1               5                   10                  15

Ile His Gln Lys Asp Phe Val Asn Trp Leu Leu Asn Thr Lys Cys
            20                  25                  30


<210> SEQ ID NO 36
<211> LENGTH: 40
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
```

<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 36

```
His Xaa Gln Gly Thr Phe Thr Ser Asp Tyr Ser Lys Tyr Leu Cys Glu
1               5                   10                  15

Lys Arg Gln Lys Glu Phe Val Gln Trp Leu Leu Asn Gly Gly Pro Ser
            20                  25                  30

Ser Gly Ala Pro Pro Pro Ser Gly
        35                  40
```

<210> SEQ ID NO 37
<211> LENGTH: 40
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 37

```
His Xaa Gln Gly Thr Phe Thr Ser Asp Tyr Ser Lys Tyr Leu Asp Glu
1               5                   10                  15

Cys Arg Gln Lys Glu Phe Val Gln Trp Leu Leu Asn Gly Gly Pro Ser
            20                  25                  30

Ser Gly Ala Pro Pro Pro Ser Gly
        35                  40
```

<210> SEQ ID NO 38
<211> LENGTH: 40
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (1)..(1)
<223> OTHER INFORMATION: Xaa is 4-imidazoacetyl (CA)
<220> FEATURE:
<221> NAME/KEY: MISC_FEATURE
<222> LOCATION: (2)..(2)
<223> OTHER INFORMATION: Xaa is aminoisobutyric acid (Aib)

<400> SEQUENCE: 38

```
Xaa Xaa Gln Gly Thr Phe Thr Ser Asp Lys Ser Ser Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Ser
        35                  40
```

<210> SEQ ID NO 39
<211> LENGTH: 40
<212> TYPE: PRT
<213> ORGANISM: Artificial
<220> FEATURE:
<223> OTHER INFORMATION: Triple agonist -continued
<220> FEATURE:
<221> NAME/KEY: MISC_FEATURE
<222> LOCATION: (2)..(2)
<223> OTHER INFORMATION: Xaa is aminoisobutyric acid (Aib)

<400> SEQUENCE: 39

His Xaa Gln Gly Thr Phe Thr Ser Asp Tyr Ser Lys Tyr Leu Asp Gly
1 5 10 15

Gln His Ala Gln Cys Phe Val Ala Trp Leu Leu Ala Gly Gly Gly Pro
20 25 30

Ser Ser Gly Ala Pro Pro Pro Ser
35 40

<210> SEQ ID NO 40
<211> LENGTH: 39
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)

<400> SEQUENCE: 40

His Xaa Gln Gly Thr Phe Thr Ser Asp Lys Ser Lys Tyr Leu Asp Glu
1 5 10 15

Arg Ala Cys Gln Asp Phe Val Gln Trp Leu Leu Asp Gly Gly Pro Ser
20 25 30

Ser Gly Ala Pro Pro Pro Ser
35

<210> SEQ ID NO 41
<211> LENGTH: 39
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)

<400> SEQUENCE: 41

His Xaa Gln Gly Thr Phe Thr Ser Asp Lys Ser Lys Tyr Leu Asp Glu
1 5 10 15

Cys Ala Ala Gln Asp Phe Val Gln Trp Leu Leu Asp Gly Gly Pro Ser
20 25 30

Ser Gly Ala Pro Pro Pro Ser
35

<210> SEQ ID NO 42
<211> LENGTH: 40
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 42

Tyr Xaa Gln Gly Thr Phe Thr Ser Asp Tyr Ser Lys Tyr Leu Asp Glu
1 5 10 15

Lys Arg Ala Lys Glu Phe Val Gln Trp Leu Leu Asp His His Pro Ser
20 25 30

Ser Gly Gln Pro Pro Pro Ser Cys
35 40

<210> SEQ ID NO 43
<211> LENGTH: 39
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 43

Tyr Xaa Gln Gly Thr Phe Thr Ser Asp Tyr Ser Lys Tyr Leu Asp Glu
1 5 10 15

Lys Arg Ala Lys Glu Phe Val Gln Trp Leu Leu Asp His His Cys Ser
20 25 30

Ser Gly Gln Pro Pro Pro Ser
35

<210> SEQ ID NO 44
<211> LENGTH: 39
<212> TYPE: PRT
<213> ORGANISM: Artificial
<220> FEATURE:
<223> OTHER INFORMATION: Triple agonist

<400> SEQUENCE: 44

His Gly Gln Gly Thr Phe Thr Ser Asp Cys Ser Lys Gln Leu Asp Gly
1 5 10 15

Gln Ala Ala Gln Glu Phe Val Ala Trp Leu Leu Ala Gly Gly Pro Ser
20 25 30

Ser Gly Ala Pro Pro Pro Ser
35

<210> SEQ ID NO 45
<211> LENGTH: 39
<212> TYPE: PRT
<213> ORGANISM: Artificial
<220> FEATURE:
<223> OTHER INFORMATION: Triple agonist

<400> SEQUENCE: 45

His Gly Gln Gly Thr Phe Thr Ser Asp Cys Ser Lys Tyr Met Asp Gly
1 5 10 15

Gln Ala Ala Gln Asp Phe Val Ala Trp Leu Leu Ala Gly Gly Pro Ser
20 25 30

Ser Gly Ala Pro Pro Pro Ser
35

<210> SEQ ID NO 46
<211> LENGTH: 39
<212> TYPE: PRT

<213> ORGANISM: Artificial
<220> FEATURE:
<223> OTHER INFORMATION: Triple agonist

<400> SEQUENCE: 46

His Gly Gln Gly Thr Phe Thr Ser Asp Cys Ser Lys Tyr Leu Asp Glu
1 5 10 15

Gln His Ala Gln Glu Phe Val Ala Trp Leu Leu Ala Gly Gly Pro Ser
20 25 30

Ser Gly Ala Pro Pro Pro Ser
35

<210> SEQ ID NO 47
<211> LENGTH: 39
<212> TYPE: PRT
<213> ORGANISM: Artificial
<220> FEATURE:
<223> OTHER INFORMATION: Triple agonist

<400> SEQUENCE: 47

His Gly Gln Gly Thr Phe Thr Ser Asp Cys Ser Lys Tyr Leu Asp Gly
1 5 10 15

Gln Arg Ala Gln Glu Phe Val Ala Trp Leu Leu Ala Gly Gly Pro Ser
20 25 30

Ser Gly Ala Pro Pro Pro Ser
35

<210> SEQ ID NO 48
<211> LENGTH: 39
<212> TYPE: PRT
<213> ORGANISM: Artificial
<220> FEATURE:
<223> OTHER INFORMATION: Triple agonist

<400> SEQUENCE: 48

His Gly Gln Gly Thr Phe Thr Ser Asp Cys Ser Lys Tyr Leu Asp Gly
1 5 10 15

Gln Arg Ala Gln Asp Phe Val Asn Trp Leu Leu Ala Gly Gly Pro Ser
20 25 30

Ser Gly Ala Pro Pro Pro Ser
35

<210> SEQ ID NO 49
<211> LENGTH: 30
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (1)..(1)
<223> OTHER INFORMATION: Xaa is 4-imidazoacetyl (CA)
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 49

Xaa Xaa Gln Gly Thr Phe Thr Ser Asp Tyr Ser Ile Cys Met Asp Glu
1 5 10 15

Ile His Gln Lys Asp Phe Val Asn Trp Leu Leu Asn Thr Lys 20 25 30

<210> SEQ ID NO 50
<211> LENGTH: 40
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 50

His Xaa Gln Gly Thr Phe Thr Ser Asp Tyr Ser Lys Tyr Leu Asp Glu
1 5 10 15

Lys Arg Ala Lys Glu Phe Val Gln Trp Leu Leu Asp His His Pro Ser
20 25 30

Ser Gly Gln Pro Pro Pro Ser Cys
35 40

<210> SEQ ID NO 51
<211> LENGTH: 30
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 51

His Xaa Gln Gly Thr Phe Thr Ser Asp Tyr Ser Lys Tyr Leu Asp Glu
1 5 10 15

Lys Arg Gln Lys Glu Phe Val Gln Trp Leu Leu Asn Thr Cys
20 25 30

<210> SEQ ID NO 52
<211> LENGTH: 30
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 52

His Xaa Gln Gly Thr Phe Thr Ser Asp Tyr Ser Lys Tyr Leu Asp Glu
1 5 10 15

Lys Arg Gln Lys Glu Phe Val Gln Trp Leu Leu Asp Thr Cys
20 25 30

<210> SEQ ID NO 53

-continued

<211> LENGTH: 30
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 53

```
His Xaa Glu Gly Thr Phe Thr Ser Asp Tyr Ser Ile Ala Met Asp Glu
1               5                   10                  15

Ile His Gln Lys Asp Phe Val Asn Trp Leu Leu Ala Gln Cys
            20                  25                  30
```

<210> SEQ ID NO 54
<211> LENGTH: 30
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 54

```
His Xaa Glu Gly Thr Phe Thr Ser Asp Tyr Ser Ile Ala Met Asp Glu
1               5                   10                  15

Ile His Gln Lys Asp Phe Val Asp Trp Leu Leu Ala Glu Cys
            20                  25                  30
```

<210> SEQ ID NO 55
<211> LENGTH: 30
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 55

```
His Xaa Gln Gly Thr Phe Thr Ser Asp Tyr Ser Ile Ala Met Asp Glu
1               5                   10                  15

Ile His Gln Lys Asp Phe Val Asn Trp Leu Leu Ala Gln Cys
            20                  25                  30
```

<210> SEQ ID NO 56
<211> LENGTH: 30
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 56

```
His Xaa Gln Gly Thr Phe Thr Ser Asp Tyr Ser Lys Tyr Leu Asp Glu
1               5                   10                  15

Lys Arg Gln Lys Glu Phe Val Asn Trp Leu Leu Ala Gln Cys
            20                  25                  30
```

<210> SEQ ID NO 57
<211> LENGTH: 30
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 57

```
His Xaa Gln Gly Thr Phe Thr Ser Asp Tyr Ser Ile Ala Met Asp Glu
1               5                   10                  15

Ile His Gln Lys Asp Phe Val Asn Trp Leu Leu Asn Thr Cys
            20                  25                  30
```

<210> SEQ ID NO 58
<211> LENGTH: 31
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 58

```
His Xaa Gln Gly Thr Phe Thr Ser Asp Tyr Ser Lys Tyr Leu Asp Glu
1               5                   10                  15

Lys Arg Gln Lys Glu Phe Val Gln Trp Leu Leu Asn Thr Lys Cys
            20                  25                  30
```

<210> SEQ ID NO 59
<211> LENGTH: 30
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (1)..(1)
<223> OTHER INFORMATION: Xaa is 4-imidazoacetyl (CA)
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:

<221> NAME/KEY: MISC_FEATURE
<222> LOCATION: (16)..(20)
<223> OTHER INFORMATION: amino acids at positions 16 and 20 form a ring

<400> SEQUENCE: 59

```
Xaa Xaa Gln Gly Thr Phe Thr Ser Asp Tyr Ser Ile Cys Met Asp Glu
1               5                   10                  15

Lys His Gln Lys Asp Phe Val Asn Trp Leu Leu Asn Thr Lys
            20                  25                  30
```

<210> SEQ ID NO 60
<211> LENGTH: 30
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (1)..(1)
<223> OTHER INFORMATION: Xaa is 4-imidazoacetyl (CA)
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 60

```
Xaa Xaa Gln Gly Thr Phe Thr Ser Asp Tyr Ser Ile Ala Met Asp Glu
1               5                   10                  15

Lys His Cys Lys Asp Phe Val Asn Trp Leu Leu Asn Thr Lys
            20                  25                  30
```

<210> SEQ ID NO 61
<211> LENGTH: 30
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (1)..(1)
<223> OTHER INFORMATION: Xaa is 4-imidazoacetyl (CA)
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 61

```
Xaa Xaa Gln Gly Thr Phe Thr Ser Asp Tyr Ser Ile Ala Met Asp Glu
1               5                   10                  15

Ile Ala Cys Lys Asp Phe Val Asn Trp Leu Leu Asn Thr Lys
            20                  25                  30
```

<210> SEQ ID NO 62
<211> LENGTH: 39
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (1)..(1)
<223> OTHER INFORMATION: Xaa is 4-imidazoacetyl (CA)

-continued

<220> FEATURE:
<221> NAME/KEY: MISC_FEATURE
<222> LOCATION: (2)..(2)
<223> OTHER INFORMATION: Xaa is aminoisobutyric acid (Aib)

<400> SEQUENCE: 62

Xaa Xaa Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
        35

<210> SEQ ID NO 63
<211> LENGTH: 39
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (1)..(1)
<223> OTHER INFORMATION: Xaa is 4-imidazoacetyl (CA)
<220> FEATURE:
<221> NAME/KEY: MISC_FEATURE
<222> LOCATION: (2)..(2)
<223> OTHER INFORMATION: Xaa is aminoisobutyric acid (Aib)

<400> SEQUENCE: 63

Xaa Xaa Gln Gly Thr Phe Thr Ser Asp Cys Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
        35

<210> SEQ ID NO 64
<211> LENGTH: 39
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 64

Tyr Xaa Gln Gly Thr Phe Thr Ser Asp Tyr Ser Lys Tyr Leu Asp Glu
1               5                   10                  15

Cys Ala Ala Lys Glu Phe Val Gln Trp Leu Leu Asp His His Pro Ser
            20                  25                  30

Ser Gly Gln Pro Pro Pro Ser
        35

<210> SEQ ID NO 65
<211> LENGTH: 39
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 65

His Xaa Gln Gly Thr Phe Thr Ser Asp Tyr Ser Lys Cys Leu Asp Glu
1               5                   10                  15

Lys Arg Ala Lys Glu Phe Val Gln Trp Leu Leu Asp His His Pro Ser
            20                  25                  30

Ser Gly Gln Pro Pro Pro Ser
        35

<210> SEQ ID NO 66
<211> LENGTH: 39
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 66

Tyr Xaa Gln Gly Thr Phe Thr Ser Asp Tyr Ser Lys Tyr Leu Asp Glu
1               5                   10                  15

Cys Arg Ala Lys Asp Phe Val Gln Trp Leu Leu Asp His His Pro Ser
            20                  25                  30

Ser Gly Gln Pro Pro Pro Ser
        35

<210> SEQ ID NO 67
<211> LENGTH: 39
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 67

Tyr Xaa Gln Gly Thr Phe Thr Ser Asp Tyr Ser Lys Tyr Leu Asp Glu
1               5                   10                  15

Cys Ala Ala Lys Asp Phe Val Gln Trp Leu Leu Asp His His Pro Ser
            20                  25                  30

Ser Gly Gln Pro Pro Pro Ser
        35

<210> SEQ ID NO 68
<211> LENGTH: 39
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 68

```
Tyr Xaa Gln Gly Thr Phe Thr Ser Asp Tyr Ser Lys Cys Leu Asp Glu
1               5                   10                  15

Lys Ala Ala Lys Glu Phe Val Gln Trp Leu Leu Asp His His Pro Ser
            20                  25                  30

Ser Gly Gln Pro Pro Pro Ser
        35
```

<210> SEQ ID NO 69
<211> LENGTH: 39
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 69

```
Tyr Xaa Gln Gly Thr Phe Thr Ser Asp Tyr Ser Lys Cys Leu Asp Glu
1               5                   10                  15

Arg Ala Ala Lys Glu Phe Val Gln Trp Leu Leu Asp His His Pro Ser
            20                  25                  30

Ser Gly Gln Pro Pro Pro Ser
        35
```

<210> SEQ ID NO 70
<211> LENGTH: 39
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 70

```
Tyr Xaa Gln Gly Thr Phe Thr Ser Asp Tyr Ser Lys Cys Leu Asp Glu
1               5                   10                  15

Lys Arg Ala Lys Asp Phe Val Gln Trp Leu Leu Asp His His Pro Ser
            20                  25                  30

Ser Gly Gln Pro Pro Pro Ser
        35
```

<210> SEQ ID NO 71
<211> LENGTH: 39
<212> TYPE: PRT
<213> ORGANISM: Artificial

<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 71

```
Tyr Xaa Gln Gly Thr Phe Thr Ser Asp Tyr Ser Lys Tyr Leu Asp Glu
1               5                   10                  15

Arg Ala Cys Lys Asp Phe Val Gln Trp Leu Leu Asp His His Pro Ser
            20                  25                  30

Ser Gly Gln Pro Pro Pro Ser
        35
```

<210> SEQ ID NO 72
<211> LENGTH: 39
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 72

```
Tyr Xaa Gln Gly Thr Phe Thr Ser Asp Cys Ser Lys Tyr Leu Asp Glu
1               5                   10                  15

Arg Ala Ala Lys Asp Phe Val Gln Trp Leu Leu Asp His His Pro Ser
            20                  25                  30

Ser Gly Gln Pro Pro Pro Ser
        35
```

<210> SEQ ID NO 73
<211> LENGTH: 39
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (1)..(1)
<223> OTHER INFORMATION: Xaa is 4-imidazoacetyl (CA)
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 73

```
Xaa Xaa Gln Gly Thr Phe Thr Ser Asp Tyr Ser Lys Tyr Leu Asp Glu
1               5                   10                  15

Cys Arg Ala Lys Glu Phe Val Gln Trp Leu Leu Asp His His Pro Ser
            20                  25                  30

Ser Gly Gln Pro Pro Pro Ser
        35
```

<210> SEQ ID NO 74
<211> LENGTH: 39
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (1)..(1)
<223> OTHER INFORMATION: Xaa is 4-imidazoacetyl (CA)
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 74

```
Xaa Xaa Gln Gly Thr Phe Thr Ser Asp Tyr Ser Lys Cys Leu Asp Glu
1               5                   10                  15

Lys Arg Ala Lys Glu Phe Val Gln Trp Leu Leu Asp His His Pro Ser
            20                  25                  30

Ser Gly Gln Pro Pro Pro Ser
        35
```

<210> SEQ ID NO 75
<211> LENGTH: 40
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 75

```
Tyr Xaa Gln Gly Thr Phe Thr Ser Asp Tyr Ser Lys Tyr Leu Asp Glu
1               5                   10                  15

Lys Ala Ala Lys Glu Phe Val Gln Trp Leu Leu Asp His His Pro Ser
            20                  25                  30

Ser Gly Gln Pro Pro Pro Ser Cys
        35                  40
```

<210> SEQ ID NO 76
<211> LENGTH: 40
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 76

```
Tyr Xaa Gln Gly Thr Phe Thr Ser Asp Tyr Ser Lys Tyr Leu Asp Glu
1               5                   10                  15
```

Lys Arg Ala Lys Asp Phe Val Gln Trp Leu Leu Asp His His Pro Ser
20 25 30

Ser Gly Gln Pro Pro Pro Ser Cys
35 40

<210> SEQ ID NO 77
<211> LENGTH: 40
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 77

Tyr Xaa Gln Gly Thr Phe Thr Ser Asp Tyr Ser Lys Tyr Leu Asp Glu
1 5 10 15

Lys Ala Ala Lys Asp Phe Val Gln Trp Leu Leu Asp His His Pro Ser
20 25 30

Ser Gly Gln Pro Pro Pro Ser Cys
35 40

<210> SEQ ID NO 78
<211> LENGTH: 31
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 78

His Xaa Gln Gly Thr Phe Thr Ser Asp Tyr Ser Lys Tyr Leu Asp Glu
1 5 10 15

Lys Arg Gln Lys Glu Phe Val Gln Trp Leu Leu Asp Thr Lys Cys
20 25 30

<210> SEQ ID NO 79
<211> LENGTH: 31
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 79

His Xaa Glu Gly Thr Phe Thr Ser Asp Tyr Ser Ile Ala Met Asp Glu
1 5 10 15

-continued

```
Ile His Gln Lys Asp Phe Val Asn Trp Leu Leu Ala Gln Lys Cys
            20                  25                  30


<210> SEQ ID NO 80
<211> LENGTH: 31
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 80

His Xaa Glu Gly Thr Phe Thr Ser Asp Tyr Ser Ile Ala Met Asp Glu
1               5                   10                  15

Ile His Gln Lys Asp Phe Val Asp Trp Leu Leu Ala Glu Lys Cys
            20                  25                  30


<210> SEQ ID NO 81
<211> LENGTH: 30
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (1)..(1)
<223> OTHER INFORMATION: Xaa is 4-imidazoacetyl (CA)
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 81

Xaa Xaa Gln Gly Thr Phe Thr Ser Asp Tyr Ser Lys Tyr Leu Asp Glu
1               5                   10                  15

Lys Arg Gln Lys Glu Phe Val Gln Trp Leu Leu Asn Thr Cys
            20                  25                  30


<210> SEQ ID NO 82
<211> LENGTH: 30
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (1)..(1)
<223> OTHER INFORMATION: Xaa is 4-imidazoacetyl (CA)
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 82

Xaa Xaa Gln Gly Thr Phe Thr Ser Asp Tyr Ser Lys Tyr Leu Asp Glu
1               5                   10                  15
```

```
Lys Arg Gln Lys Glu Phe Val Gln Trp Leu Leu Asp Thr Cys
            20                  25                  30


<210> SEQ ID NO 83
<211> LENGTH: 30
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (1)..(1)
<223> OTHER INFORMATION: Xaa is 4-imidazoacetyl (CA)
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 83

Xaa Xaa Glu Gly Thr Phe Thr Ser Asp Tyr Ser Ile Ala Met Asp Glu
1               5                   10                  15

Ile His Gln Lys Asp Phe Val Asn Trp Leu Leu Ala Gln Cys
            20                  25                  30


<210> SEQ ID NO 84
<211> LENGTH: 30
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (1)..(1)
<223> OTHER INFORMATION: Xaa is 4-imidazoacetyl (CA)
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 84

Xaa Xaa Glu Gly Thr Phe Thr Ser Asp Tyr Ser Ile Ala Met Asp Glu
1               5                   10                  15

Ile His Gln Lys Asp Phe Val Asp Trp Leu Leu Ala Glu Cys
            20                  25                  30


<210> SEQ ID NO 85
<211> LENGTH: 30
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (1)..(1)
<223> OTHER INFORMATION: Xaa is 4-imidazoacetyl (CA)
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring
```

-continued

<400> SEQUENCE: 85

```
Xaa Xaa Gln Gly Thr Phe Thr Ser Asp Tyr Ser Ile Ala Met Asp Glu
1               5                   10                  15

Ile His Gln Lys Asp Phe Val Asn Trp Leu Leu Ala Gln Cys
            20                  25                  30
```

<210> SEQ ID NO 86
<211> LENGTH: 30
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (1)..(1)
<223> OTHER INFORMATION: Xaa is 4-imidazoacetyl (CA)
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 86

```
Xaa Xaa Gln Gly Thr Phe Thr Ser Asp Tyr Ser Lys Tyr Leu Asp Glu
1               5                   10                  15

Lys Arg Gln Lys Glu Phe Val Asn Trp Leu Leu Ala Gln Cys
            20                  25                  30
```

<210> SEQ ID NO 87
<211> LENGTH: 30
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (1)..(1)
<223> OTHER INFORMATION: Xaa is 4-imidazoacetyl (CA)
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 87

```
Xaa Xaa Gln Gly Thr Phe Thr Ser Asp Tyr Ser Ile Ala Met Asp Glu
1               5                   10                  15

Ile His Gln Lys Asp Phe Val Asn Trp Leu Leu Asn Thr Cys
            20                  25                  30
```

<210> SEQ ID NO 88
<211> LENGTH: 31
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (1)..(1)
<223> OTHER INFORMATION: Xaa is 4-imidazoacetyl (CA)
<220> FEATURE:
<221> NAME/KEY: MISC_FEATURE
<222> LOCATION: (2)..(2)

-continued

<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 88

Xaa Xaa Gln Gly Thr Phe Thr Ser Asp Tyr Ser Lys Tyr Leu Asp Glu
1 5 10 15

Lys Arg Gln Lys Glu Phe Val Gln Trp Leu Leu Asn Thr Lys Cys
20 25 30

<210> SEQ ID NO 89
<211> LENGTH: 31
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (1)..(1)
<223> OTHER INFORMATION: Xaa is 4-imidazoacetyl (CA)
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 89

Xaa Xaa Gln Gly Thr Phe Thr Ser Asp Tyr Ser Lys Tyr Leu Asp Glu
1 5 10 15

Lys Arg Gln Lys Glu Phe Val Gln Trp Leu Leu Asp Thr Lys Cys
20 25 30

<210> SEQ ID NO 90
<211> LENGTH: 31
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (1)..(1)
<223> OTHER INFORMATION: Xaa is 4-imidazoacetyl (CA)
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 90

Xaa Xaa Glu Gly Thr Phe Thr Ser Asp Tyr Ser Ile Ala Met Asp Glu
1 5 10 15

Ile His Gln Lys Asp Phe Val Asn Trp Leu Leu Ala Gln Lys Cys
20 25 30

<210> SEQ ID NO 91
<211> LENGTH: 31
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (1)..(1)
<223> OTHER INFORMATION: Xaa is 4-imidazoacetyl (CA)
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 91

```
Xaa Xaa Glu Gly Thr Phe Thr Ser Asp Tyr Ser Ile Ala Met Asp Glu
1               5                   10                  15

Ile His Gln Lys Asp Phe Val Asp Trp Leu Leu Ala Glu Lys Cys
            20                  25                  30
```

<210> SEQ ID NO 92
<211> LENGTH: 31
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (1)..(1)
<223> OTHER INFORMATION: Xaa is 4-imidazoacetyl (CA)
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 92

```
Xaa Xaa Gln Gly Thr Phe Thr Ser Asp Tyr Ser Ile Ala Met Asp Glu
1               5                   10                  15

Ile His Gln Lys Asp Phe Val Asn Trp Leu Leu Ala Gln Lys Cys
            20                  25                  30
```

<210> SEQ ID NO 93
<211> LENGTH: 31
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (1)..(1)
<223> OTHER INFORMATION: Xaa is 4-imidazoacetyl (CA)
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 93

```
Xaa Xaa Gln Gly Thr Phe Thr Ser Asp Tyr Ser Lys Tyr Leu Asp Glu
1               5                   10                  15

Lys Arg Gln Lys Glu Phe Val Asn Trp Leu Leu Ala Gln Lys Cys
            20                  25                  30
```

<210> SEQ ID NO 94
<211> LENGTH: 31
<212> TYPE: PRT

-continued

<213> ORGANISM: Artificial
<220> FEATURE:
<223> OTHER INFORMATION: Triple agonist
<220> FEATURE:
<221> NAME/KEY: MISC_FEATURE
<222> LOCATION: (1)..(1)
<223> OTHER INFORMATION: Xaa is 4-imidazoacetyl (CA)
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 94

```
Xaa Xaa Gln Gly Thr Phe Thr Ser Asp Tyr Ser Ile Ala Met Asp Glu
1               5                   10                  15

Ile His Gln Lys Asp Phe Val Asn Trp Leu Leu Asn Thr Lys Cys
            20                  25                  30
```

<210> SEQ ID NO 95
<211> LENGTH: 39
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 95

```
Tyr Xaa Gln Gly Thr Phe Thr Ser Asp Tyr Ser Lys Tyr Leu Asp Glu
1               5                   10                  15

Lys Arg Ala Lys Glu Phe Val Gln Trp Leu Leu Cys His His Pro Ser
            20                  25                  30

Ser Gly Gln Pro Pro Pro Ser
        35
```

<210> SEQ ID NO 96
<211> LENGTH: 39
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 96

```
Tyr Xaa Gln Gly Thr Phe Thr Ser Asp Tyr Ser Lys Tyr Leu Asp Glu
1               5                   10                  15

Lys Arg Ala Lys Glu Phe Val Gln Trp Leu Leu Asp His Cys Pro Ser
            20                  25                  30

Ser Gly Gln Pro Pro Pro Ser
        35
```

<210> SEQ ID NO 97
<211> LENGTH: 39
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 97

```
Tyr Xaa Gln Gly Thr Phe Thr Ser Asp Tyr Ser Lys Tyr Leu Asp Glu
1               5                   10                  15

Lys Arg Ala Lys Glu Phe Val Gln Trp Leu Leu Asp Cys His Pro Ser
            20                  25                  30

Ser Gly Gln Pro Pro Pro Ser
        35
```

<210> SEQ ID NO 98
<211> LENGTH: 40
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 98

```
Tyr Xaa Gln Gly Thr Phe Thr Ser Asp Tyr Ser Lys Ala Leu Asp Glu
1               5                   10                  15

Lys Ala Ala Lys Glu Phe Val Asn Trp Leu Leu Asp His His Pro Ser
            20                  25                  30

Ser Gly Gln Pro Pro Pro Ser Cys
        35                  40
```

<210> SEQ ID NO 99
<211> LENGTH: 40
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 99

```
Tyr Xaa Gln Gly Thr Phe Thr Ser Asp Tyr Ser Lys Ala Leu Asp Glu
1               5                   10                  15

Lys Ala Ala Lys Asp Phe Val Asn Trp Leu Leu Asp His His Pro Ser
            20                  25                  30

Ser Gly Gln Pro Pro Pro Ser Cys
        35                  40
```

<210> SEQ ID NO 100
<211> LENGTH: 40
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 100

```
Tyr Xaa Gln Gly Thr Phe Thr Ser Asp Tyr Ser Lys Ala Leu Asp Glu
1               5                   10                  15

Lys Ala Ala Lys Glu Phe Val Gln Trp Leu Leu Asp Gln His Pro Ser
            20                  25                  30

Ser Gly Gln Pro Pro Pro Ser Cys
        35                  40
```

<210> SEQ ID NO 101
<211> LENGTH: 40
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 101

```
Tyr Xaa Gln Gly Thr Phe Thr Ser Asp Tyr Ser Lys Ala Leu Asp Glu
1               5                   10                  15

Lys Ala Ala Lys Glu Phe Val Asn Trp Leu Leu Asp Gln His Pro Ser
            20                  25                  30

Ser Gly Gln Pro Pro Pro Ser Cys
        35                  40
```

<210> SEQ ID NO 102
<211> LENGTH: 40
<212> TYPE: PRT
<213> ORGANISM: Artificial
<220> FEATURE:
<223> OTHER INFORMATION: Triple agonist
<220> FEATURE:
<221> NAME/KEY: MISC_FEATURE
<222> LOCATION: (2)..(2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 102

```
Tyr Xaa Gln Gly Thr Phe Thr Ser Asp Tyr Ser Lys Ala Leu Asp Glu
1               5                   10                  15

Lys Ala Ala Lys Asp Phe Val Asn Trp Leu Leu Asp Gln His Pro Ser
            20                  25                  30
```

```
Ser Gly Gln Pro Pro Pro Ser Cys
        35                  40


<210> SEQ ID NO 103
<211> LENGTH: 30
<212> TYPE: PRT
<213> ORGANISM: Artificial
<220> FEATURE:
<223> OTHER INFORMATION: General Formula 1
<220> FEATURE:
<221> NAME/KEY: MISC_FEATURE
<222> LOCATION: (1)..(1)
<223> OTHER INFORMATION: Xaa is His (H), 4-imidazoacetyl (CA), or Tyr
      (Y)
<220> FEATURE:
<221> NAME/KEY: MISC_FEATURE
<222> LOCATION: (2)..(2)
<223> OTHER INFORMATION: Xaa is Gly (G), alpha-methyl-glutamic acid, or
      Aib (aminoisobutyric acid)
<220> FEATURE:
<221> NAME/KEY: MISC_FEATURE
<222> LOCATION: (3)..(3)
<223> OTHER INFORMATION: Xaa is Glu (E) or Gln (Q)
<220> FEATURE:
<221> NAME/KEY: MISC_FEATURE
<222> LOCATION: (7)..(7)
<223> OTHER INFORMATION: Xaa is Thr (T) or Ile (I)
<220> FEATURE:
<221> NAME/KEY: MISC_FEATURE
<222> LOCATION: (10)..(10)
<223> OTHER INFORMATION: Xaa is Leu (L), Tyr (Y), Lys (K), Cys (C), or
      Val (V)
<220> FEATURE:
<221> NAME/KEY: MISC_FEATURE
<222> LOCATION: (12)..(12)
<223> OTHER INFORMATION: Xaa is Lys (K), Ser (S), or Ile (I)
<220> FEATURE:
<221> NAME/KEY: MISC_FEATURE
<222> LOCATION: (13)..(13)
<223> OTHER INFORMATION: Xaa is Gln (Q), Tyr (Y), Ala (A), or Cys (C)
<220> FEATURE:
<221> NAME/KEY: MISC_FEATURE
<222> LOCATION: (14)..(14)
<223> OTHER INFORMATION: Xaa is Leu (L), Met (M), or Tyr (Y)
<220> FEATURE:
<221> NAME/KEY: MISC_FEATURE
<222> LOCATION: (15)..(15)
<223> OTHER INFORMATION: Xaa is Cys (C), Asp (D), Glu (E), or Leu (L)
<220> FEATURE:
<221> NAME/KEY: MISC_FEATURE
<222> LOCATION: (16)..(16)
<223> OTHER INFORMATION: Xaa is Gly (G), Glu (E), or Ser (S)
<220> FEATURE:
<221> NAME/KEY: MISC_FEATURE
<222> LOCATION: (17)..(17)
<223> OTHER INFORMATION: Xaa is Gln (Q), Arg (R), Ile (I), Glu (E), Cys
      (C), or Lys (K)
<220> FEATURE:
<221> NAME/KEY: MISC_FEATURE
<222> LOCATION: (18)..(18)
<223> OTHER INFORMATION: Xaa is Ala (A), Gln (Q), Arg (R), or His (H)
<220> FEATURE:
<221> NAME/KEY: MISC_FEATURE
<222> LOCATION: (19)..(19)
<223> OTHER INFORMATION: Xaa is Ala (A), Gln (Q), Cys (C), or Val (V)
<220> FEATURE:
<221> NAME/KEY: MISC_FEATURE
<222> LOCATION: (20)..(20)
<223> OTHER INFORMATION: Xaa is Lys (K), Gln (Q), or Arg (R)
<220> FEATURE:
<221> NAME/KEY: MISC_FEATURE
<222> LOCATION: (21)..(21)
<223> OTHER INFORMATION: Xaa is Glu (E), Gln (Q), Leu (L), Cys (C), or
      Asp (D)
<220> FEATURE:
<221> NAME/KEY: MISC_FEATURE
<222> LOCATION: (23)..(23)
<223> OTHER INFORMATION: Xaa is Ile (I) or Val (V)
```

```
<220> FEATURE:
<221> NAME/KEY: MISC_FEATURE
<222> LOCATION: (24)..(24)
<223> OTHER INFORMATION: Xaa is Ala (A), Gln (Q), Cys (C), Asn (N), Asp
      (D), or Glu (E)
<220> FEATURE:
<221> NAME/KEY: MISC_FEATURE
<222> LOCATION: (27)..(27)
<223> OTHER INFORMATION: Xaa is Val (V), Leu (L), Lys (K), or Met (M)
<220> FEATURE:
<221> NAME/KEY: MISC_FEATURE
<222> LOCATION: (28)..(28)
<223> OTHER INFORMATION: Xaa is Cys (C), Lys (K), Ala (A), Asn (N), or
      Asp (D)
<220> FEATURE:
<221> NAME/KEY: MISC_FEATURE
<222> LOCATION: (29)..(29)
<223> OTHER INFORMATION: Xaa is Cys (C), Gly (G), Gln (Q), Thr (T), Glu
      (E), or His (H)
<220> FEATURE:
<221> NAME/KEY: MISC_FEATURE
<222> LOCATION: (30)..(30)
<223> OTHER INFORMATION: Xaa is Cys, Gly, Lys, His, or is absent; Xaa
      can be further linked to R1, wherein R1 is Cys, GKKNDWKHNIT,
      m-SSGAPPPS-n, m-SSGQPPPS-n, or is absent, wherein m is Cys-,
      -Pro-, or -Gly-Pro-, and n is -Cys-, -Gly-, -Ser-, -His-Gly-, or
      is absent

<400> SEQUENCE: 103

Xaa Xaa Xaa Gly Thr Phe Xaa Ser Asp Xaa Ser Xaa Xaa Xaa Xaa Xaa
1               5                   10                  15

Xaa Xaa Xaa Xaa Xaa Phe Xaa Xaa Trp Leu Xaa Xaa Xaa Xaa
            20                  25                  30


<210> SEQ ID NO 104
<211> LENGTH: 40
<212> TYPE: PRT
<213> ORGANISM: Artificial
<220> FEATURE:
<223> OTHER INFORMATION: General Formula 2
<220> FEATURE:
<221> NAME/KEY: MISC_FEATURE
<222> LOCATION: (1)..(1)
<223> OTHER INFORMATION: Xaa is His (H), 4-imidazoacetyl (CA), or Tyr
      (Y)
<220> FEATURE:
<221> NAME/KEY: MISC_FEATURE
<222> LOCATION: (2)..(2)
<223> OTHER INFORMATION: Xaa is Gly (G), alpha-methyl-glutamic acid, or
      Aib (aminoisobutyric acid)
<220> FEATURE:
<221> NAME/KEY: MISC_FEATURE
<222> LOCATION: (10)..(10)
<223> OTHER INFORMATION: Xaa is Tyr (Y) or Cys (C)
<220> FEATURE:
<221> NAME/KEY: MISC_FEATURE
<222> LOCATION: (13)..(13)
<223> OTHER INFORMATION: Xaa is Gln (Q), Tyr (Y), Ala (A), or Cys (C)
<220> FEATURE:
<221> NAME/KEY: MISC_FEATURE
<222> LOCATION: (14)..(14)
<223> OTHER INFORMATION: Xaa is Leu (L), Met (M), or Tyr (Y)
<220> FEATURE:
<221> NAME/KEY: MISC_FEATURE
<222> LOCATION: (15)..(15)
<223> OTHER INFORMATION: Xaa is Asp (D), Glu (E), or Leu (L)
<220> FEATURE:
<221> NAME/KEY: MISC_FEATURE
<222> LOCATION: (16)..(16)
<223> OTHER INFORMATION: Xaa is Gly (G), Glu (E), or Ser (S)
<220> FEATURE:
<221> NAME/KEY: MISC_FEATURE
<222> LOCATION: (17)..(17)
<223> OTHER INFORMATION: Xaa is Gln (Q), Arg (R), Ile (I), Glu (E), Cys
      (C), or Lys (K)
<220> FEATURE:
```

<221> NAME/KEY: MISC_FEATURE
<222> LOCATION: (18)..(18)
<223> OTHER INFORMATION: Xaa is Ala (A), Gln (Q), Arg (R), or His (H)
<220> FEATURE:
<221> NAME/KEY: MISC_FEATURE
<222> LOCATION: (19)..(19)
<223> OTHER INFORMATION: Xaa is Ala (A), Gln (Q), Cys (C), or Val (V)
<220> FEATURE:
<221> NAME/KEY: MISC_FEATURE
<222> LOCATION: (20)..(20)
<223> OTHER INFORMATION: Xaa is Lys (K), Gln (Q), or Arg (R)
<220> FEATURE:
<221> NAME/KEY: MISC_FEATURE
<222> LOCATION: (21)..(21)
<223> OTHER INFORMATION: Xaa is Glu (E), Gln (Q), Leu (L), Cys (C), or Asp (D)
<220> FEATURE:
<221> NAME/KEY: MISC_FEATURE
<222> LOCATION: (23)..(23)
<223> OTHER INFORMATION: Xaa is Ile (I) or Val (V)
<220> FEATURE:
<221> NAME/KEY: MISC_FEATURE
<222> LOCATION: (24)..(24)
<223> OTHER INFORMATION: Xaa is Ala (A), Gln (Q), Cys (C), Asn (N), or Glu (E)
<220> FEATURE:
<221> NAME/KEY: MISC_FEATURE
<222> LOCATION: (28)..(28)
<223> OTHER INFORMATION: Xaa is Cys (C), Lys (K), Asn (N), or Asp (D)
<220> FEATURE:
<221> NAME/KEY: MISC_FEATURE
<222> LOCATION: (29)..(29)
<223> OTHER INFORMATION: Xaa is Cys (C), Gly (G), Gln (Q), or His (H)
<220> FEATURE:
<221> NAME/KEY: MISC_FEATURE
<222> LOCATION: (30)..(30)
<223> OTHER INFORMATION: Xaa is Cys (C), Gly (G), Lys (K), or His (H)
<220> FEATURE:
<221> NAME/KEY: MISC_FEATURE
<222> LOCATION: (31)..(31)
<223> OTHER INFORMATION: Xaa is Pro (P) or Cys (C)
<220> FEATURE:
<221> NAME/KEY: MISC_FEATURE
<222> LOCATION: (40)..(40)
<223> OTHER INFORMATION: Xaa is Cys (C), or is absent

<400> SEQUENCE: 104

```
Xaa Xaa Gln Gly Thr Phe Thr Ser Asp Xaa Ser Lys Xaa Xaa Xaa Xaa
1               5                   10                  15

Xaa Xaa Xaa Xaa Xaa Phe Xaa Xaa Trp Leu Leu Xaa Xaa Xaa Xaa Ser
            20                  25                  30

Ser Gly Gln Pro Pro Pro Ser Xaa
        35                  40
```

<210> SEQ ID NO 105
<211> LENGTH: 40
<212> TYPE: PRT
<213> ORGANISM: Artificial
<220> FEATURE:
<223> OTHER INFORMATION: General Formula 3
<220> FEATURE:
<221> NAME/KEY: MISC_FEATURE
<222> LOCATION: (1)..(1)
<223> OTHER INFORMATION: Xaa is His (H) or Tyr (Y)
<220> FEATURE:
<221> NAME/KEY: MISC_FEATURE
<222> LOCATION: (2)..(2)
<223> OTHER INFORMATION: Xaa is alpha-methyl-glutamic acid, or Aib (aminoisobutyric acid)
<220> FEATURE:
<221> NAME/KEY: MISC_FEATURE
<222> LOCATION: (13)..(13)
<223> OTHER INFORMATION: Xaa is Tyr (Y), Ala (A), or Cys (C)
<220> FEATURE:
<221> NAME/KEY: MISC_FEATURE
<222> LOCATION: (17)..(17)
<223> OTHER INFORMATION: Xaa is Arg (R), Cys (C), or Lys (K)
<220> FEATURE:
<221> NAME/KEY: MISC_FEATURE
<222> LOCATION: (18)..(18)
<223> OTHER INFORMATION: Xaa is Ala (A) or Arg (R)
<220> FEATURE:
<221> NAME/KEY: MISC_FEATURE
<222> LOCATION: (19)..(19)
<223> OTHER INFORMATION: Xaa is Ala (A) or Cys (C)
<220> FEATURE:
<221> NAME/KEY: MISC_FEATURE
<222> LOCATION: (21)..(21)
<223> OTHER INFORMATION: Xaa is Glu (E) or Asp (D)
<220> FEATURE:
<221> NAME/KEY: MISC_FEATURE
<222> LOCATION: (24)..(24)
<223> OTHER INFORMATION: Xaa is Gln (Q) or Asn (N)
<220> FEATURE:
<221> NAME/KEY: MISC_FEATURE
<222> LOCATION: (28)..(28)
<223> OTHER INFORMATION: Xaa is Cys (C) or Asp (D)
<220> FEATURE:
<221> NAME/KEY: MISC_FEATURE
<222> LOCATION: (29)..(29)
<223> OTHER INFORMATION: Xaa is Cys (C), Gln (Q), or His (H)
<220> FEATURE:
<221> NAME/KEY: MISC_FEATURE
<222> LOCATION: (30)..(30)
<223> OTHER INFORMATION: Xaa is Cys (C) or His (H)
<220> FEATURE:
<221> NAME/KEY: MISC_FEATURE
<222> LOCATION: (31)..(31)
<223> OTHER INFORMATION: Xaa is Pro (P) or Cys (C)
<220> FEATURE:
<221> NAME/KEY: MISC_FEATURE
<222> LOCATION: (40)..(40)
<223> OTHER INFORMATION: Xaa is Cys (C), or is absent

<400> SEQUENCE: 105

```
Xaa Xaa Gln Gly Thr Phe Thr Ser Asp Tyr Ser Lys Xaa Leu Asp Glu
1               5                   10                  15

Xaa Xaa Xaa Lys Xaa Phe Val Xaa Trp Leu Leu Xaa Xaa Xaa Xaa Ser
            20                  25                  30

Ser Gly Gln Pro Pro Pro Ser Xaa
        35                  40
```

<210> SEQ ID NO 106
<211> LENGTH: 11
<212> TYPE: PRT
<213> ORGANISM: Artificial
<220> FEATURE:
<223> OTHER INFORMATION: R1

<400> SEQUENCE: 106

```
Gly Lys Lys Asn Asp Trp Lys His Asn Ile Thr
1               5                   10
```

<210> SEQ ID NO 107
<211> LENGTH: 8
<212> TYPE: PRT
<213> ORGANISM: Artificial
<220> FEATURE:
<223> OTHER INFORMATION: R1

<400> SEQUENCE: 107

```
Ser Ser Gly Ala Pro Pro Pro Ser
1               5
```

<210> SEQ ID NO 108
<211> LENGTH: 8

<212> TYPE: PRT
<213> ORGANISM: Artificial
<220> FEATURE:
<223> OTHER INFORMATION: R1

<400> SEQUENCE: 108

Ser Ser Gly Gln Pro Pro Pro Ser
1 5

<210> SEQ ID NO 109
<211> LENGTH: 9
<212> TYPE: PRT
<213> ORGANISM: Artificial
<220> FEATURE:
<223> OTHER INFORMATION: R1

<400> SEQUENCE: 109

Cys Ser Ser Gly Gln Pro Pro Pro Ser
1 5

<210> SEQ ID NO 110
<211> LENGTH: 10
<212> TYPE: PRT
<213> ORGANISM: Artificial
<220> FEATURE:
<223> OTHER INFORMATION: R1

<400> SEQUENCE: 110

Gly Pro Ser Ser Gly Ala Pro Pro Pro Ser
1 5 10

<210> SEQ ID NO 111
<211> LENGTH: 11
<212> TYPE: PRT
<213> ORGANISM: Artificial
<220> FEATURE:
<223> OTHER INFORMATION: R1

<400> SEQUENCE: 111

Gly Pro Ser Ser Gly Ala Pro Pro Pro Ser Cys
1 5 10

<210> SEQ ID NO 112
<211> LENGTH: 9
<212> TYPE: PRT
<213> ORGANISM: Artificial
<220> FEATURE:
<223> OTHER INFORMATION: R1

<400> SEQUENCE: 112

Pro Ser Ser Gly Ala Pro Pro Pro Ser
1 5

<210> SEQ ID NO 113
<211> LENGTH: 10
<212> TYPE: PRT
<213> ORGANISM: Artificial
<220> FEATURE:
<223> OTHER INFORMATION: R1

<400> SEQUENCE: 113

Pro Ser Ser Gly Ala Pro Pro Pro Ser Gly
1 5 10

<210> SEQ ID NO 114
<211> LENGTH: 11
<212> TYPE: PRT

<213> ORGANISM: Artificial
<220> FEATURE:
<223> OTHER INFORMATION: R1

<400> SEQUENCE: 114

Pro Ser Ser Gly Ala Pro Pro Pro Ser His Gly
1 5 10

<210> SEQ ID NO 115
<211> LENGTH: 10
<212> TYPE: PRT
<213> ORGANISM: Artificial
<220> FEATURE:
<223> OTHER INFORMATION: R1

<400> SEQUENCE: 115

Pro Ser Ser Gly Ala Pro Pro Pro Ser Ser
1 5 10

<210> SEQ ID NO 116
<211> LENGTH: 9
<212> TYPE: PRT
<213> ORGANISM: Artificial
<220> FEATURE:
<223> OTHER INFORMATION: R1

<400> SEQUENCE: 116

Pro Ser Ser Gly Gln Pro Pro Pro Ser
1 5

<210> SEQ ID NO 117
<211> LENGTH: 10
<212> TYPE: PRT
<213> ORGANISM: Artificial
<220> FEATURE:
<223> OTHER INFORMATION: R1

<400> SEQUENCE: 117

Pro Ser Ser Gly Gln Pro Pro Pro Ser Cys
1 5 10

<210> SEQ ID NO 118
<211> LENGTH: 29
<212> TYPE: PRT
<213> ORGANISM: Homo sapiens

<400> SEQUENCE: 118

His Ser Gln Gly Thr Phe Thr Ser Asp Tyr Ser Lys Tyr Leu Asp Ser
1 5 10 15

Arg Arg Ala Gln Asp Phe Val Gln Trp Leu Met Asn Thr
20 25

<210> SEQ ID NO 119
<211> LENGTH: 12
<212> TYPE: PRT
<213> ORGANISM: Homo sapiens

<400> SEQUENCE: 119

Glu Ser Lys Tyr Gly Pro Pro Cys Pro Ser Cys Pro
1 5 10

<210> SEQ ID NO 120
<211> LENGTH: 11
<212> TYPE: PRT
<213> ORGANISM: Artificial
<220> FEATURE:

-continued

<223> OTHER INFORMATION: Variant of hinge region

<400> SEQUENCE: 120

```
Glu Ser Lys Tyr Gly Pro Pro Pro Ser Cys Pro
1               5                   10
```

<210> SEQ ID NO 121
<211> LENGTH: 11
<212> TYPE: PRT
<213> ORGANISM: Artificial
<220> FEATURE:
<223> OTHER INFORMATION: Variant of hinge region

<400> SEQUENCE: 121

```
Glu Ser Lys Tyr Gly Pro Pro Cys Pro Ser Pro
1               5                   10
```

<210> SEQ ID NO 122
<211> LENGTH: 10
<212> TYPE: PRT
<213> ORGANISM: Artificial
<220> FEATURE:
<223> OTHER INFORMATION: Variant of hinge region

<400> SEQUENCE: 122

```
Glu Ser Lys Tyr Gly Pro Pro Cys Pro Ser
1               5                   10
```

<210> SEQ ID NO 123
<211> LENGTH: 10
<212> TYPE: PRT
<213> ORGANISM: Artificial
<220> FEATURE:
<223> OTHER INFORMATION: Variant of hinge region

<400> SEQUENCE: 123

```
Glu Ser Lys Tyr Gly Pro Pro Cys Pro Pro
1               5                   10
```

<210> SEQ ID NO 124
<211> LENGTH: 8
<212> TYPE: PRT
<213> ORGANISM: Artificial
<220> FEATURE:
<223> OTHER INFORMATION: Variant of hinge region

<400> SEQUENCE: 124

```
Lys Tyr Gly Pro Pro Cys Pro Ser
1               5
```

<210> SEQ ID NO 125
<211> LENGTH: 8
<212> TYPE: PRT
<213> ORGANISM: Artificial
<220> FEATURE:
<223> OTHER INFORMATION: Variant of hinge region

<400> SEQUENCE: 125

```
Glu Ser Lys Tyr Gly Pro Pro Cys
1               5
```

<210> SEQ ID NO 126
<211> LENGTH: 7
<212> TYPE: PRT
<213> ORGANISM: Artificial
<220> FEATURE:
<223> OTHER INFORMATION: Variant of hinge region

<400> SEQUENCE: 126

Glu Lys Tyr Gly Pro Pro Cys
1 5

<210> SEQ ID NO 127
<211> LENGTH: 6
<212> TYPE: PRT
<213> ORGANISM: Artificial
<220> FEATURE:
<223> OTHER INFORMATION: Variant of hinge region

<400> SEQUENCE: 127

Glu Ser Pro Ser Cys Pro
1 5

<210> SEQ ID NO 128
<211> LENGTH: 5
<212> TYPE: PRT
<213> ORGANISM: Artificial
<220> FEATURE:
<223> OTHER INFORMATION: Variant of hinge region

<400> SEQUENCE: 128

Glu Pro Ser Cys Pro
1 5

<210> SEQ ID NO 129
<211> LENGTH: 4
<212> TYPE: PRT
<213> ORGANISM: Artificial
<220> FEATURE:
<223> OTHER INFORMATION: Variant of hinge region

<400> SEQUENCE: 129

Pro Ser Cys Pro
1

<210> SEQ ID NO 130
<211> LENGTH: 10
<212> TYPE: PRT
<213> ORGANISM: Artificial
<220> FEATURE:
<223> OTHER INFORMATION: Variant of hinge region

<400> SEQUENCE: 130

Glu Ser Lys Tyr Gly Pro Pro Ser Cys Pro
1 5 10

<210> SEQ ID NO 131
<211> LENGTH: 9
<212> TYPE: PRT
<213> ORGANISM: Artificial
<220> FEATURE:
<223> OTHER INFORMATION: Variant of hinge region

<400> SEQUENCE: 131

Lys Tyr Gly Pro Pro Pro Ser Cys Pro
1 5

<210> SEQ ID NO 132
<211> LENGTH: 9
<212> TYPE: PRT
<213> ORGANISM: Artificial
<220> FEATURE:
<223> OTHER INFORMATION: Variant of hinge region

<400> SEQUENCE: 132

Glu Ser Lys Tyr Gly Pro Ser Cys Pro
1 5

<210> SEQ ID NO 133
<211> LENGTH: 8
<212> TYPE: PRT
<213> ORGANISM: Artificial
<220> FEATURE:
<223> OTHER INFORMATION: Variant of hinge region

<400> SEQUENCE: 133

Glu Ser Lys Tyr Gly Pro Pro Cys
1 5

<210> SEQ ID NO 134
<211> LENGTH: 7
<212> TYPE: PRT
<213> ORGANISM: Artificial
<220> FEATURE:
<223> OTHER INFORMATION: Variant of hinge region

<400> SEQUENCE: 134

Lys Tyr Gly Pro Pro Cys Pro
1 5

<210> SEQ ID NO 135
<211> LENGTH: 7
<212> TYPE: PRT
<213> ORGANISM: Artificial
<220> FEATURE:
<223> OTHER INFORMATION: Variant of hinge region

<400> SEQUENCE: 135

Glu Ser Lys Pro Ser Cys Pro
1 5

<210> SEQ ID NO 136
<211> LENGTH: 6
<212> TYPE: PRT
<213> ORGANISM: Artificial
<220> FEATURE:
<223> OTHER INFORMATION: Variant of hinge region

<400> SEQUENCE: 136

Glu Ser Pro Ser Cys Pro
1 5

<210> SEQ ID NO 137
<211> LENGTH: 4
<212> TYPE: PRT
<213> ORGANISM: Artificial
<220> FEATURE:
<223> OTHER INFORMATION: Variant of hinge region

<400> SEQUENCE: 137

Glu Pro Ser Cys
1

<210> SEQ ID NO 138
<211> LENGTH: 3
<212> TYPE: PRT
<213> ORGANISM: Artificial
<220> FEATURE:
<223> OTHER INFORMATION: Variant of hinge region

<400> SEQUENCE: 138

```
Ser Cys Pro
1


<210> SEQ ID NO 139
<211> LENGTH: 5
<212> TYPE: PRT
<213> ORGANISM: Artificial
<220> FEATURE:
<223> OTHER INFORMATION: Synthetic construct (linker)

<400> SEQUENCE: 139

Gly Gly Gly Gly Ser
1               5


<210> SEQ ID NO 140
<211> LENGTH: 5
<212> TYPE: PRT
<213> ORGANISM: Artificial
<220> FEATURE:
<223> OTHER INFORMATION: Synthetic construct (linker)

<400> SEQUENCE: 140

Ser Gly Gly Gly Gly
1               5


<210> SEQ ID NO 141
<211> LENGTH: 5
<212> TYPE: PRT
<213> ORGANISM: Artificial
<220> FEATURE:
<223> OTHER INFORMATION: Synthetic construct (linker)

<400> SEQUENCE: 141

Ser Arg Ser Ser Gly
1               5


<210> SEQ ID NO 142
<211> LENGTH: 5
<212> TYPE: PRT
<213> ORGANISM: Artificial
<220> FEATURE:
<223> OTHER INFORMATION: Synthetic construct (linker)

<400> SEQUENCE: 142

Ser Gly Ser Ser Cys
1               5


<210> SEQ ID NO 143
<211> LENGTH: 12
<212> TYPE: PRT
<213> ORGANISM: Artificial
<220> FEATURE:
<223> OTHER INFORMATION: Synthetic construct (linker)

<400> SEQUENCE: 143

Gly Lys Ser Ser Gly Ser Gly Ser Glu Ser Lys Ser
1               5                   10


<210> SEQ ID NO 144
<211> LENGTH: 6
<212> TYPE: PRT
<213> ORGANISM: Artificial
<220> FEATURE:
<223> OTHER INFORMATION: Synthetic construct (linker)

<400> SEQUENCE: 144
```

-continued

Arg Pro Pro Pro Pro Cys
1 5

<210> SEQ ID NO 145
<211> LENGTH: 7
<212> TYPE: PRT
<213> ORGANISM: Artificial
<220> FEATURE:
<223> OTHER INFORMATION: Synthetic construct (linker)

<400> SEQUENCE: 145

Ser Ser Pro Pro Pro Pro Cys
1 5

<210> SEQ ID NO 146
<211> LENGTH: 14
<212> TYPE: PRT
<213> ORGANISM: Artificial
<220> FEATURE:
<223> OTHER INFORMATION: Synthetic construct (linker)

<400> SEQUENCE: 146

Gly Ser Thr Ser Gly Ser Gly Lys Ser Ser Glu Gly Lys Gly
1 5 10

<210> SEQ ID NO 147
<211> LENGTH: 18
<212> TYPE: PRT
<213> ORGANISM: Artificial
<220> FEATURE:
<223> OTHER INFORMATION: Synthetic construct (linker)

<400> SEQUENCE: 147

Gly Ser Thr Ser Gly Ser Gly Lys Ser Ser Glu Gly Ser Gly Ser Thr
1 5 10 15

Lys Gly

<210> SEQ ID NO 148
<211> LENGTH: 18
<212> TYPE: PRT
<213> ORGANISM: Artificial
<220> FEATURE:
<223> OTHER INFORMATION: Synthetic construct (linker)

<400> SEQUENCE: 148

Gly Ser Thr Ser Gly Ser Gly Lys Pro Gly Ser Gly Glu Gly Ser Thr
1 5 10 15

Lys Gly

<210> SEQ ID NO 149
<211> LENGTH: 14
<212> TYPE: PRT
<213> ORGANISM: Artificial
<220> FEATURE:
<223> OTHER INFORMATION: Synthetic construct (linker)

<400> SEQUENCE: 149

Glu Gly Lys Ser Ser Gly Ser Gly Ser Glu Ser Lys Glu Phe
1 5 10

METHOD FOR TREATING, OR REDUCING THE LIKELIHOOD OF DEVELOPING, A LUPUS-ASSOCIATED DISEASE BY ADMINISTERING A PHARMACEUTICAL COMPOSITION COMPRISING GLUCAGON/GLP-1/GIP TRIPLE AGONIST OR LONG-ACTING CONJUGATE THEREOF

CROSS REFERENCE TO RELATED APPLICATIONS

This application is a National Stage of International Application No. PCT/KR2021/014468 filed Oct. 18, 2021, claiming priority based on Korean Patent Application No. 10-2020-0134482 filed Oct. 16, 2020.

INCORPORATION BY REFERENCE OF SEQUENCE LISTING

The content of the electronically submitted sequence listing, file name: Q286820_SEQ_LIS_AS_FILED.txt; size: 74,627 bytes; and date of creation: Apr. 30, 2023, filed herewith, is incorporated herein by reference in its entirety.

TECHNICAL FIELD

The present disclosure relates to a pharmaceutical composition for preventing or treating lupus-associated disease including a glucagon/GLP-1/GIP triple agonist or a long-acting conjugate thereof.

BACKGROUND ART

Systemic lupus erythematosus, also referred to as systemic lupus erythematosus, lupus, or S.L.E, is a chronic inflammatory autoimmune disease in which autoantibodies against specific proteins in cell nuclei are produced and own cells or tissues are destroyed by abnormalities in the immune system. In most cases, lupus only causes mild symptoms such as skin rash, but in some patients, it can cause serious immune-related abnormal symptoms in major organs of the body such as the brain, lungs, and kidneys.

The exact cause of lupus is not known. It is believed that lupus arises from a complex interplay of genetic, hormonal, and environmental factors. In addition to genetic factors and hormonal and environmental factors, lupus can also be triggered by factors such as exposure to ultraviolet radiation, silica dust, smoking, and drugs.

The number of patients with lupus is increasing every year. According to statistics from the Health Insurance Review & Assessment Service (HIRA) in 2017, 25,757 people received treatment for lupus, and the number of patients increased by about 3,000 (13.5%) over the three years from 2015 to 2017. By age group, the most common age group for treatment was in their 40s (26.6%), followed by those in their 30s (22.2%) and 50s (21.9%). The proportion of female patients (86.3%) was about 6.3 times higher than that of male patients (13.7%). Therefore, it is important for women in their 30s to 50s to be particularly careful.

Lupus is classified as small vessel vasculitis, but it is different from other types of vasculitis in that it affects not only specific areas of blood vessels but also all tissues in the body, including the skin, nervous tissue, lungs, kidneys, heart, and hematopoietic organs, in addition to joints and muscles. In the same context, predicting the progression of the disease in lupus is difficult, and it manifests with various symptoms, which makes diagnosis and treatment clinically challenging.

Glucagon-like peptide-1 (GLP-1) and glucose-dependent insulinotropic polypeptide (GIP) are representative gastrointestinal hormones and neurohormones, and are substances involved in regulating glucose concentrations in the blood. Glucagon is a peptide hormone secreted by the pancreas, and together with the two substances described above, is involved in regulating glucose concentrations in the blood.

GLP-1 is a hormone secreted from the small intestine in response to food intake. GLP-1 promotes the secretion of insulin from the pancreas in a blood glucose concentration-dependent manner and suppresses the secretion of glucagon to help lower blood glucose levels. In addition, GLP-1 acts as a satiety factor to slow down the digestive process of the stomach and delays the gastric transit time of digested food, thereby reducing food intake. Moreover, when administered to rats, GLP-1 exhibits the effects of suppressing food intake and reducing body weight, and these effects appear equally in both normal and obese states, showing the potential as a treatment for obesity.

GIP is a representative hormone (incretin hormone) secreted from the gastrointestinal tract and a hormone consisting of 42 amino acids secreted from K cells of the small intestine. GIP promotes the secretion of insulin or glucagon in the pancreas in a blood glucose concentration-dependent manner to help maintain blood glucose homeostasis, and recent studies have reported dietary suppression and anti-inflammatory effects.

Glucagon is produced in the pancreas when blood glucose begins to drop due to drug treatment or disease, the deficiency of hormone or enzyme, etc. Glucagon signals to the liver to break down glycogen and release glucose, raising blood glucose levels to normal levels. In addition to the effect of increasing blood glucose, glucagon suppresses appetite in animals and humans and activates hormone sensitive lipase in fat cells to promote fat decomposition and energy expenditure, thereby exhibiting an anti-obesity effect.

In addition, these GLP-1, GIP, and glucagon hormones have been reported to each have anti-inflammatory effects. The inventors have completed the invention by developing a triple-acting agent that simultaneously activates glucagon, GLP-1, and GIP receptors and confirming its potential as a treatment for lupus-associated diseases.

DETAILED DESCRIPTION OF THE DISCLOSURE

Technical Problem

Provided is a pharmaceutical composition for preventing or treating lupus-associated disease, including a glucagon/GLP-1/GIP triple agonist, a pharmaceutically acceptable salt thereof, a solvate thereof, or a conjugate thereof.

Provided is a method of preventing or treating lupus-associated disease, including administering an effective amount of the glucagon/GLP-1/GIP triple agonist, a pharmaceutically acceptable salt thereof, a solvate thereof, or a conjugate thereof, or the pharmaceutical composition to a subject in need thereof.

Provided is use of the glucagon/GLP-1/GIP triple agonist, a pharmaceutically acceptable salt thereof, the solvate thereof, or a conjugate thereof for use in preparing a drug for preventing or treating lupus-associated disease.

Technical Solution to Problem

Throughout this specification, for naturally occurring amino acids, the usual one-letter and three-letter codes are used, and for other amino acids such as Aib (α-aminoisobutyric acid), Sar (N-methylglycine), α-methyl-glutamic acid, etc., a generally accepted three-letter code is used. Amino acids which are referred to by abbreviations herein are described according to the IUPAC-IUB nomenclature.

| | |
|---|---|
| Alanine Ala, A | Arginine Arg, R |
| Asparagine Asn, N | Aspartate Asp, D |
| Cysteine Cys, C | Glutamic acid Glu, E |
| Glutamine Gln, Q | Glycine Gly, G |
| Histidine His, H | Isoleucine Ile, I |
| Leucine Leu, L | Lysine Lys, K |
| Methionine Met, M | Phenylalanine Phe, F |
| Proline Pro, P | Serine Ser, S |
| Threonine Thr, T | Tryptophan Trp, W |
| Tyrosine Tyr, Y | Valine Val, V |

Another aspect provides a pharmaceutical composition for preventing or treating lupus-associated disease including the glucagon/GLP-1/GIP triple agonist, a pharmaceutically acceptable salt thereof or a solvate thereof.

"Glucagon (GCG)" is a hormone secreted from a cells in the islets of Langerhans of the pancreas, and has a feedback relationship with insulin by acting opposite thereto.

The term "glucagon-like peptide-1 (GLP-1)" used herein is a hormone secreted by L cells in the small intestine in response to food intake. GLP-1 promotes the secretion of insulin from the pancreas in a blood glucose concentration-dependent manner and suppresses the secretion of glucagon to help lower the blood glucose concentration.

The term "glucose-dependent insulinotropic polypeptide or gastric inhibitory polypeptide (GIP)" used herein is a hormone secreted from K cells in the small intestine when stimulated by food intake, and was first reported as a substance involved in regulating blood glucose concentration.

The "glucagon/GLP-1/GIP triple agonist" may be used interchangeably with "GCG/GLP-1/GIP triple agonist", "GCG/GLP-1/GIP receptor triple agonist", "GCG receptor, GLP-1 receptor, and GIP receptor triple agonist", "GCGR/GLP-1R/GIPR triple agonist", "triple agonist", or "peptide having activity on glucagon receptor, GLP-1 receptor, and GIP receptor."

The glucagon/GLP-1/GIP triple agonist may be a peptide having activity on glucagon receptor, GLP-1 receptor, and GIP receptor. The "peptide having activity on the glucagon receptor, the GLP-1 receptor, and the GIP receptor" has a significant level of activity on the glucagon receptor, the GLP-1 receptor, and the GIP receptor, and specifically, the in vitro activity on the glucagon receptor, the GLP-1 receptor, and the GIP receptor may be, with respect to a native-type ligand (native-type glucagon, native-type GLP-1 or native-type GIP), about 0.1% or more, about 1% or more, about 2% or more, about 3% or more, about 4% or more, about 5% or more, about 6% or more, about 7% or more, about 8% or more, about 9% or more, about 10% or more, about % or more, about 30% or more, about 40% or more, about 50% or more, about 60% or more, about 70% or more, about 80% or more, about 90% or more, about 100% or more, about 100% to about 500%, or about 100% to about 200%. For a method for measuring the in vitro activity of peptides having activity on the glucagon receptor the GLP-1 receptor and GIP receptor, Example 1 of the present specification may be referred to. However, the method is not limited thereto, and any method that is known in the art, may be appropriately used.

"About" is a range that includes all of ±0.5, ±0.4, ±0.3, ±0.2, ±0.1, etc., and includes all ranges equal to or similar to the numerical value following the term "about." However, the definition of "about" is not limited thereto.

The peptide may have an in vivo half-life that is increased compared to any one of native-type GLP-1, native-type glucagon and native-type GIP, but is not particularly limited thereto.

The peptide may be an analog of native-type glucagon, but is not limited thereto.

Analogs of the native-type glucagon include peptides having one or more differences in amino acid sequence with respect to native-type glucagon, peptides changed through a modification in the native-type glucagon sequence, or mimics of native-type glucagon.

On the other hand, native-type glucagon may have the following amino acid sequence:

His-Ser-Gln-Gly-Thr-Phe-Thr-Ser-Asp-Tyr-Ser-Lys-
Tyr-Leu-Asp-Ser-Arg-Arg-Ala-Gln-Asp-Phe-
Val-Gln-Trp-Leu-Met-Asn-Thr (SEQ ID NO: 118)

In an embodiment, the peptide may be an analog of native-type glucagon in which at least one amino acid in the native-type glucagon sequence has been modified. The modification may be selected from the group consisting of substitution, addition, deletion, modification, and a combination of two or more thereof.

The substitution may include both a substitution with an amino acid or a substitution with a non-native-type compound.

The addition may be made to the N-terminus and/or C-terminus of the peptide. Meanwhile, the length of the added amino acid is not particularly limited, and 1 or more, 2 or more, 3 or more, 4 or more, 5 or more, 6 or more, 7 or more, 8 or more, 9 or more, or more, 11 or more amino acids are added. Broadly, the addition may include the addition of a polypeptide, and is not particularly limited thereto.

In an embodiment, regarding the glucagon analog, 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 amino acids selected from the group consisting of a $1^{st}$ amino acid, a $2^{nd}$ amino acid, a $3^{rd}$ amino acid, a $7^{th}$ amino acid, a $10^{th}$ amino acid, a $12^{th}$ amino acid, a $13^{th}$ amino acid, a $14^{th}$ amino acid, a $15^{th}$ amino acid, a $16^{th}$ amino acid, a $17^{th}$ amino acid, a $18^{th}$ amino acid, a $19^{th}$ amino acid, a $20^{th}$ amino acid, a $21^{st}$ amino acid, a $23^{rd}$ amino acid, a $24^{th}$ amino acid, a $27^{th}$ amino acid, a $28^{th}$ amino acid, and a $29^{th}$ amino acid, of a native-type glucagon amino acid sequence, are substituted with other amino acids. Also, 1 or more, 2 or more, 3 or more, 4 or more, 5 or more, 6 or more, 7 or more, 8 or more, 9 or more, 10 or more, or 11 or more amino acids may be independently or additionally added to at the C-terminus. However, the present disclosure is not limited thereto.

In an embodiment, regarding the glucagon analog, 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, or 19 or more amino acids selected from the group consisting of a $1^{st}$ amino acid, a $2^{nd}$ amino acid, a $3^{rd}$ amino acid, a $10^{th}$ amino acid, a $12^{th}$ amino acid, a $13^{th}$ amino acid, a $14^{th}$ amino acid, a $15^{th}$ amino acid, a $16^{th}$ amino acid, a $17^{th}$ amino acid, a $18^{th}$ amino acid, a $19^{th}$ amino acid, a $20^{th}$ amino acid, a $21^{st}$ amino acid, a $23^{rd}$ amino acid, a $24^{th}$ amino acid, a $27^{th}$ amino acid, a $28^{th}$ amino acid, and a $29^{th}$ amino acid, of a native-type glucagon amino acid sequence, are substituted with other amino acids. Also, 1 or more, 2 or more, 3 or more, 4 or more, 5 or more, 6 or more, 7 or more, 8 or more, 9 or more, or more, or 11 or more amino acids may be independently or additionally added to at the C-terminus. However, the present disclosure is not limited thereto.

In an embodiment, regarding the glucagon analog, 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, or 17 or more amino acids selected from the group consisting of a $1^{st}$ amino acid, a $2^{nd}$ amino acid, a $3^{rd}$ amino acid, a $10^{th}$ amino acid, a $13^{th}$ amino acid, a $14^{th}$ amino acid, a $15^{th}$ amino acid, a $16^{th}$ amino acid, a $17^{th}$ amino acid, a $18^{th}$ amino acid, a $19^{th}$ amino acid, a $20^{th}$ amino acid, a $21^{st}$ amino acid, a $23^{rd}$ amino acid, a $24^{th}$ amino acid, a $28^{th}$ amino acid, and a $29^{th}$ amino acid, of a native-type glucagon amino acid sequence, are substituted with other amino acids. Also, 1 or more, 2 or more, 3 or more, 4 or more, 5 or more, 6 or more, 7 or more, 8 or more, 9 or more, 10 or more, or 11 or more amino acids may be independently or additionally added to at the C-terminus. However, the present disclosure is not limited thereto.

In an embodiment, regarding the glucagon analog, 1 or more, 2 or more, 3 or more, 4 or more, 5 or more, 6 or more, 7 or more, 8 or more, 9 or more, 10 or more, 11 or more, 12 or more, 13 or more, or 14 amino acids having the sequence selected from the group consisting of a $1^{st}$ amino acid, a $2^{nd}$ amino acid, a $13^{th}$ amino acid, a $16^{th}$ amino acid, a $17^{th}$ amino acid, a $18^{th}$ amino acid, a $19^{th}$ amino acid, a $20^{th}$ amino acid, a $21^{st}$ amino acid, a $23^{rd}$ amino acid, a $24^{th}$ amino acid, a $27^{th}$ amino acid, a $28^{th}$ amino acid, and a $29^{th}$ amino acid, of a native-type glucagon amino acid sequence, are substituted with other amino acids. Also, 1 or more, 2 or more, 3 or more, 4 or more, 5 or more, 6 or more, 7 or more, 8 or more, 9 or more, 10 or more, or 11 or more amino acids may be independently or additionally added to at the C-terminus. However, the present disclosure is not limited thereto.

Amino acids introduced from the native-type glucagon may be selected from the group consisting of tyrosine, alpha-methyl-glutamic acid, Aib, methionine, glutamic acid, histidine, lysine, leucine, isoleucine, glutamine, valine, glycine, alanine, cysteine, serine, alanine, aspartic acid, and arginine, but are not particularly limited thereto.

For example, the added amino acid sequence may be derived from a native-type GLP-1, a native-type GIP, or a native-type exendin-4 amino acid sequence.

The glucagon/GLP-1/GIP triple agonist may be non-naturally occurring.

The glucagon/GLP-1/GIP triple agonist may be an isolated peptide.

In an embodiment, the glucagon/GLP-1/GIP triple agonist may be a peptide including an amino acid sequence represented by General Formula 1:

Xaa1-Xaa2-Xaa3-Gly-Thr-Phe-Xaa7-Ser-Asp-Xaa10-Ser-Xaa12-Xaa13-Xaa14-Xaa15-Xaa16-Xaa17-Xaa18-Xaa19-Xaa20-Xaa21-Phe-Xaa23-Xaa24-Trp-Leu-Xaa27-Xaa28-Xaa29-Xaa30-R1 (General Formula 1, SEQ ID NO: 103), In General Formula 1, Xaa1 may be histidine (His, H), 4-imidazoacetyl (CA), or tyrosine (Tyr, Y), Xaa2 may be glycine (Gly, G), alpha-methyl-glutamic acid, or aminoisobutyric acid (Aib), Xaa3 may be glutamic acid (Glu, E) or glutamine (Gln, Q), Xaa7 may be threonine (Thr, T) or isoleucine (Ile, I), Xaa10 may be leucine (Leu, L), tyrosine (Tyr, Y), lysine (Lys, K), cysteine (Cys, C), or valine (Val, V), Xaa12 may be lysine (Lys, K), serine (Ser, S), or isoleucine (Ile, I), Xaa13 may be glutamine (Gln, Q), tyrosine (Tyr, Y), alanine (Ala, A), or cysteine (Cys, C), Xaa14 may be leucine (Leu, L), methionine (Met, M), or tyrosine (Tyr, Y), Xaa15 may be cysteine (Cys, C), aspartic acid (Asp, D), glutamic acid (Glu, E), or leucine (Leu, L), Xaa16 may be glycine (Gly, G), glutamic acid (Glu, E), or serine (Ser, S), Xaa17 may be glutamine (Gln, Q), arginine (Arg, R), isoleucine (Ile, I), glutamic acid (Glu, E), cysteine (Cys, C), or lysine (Lys, K), Xaa18 may be alanine (Ala, A), glutamine (Gln, Q), arginine (Arg, R), or histidine (His, H), Xaa19 may be alanine (Ala, A), glutamine (Gln, Q), cysteine (Cys, C), or valine (Val, V), Xaa20 may be lysine (Lys, K), glutamine (Gln, Q), or arginine (Arg, R), Xaa21 may be glutamic acid (Glu, E), glutamine (Gln, Q), leucine (Leu, L), cysteine (Cys, C), or aspartic acid (Asp, D), Xaa23 may be isoleucine (Ile, I) or valine (Val, V);

Xaa24 may be alanine (Ala, A), glutamine (Gln, Q), cysteine (Cys, C), asparagine (Asn, N), aspartic acid (Asp, D), or glutamic acid (Glu, E), Xaa27 may be valine (Val, V), leucine (Leu, L), lysine (Lys, K), or methionine (Met, M), Xaa28 may be cysteine (Cys, C), lysine (Lys, K), alanine (Ala, A), asparagine (Asn, N), or aspartic acid (Asp, D), Xaa29 may be cysteine (Cys, C), glycine (Gly, G), glutamine (Gln, Q), threonine (Thr, T), glutamic acid (Glu, E), or histidine (His, H), Xaa30 may be cysteine (Cys, C), glycine (Gly, G), lysine (Lys, K), or histidine (His, H), or may be absent;

R1 may be cysteine (Cys, C), GKKNDWKHNIT (SEQ ID NO: 106), m-SSGAPPPS-n (SEQ ID NO: 107), or m-SSGQPPPS-n (SEQ ID NO: 108), or may be absent, wherein m may be -Cys-, -Pro-, or -Gly-Pro-, and n may be -Cys-, -Gly-, -Ser-, or -His-Gly-, or may be absent.

An example of such a triple agonist includes a peptide that includes an amino acid sequence selected from the group consisting of SEQ ID NOs: 1 to 102, a peptide that consists essentially of an amino acid sequence selected from the group consisting of SEQ ID NOs: 1 to 102, and a peptide that consists of an amino acid sequence selected from the group consisting of SEQ ID NOs: 1 to 102. However, the triple agonist is not limited thereto.

In another embodiment, in General Formula 1,

Xaa14 may be leucine or methionine,

Xaa15 may be cysteine, aspartic acid, or leucine.

An example of the triple agonist includes a peptide that includes an amino acid sequence selected from the group consisting of SEQ ID NOs: 1 to 12, 14 to 17, and 21 to 102, a peptide that consists essentially of an amino acid sequence selected from the group consisting of SEQ ID NOs: 1 to 12, 14 to 17, and 21 to 102, and a peptide that consists of an amino acid sequence selected from the group consisting of SEQ ID NOs: 1 to 12, 14 to 17, and 21 to 102, but is not limited thereto.

These peptides may significantly activate one or more of the glucagon receptor, the GLP-1 receptor, and the GIP receptor, but are not particularly limited thereto. In an embodiment, these peptides may significantly activate GLP-1 or additionally significantly activate the glucagon receptor and/or the GIP receptor, but the present disclosure is not particularly limited thereto.

In another embodiment, in General Formula 1,

Xaa2 may be glycine, alpha-methyl-glutamic acid, or Aib,

Xaa7 may be threonine,

Xaa10 may be tyrosine, cysteine, or valine,

Xaa12 may be lysine or isoleucine,

Xaa13 may be tyrosine, alanine, glutamine, or cysteine,

Xaa14 may be leucine, cysteine, or methionine,

Xaa15 may be cysteine, leucine, glutamic acid, or aspartic acid,

Xaa17 may be glutamine, arginine, isoleucine, cysteine, glutamic acid, or lysine, Xaa18 may be alanine, glutamine, arginine, or histidine, Xaa19 may be alanine, glutamine, valine, or cysteine, Xaa20 may be lysine, arginine, or glutamine, Xaa21 may be glutamic acid, glutamine, leucine, cysteine, or aspartic acid, Xaa23 may be isoleucine or valine, Xaa24 may be cysteine, alanine, glutamine, asparagine, glutamic acid, or aspartic acid, and Xaa27 may be leucine or lysine, but the present disclosure is not particularly limited thereto.

In an embodiment, in General Formula 1,

Xaa2 may be glycine, alpha-methyl-glutamic acid, or Aib,

Xaa7 may be threonine,

Xaa10 may be tyrosine, cysteine, or valine,

Xaa12 may be lysine or isoleucine,

Xaa13 may be tyrosine, alanine, or cysteine,

Xaa14 may be leucine or methionine,

Xaa15 may be cysteine or aspartic acid,

Xaa17 may be glutamine, arginine, isoleucine, cysteine, or lysine,

Xaa18 may be alanine, arginine, or histidine,

Xaa19 may be alanine, glutamine, or cysteine,

Xaa20 may be lysine or glutamine,

Xaa21 may be glutamic acid, cysteine, or aspartic acid,

Xaa23 may be valine,

Xaa24 may be alanine, glutamine, cysteine, asparagine, or aspartic acid, and

Xaa27 may be leucine or lysine, but the present disclosure is not particularly limited thereto.

In an embodiment, in General Formula 1,

Xaa2 may be alpha-methyl-glutamic acid or Aib,

Xaa7 may be threonine,

Xaa10 may be tyrosine or cysteine,

Xaa12 may be lysine or isoleucine,

Xaa13 may be tyrosine, alanine, or cysteine,

Xaa14 may be leucine or methionine,

Xaa15 may be cysteine or aspartic acid,

Xaa16 may be glutamic acid,

Xaa17 may be arginine, isoleucine, cysteine, or lysine,

Xaa18 may be alanine, arginine, or histidine,

Xaa19 may be alanine, glutamine, or cysteine,

Xaa20 may be lysine or glutamine,

Xaa21 may be glutamic acid or aspartic acid,

Xaa23 may be valine,

Xaa24 may be glutamine, asparagine, or aspartic acid,

Xaa27 may be leucine,

Xaa28 may be cysteine, alanine, asparagine, or aspartic acid.

In an embodiment, in General Formula 1,

Xaa1 may be histidine or 4-imidazoacetyl,

Xaa2 may be alpha-methyl-glutamic acid or Aib,

Xaa3 may be glutamine,

Xaa7 may be threonine,

Xaa10 may be tyrosine,

Xaa12 may be isoleucine,

Xaa13 may be alanine or cysteine,

Xaa14 may be methionine,

Xaa15 may be aspartic acid;

Xaa16 may be glutamic acid,

Xaa17 may be isoleucine or lysine,

Xaa18 may be alanine or histidine,

Xaa19 may be glutamine or cysteine,

Xaa20 may be lysine,

Xaa21 may be aspartic acid,

Xaa23 may be valine,

Xaa24 may be asparagine,

Xaa27 may be leucine,

Xaa28 may be alanine or asparagine,

Xaa29 may be glutamine or threonine, and

Xaa30 may be cysteine or lysine, or may be absent.

In an embodiment, in General Formula 1,

Xaa2 may be glycine, alpha-methyl-glutamic acid, or Aib,

Xaa3 may be glutamine,

Xaa7 may be threonine,

Xaa10 may be tyrosine, cysteine, or valine,

Xaa12 may be lysine,

Xaa13 may be tyrosine,

Xaa14 may be leucine,

Xaa15 may be aspartic acid,

Xaa16 may be glycine, glutamic acid, or serine,

Xaa17 may be glutamine, arginine, cysteine, or lysine,

Xaa18 may be alanine, arginine, or histidine,

Xaa19 may be alanine or glutamine,

Xaa20 may be lysine or glutamine,

Xaa21 may be glutamic acid, cysteine, or aspartic acid,

Xaa23 may be valine,

Xaa24 may be alanine, glutamine, or cysteine,

Xaa27 may be leucine or lysine, or

Xaa29 may be glycine, glutamine, threonine, or histidine, but the present disclosure is not particularly limited thereto.

These peptides have significant levels of activation of the GLP-1 receptor and the glucagon receptor, which are higher than the level of activation of the GIP receptor; have significant levels of activation of the GLP-1 receptor, the glucagon receptor, and the GIP receptor; or have significant levels of activation of the GLP-1 receptor and the GIP receptor, which are higher than the level of activation of the glucagon receptor, but the present disclosure is not particularly limited thereto.

Examples of such peptides include peptides that include or consist (essentially) of the amino acid sequence selected from the group consisting of SEQ ID NOs: 8, 9, 21 to 37, 39, 42, 43, 49 to 61, 64 to 83, 85, 86, 88, 89, 91 to 93, and 95 to 102, and are not particularly limited thereto.

In an embodiment, the peptide may include an amino acid sequence represented by General Formula 2 below:

```
                    (General Formula 2, SEQ ID NO: 104)
Xaa1-Xaa2-Gln-Gly-Thr-Phe-Thr-Ser-Asp-Xaa10-Ser-

Lys-Xaa13-Xaa14-Xaa15-Xaa16-Xaa17-Xaa18-Xaa19-

Xaa20-Xaa21-Phe-Xaa23-Xaa24-Trp-Leu-Leu-Xaa28-

Xaa29-Xaa30-Xaa31-Ser-Ser-Gly-Gln-Pro-Pro-Pro-

Ser-Xaa40
```

In General Formula 2,

Xaa1 may be 4-imidazoacetyl, histidine, or tyrosine,

Xaa2 may be glycine, alpha-methyl-glutamic acid, or Aib,

Xaa10 may be tyrosine, or cysteine,

Xaa13 may be alanine, glutamine, tyrosine, or cysteine,

Xaa14 may be leucine, methionine, or tyrosine,

Xaa15 may be aspartic acid, glutamic acid, or leucine,

Xaa16 may be glycine, glutamic acid, or serine,

Xaa17 may be glutamine, arginine, isoleucine, glutamic acid, cysteine, or lysine, Xaa18 may be alanine, glutamine, arginine, or histidine, Xaa19 may be alanine, glutamine, cysteine, or valine, Xaa20 may be lysine, glutamine, or arginine, Xaa21 may be cysteine, glutamic acid, glutamine, leucine, or aspartic acid, Xaa23 may be isoleucine or valine, Xaa24 may be cysteine, alanine, glutamine, asparagine, or glutamic acid, Xaa28 may be lysine, cysteine, asparagine, or aspartic acid, Xaa29 may be glycine, glutamine, cysteine, or histidine, Xaa30 may be cysteine, glycine, lysine, or histidine, Xaa31 may be proline or cysteine, and Xaa40 may be cysteine or absent.

In an embodiment, in General Formula 2,

Xaa13 may be alanine, tyrosine, or cysteine,

Xaa15 may be aspartic acid or glutamic acid,

Xaa17 may be glutamine, arginine, cysteine, or lysine,

Xaa18 may be alanine, arginine, or histidine,

Xaa21 may be cysteine, glutamic acid, glutamine, or aspartic acid,

Xaa23 may be isoleucine or valine,

Xaa24 may be cysteine, glutamine, or asparagine,

Xaa28 may be cysteine, asparagine, or aspartic acid,

Xaa29 may be glutamine, cysteine, or histidine, and

Xaa30 may be cysteine, lysine, or histidine.

Examples of such peptides include peptides that include or consist (essentially) of an amino acid sequence selected from the group consisting of SEQ ID NOs: 21, 22, 42, 43, 50, 64 to 77, and 95 to 102, or peptides that include or consist (essentially) of an amino acid sequence selected from the group consisting of SEQ ID NOs: 21, 22, 42, 43, 50, 64 to 77, and 96 to 102, but are not particularly limited thereto.

In an embodiment, the peptide may include the amino acid sequence of General Formula 3:

```
                (General Formula 3, SEQ ID NO: 105)
Xaa1-Xaa2-Gln-Gly-Thr-Phe-Thr-Ser-Asp-Tyr-Ser-Lys-

Xaa13-Leu-Asp-Glu-Xaa17-Xaa18-Xaa19-Lys-Xaa21-Phe-

Val-Xaa24-Trp-Leu-Leu-Xaa28-Xaa29-Xaa30-Xaa31-Ser-

Ser-Gly-Gln-Pro-Pro-Pro-Ser-Xaa40,
```

wherein, in General Formula 3,

Xaa1 may be histidine or tyrosine,

Xaa2 may be alpha-methyl-glutamic acid or Aib,

Xaa13 may be alanine, tyrosine, or cysteine,

Xaa17 may be arginine, cysteine, or lysine,

Xaa18 may be alanine or arginine,

Xaa19 may be alanine or cysteine,

Xaa21 may be glutamic acid or aspartic acid,

Xaa24 may be glutamine or asparagine,

Xaa28 may be cysteine or aspartic acid,

Xaa29 may be cysteine, histidine, or glutamine,

Xaa30 may be cysteine or histidine,

Xaa31 may be proline or cysteine, and

Xaa40 may be cysteine or absent.

Examples of such peptides include peptides that include or consist (essentially) of an amino acid sequence selected from the group consisting of SEQ ID NOs: 21, 22, 42, 43, 50, 64 to 71, 75 to 77, and 96 to 102, but are not particularly limited thereto.

R1 in General Formula 1 may be cysteine, GKKNDWKHNIT (SEQ ID NO: 106), CSSGQPPPS (SEQ ID NO: 109), GPSSGAPPPS (SEQ ID NO: 110), GPSSGAPPPSC (SEQ ID NO: 111), PSSGAPPPS (SEQ ID NO: 112), PSSGAPPPSG (SEQ ID NO: 113), PSSGAPPPSHG (SEQ ID NO: 114), PSSGAPPPSS (SEQ ID NO: 115), PSSGQPPPS (SEQ ID NO: 116), or PSSGQPPPSC (SEQ ID NO: 117), may be absent, and is not particularly limited thereto.

The triple agonist may include an intramolecular bridge (for example, a covalent bridge or a non-covalent bridge), and for example, may include a ring. In an embodiment, a ring may be formed by 16th and 20th amino acids in a glucagon analog or the triple agonist, but is not particularly limited thereto.

In an embodiment, the 16th amino acid and the 20th amino acid from the N-terminus in the General Formula may form a ring with each other.

Non-limiting examples of the ring may include a lactam bridge (or lactam ring).

In addition, the triple agonist may include all peptides that have been subjected to all modifications to include an amino acid, capable of forming a ring at a target position, to include a ring.

For example, amino acid pairs at positions 16 and 20 of a glucagon analog or triple agonist may each be substituted with glutamic acid or lysine capable of forming a ring, but the present disclosure is not limited thereto.

Such a ring may be formed between amino acid side chains in the glucagon analog or the triple agonist, and for example, a lactam ring may be formed between a side chain of lysine and a side chain of glutamic acid, but the ring is not particularly limited thereto.

In another embodiment, the peptide may include an amino acid sequence selected from the group consisting of SEQ ID NOs: 1 to 102.

In addition, the peptide may consist essentially of an amino acid sequence selected from the group consisting of SEQ ID NOs: 1 to 102, or the peptide may consist of an amino acid sequence selected from the group consisting of SEQ ID NOs: 1 to 102.

Even when the wording "peptide consisting of a specific sequence number" is used, as long as having the same activity as or corresponding activity to the peptide consisting of the corresponding sequence number, meaningless sequence addition before and after the amino acid sequence of the corresponding sequence number, or naturally-occurring mutants, or silent mutations thereof are not excluded, and even the case of the sequence addition or having mutants belongs to the scope of the present disclosure. That is, even in the case where there are differences in some sequences, when a certain level or higher of sequence identity exists and there is activity on the GIP receptor, all these cases belong to the scope of the present disclosure. Specifically, the peptide may include an amino acid sequence having an identity of 40%, 45%, 50%, %, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% or more with respect to of the amino acid sequences of SEQ ID NOs: 1 to 102.

The term "homology" or "identity" refers to the degree to which two given amino acid sequences or base sequences are related to each other and can be expressed as a percentage. Whether any two peptide sequences have homology, similarity or identity may be determined by, for example, known computer algorithms such as the "FASTA" program using default parameters shown in Pearson et al (1988) [Proc. Natl. Acad. Sci. USA 85]: 2444. In an embodiment, as performed by, for example, Needleman program of EMBOSS package (EMBOSS: The European Molecular Biology Open Software Suite, Rice et al., 2000, Trends Genet. 16: 276-277)(version 5.0.0 or later), Needleman-Wunsch algorism (Needleman and Wunsch, 1970, J. Mol. Biol. 48: 443-453) may be used therefor (GCG program package (Devereux, J., et al, Nucleic Acids Research 12: 387 (1984)), BLASTP, BLASTN, FASTA (Atschul, [S.] [F.,] [ET AL, J MOLEC BIOL 215]: 403 (1990); Guide to Huge Computers, Martin J. Bishop, [ED.,] Academic Press, San Diego, 1994, and [CARILLO ETA/.](1988) SIAM J Applied Math 48: 1073). For example, BLAST of the National Center for Biotechnology Information Database, or ClustalW may be used to determine homology, similarity, or identity.

Homology, similarity or identity of peptides may be determined by comparing sequence information using GAP computer program, for example, Needleman et al. (1970), J Mol Biol. 48: 443 as disclosed in Smith and Waterman, Adv. Appl. Math (1981) 2:482. In summary, the GAP program defines the homology, similarity or identity of peptides as a value obtained by the number similarly aligned symbols (that is, amino acids) by the total number of symbols in the shorter of the two sequences. The default parameters for the GAP program may include: (1) a binary comparison matrix (containing value 1 for identity and value 0 for non-identity) and weighted comparison matrix of Gribskov et al (1986) Nucl. Acids Res. 14: 6745 (or EMBOSS version of EDNAFULL (NCBI NUC4.4) substitution matrix) as disclosed in Schwartz and Dayhoff, eds., Atlas Of Protein Sequence And Structure, National Biomedical Research Foundation, pp. 353-358 (1979); (2) a penalty of 3.0 for each gap and an additional penalty of 0.10 for each symbol in each gap (or gap opening penalty of 10, gap extension penalty of 0.5); and (3) no penalty for end gaps. Thus, the term "homology" or "identity" used herein refers to a relevance between sequences.

In an embodiment, the glucagon analog or the triple agonist may be prepared by combining several methods for preparing various peptides.

Examples of analogs of glucagon prepared by a combination of these methods are peptides which are different from native-type glucagon in terms of an amino acid sequence, from which alpha-carbon of the N-terminal amino acid residue is removed, and which have activity on the glucagon receptor, the GLP-1 receptor, and the GiP receptor. However, the present disclosure is not limited thereto.

In addition, some amino acids of the triple agonist may be substituted with other amino acids or non-native-type compounds to avoid the recognition of activator degrading enzymes to increase the half-life in the body.

In an embodiment, the triple agonist may be a peptide of which the half-life in the body is increased by avoiding the recognition of degradation enzymes through substitution of the second amino acid sequence from among amino acid sequences. However, the substitution or change of an amino acid to avoid recognition of degradation enzymes in the body may be included herein without limitation.

The triple agonist may be synthesized by a method well known in the art, which varies depending on a length thereof. Examples of the method include synthesizing using an automatic peptide synthesizer or genetic engineering technology. Specifically, the peptides may be prepared by standard synthetic methods, recombinant expression systems, or any other methods in the art. Thus, peptides according to one aspect can be synthesized by using many methods including the following, but the methods are not limited to:

(a) synthesizing peptides stepwise or by fragment assembly by means of solid-phase or liquid-phase methods, and isolating and purifying the final peptide product; or (b) expressing a nucleic acid construct encoding the peptide in a host cell and recovering the expression product from the host cell culture; or (c) performing cell-free in vitro expression of a nucleic acid construct encoding a peptide and recovering the expression product; or obtaining a peptide fragment by any combination of (a), (b) and (c), then linking the fragments to obtain a peptide, and recovering the peptide.

In addition, the preparation of the peptide may include modification using an L-type or D-type amino acid, and/or a non-natural amino acid; and/or modification by changing a native-type sequence, for example, modification of side chain functional groups, or modification by intramolecular covalent linkages, for example, inter-side chain ring formation, methylation, acylation, ubiquitination, phosphorylation, aminohexanation, biotinylation, etc. In addition, the modifications include all substitutions with non-natural compounds.

Substituted or added amino acids used in the modification may use 20 amino acids commonly observed in human proteins as well as atypical or non-naturally occurring amino acids. Commercial sources of atypical amino acids may include, but are not limited to, Sigma-Aldrich, Chem Pep and Genzyme pharmaceuticals. For example, aminoisobutyric acid (Aib) may be prepared by Streker's amino acid synthesis in acetone, but the method thereof is not limited thereto. Peptides sequences containing such atypical or non-naturally occurring amino acids and typical peptide sequences may be synthesized and purchased from, but are limited to, commercialized peptide synthesis companies, such as American Peptide Company or Bachem in the US or Anygen in Korea.

In addition, the peptide may have an unmodified N-terminus and/or C-terminus. However, the following peptides are also be included in the category of peptides according to the above aspect: the N-terminus and/or C-terminus thereof may be chemically modified or protected from organic groups to protect from protein cleavage enzymes in vivo and increase stability; or amino acids are added to, for example, the ends of the peptides, etc. to carry out the modification. When the C-terminus is not modified, the end of the peptide has a free carboxyl group, but the present disclosure is not particularly limited thereto.

In particular, in the case of chemically synthesized peptides, since the N- and C-termini are charged, the N-terminus and/or C-terminus may be modified to remove these charges. For example, the N-terminus may be subjected to acetylation and/or the C-terminus may be subjected to amidation, but the present disclosure is not particularly limited thereto.

In an embodiment, the peptide may have the C-terminus thereof as being not modified or being amidated, but the present disclosure is not limited thereto.

In an embodiment, the peptide may be amidated at the C-terminus thereof.

The peptide includes a peptide itself, a salt thereof (for example, a pharmaceutically acceptable salt of the peptide) or a solvate thereof.

The type of salt is not particularly limited. However, it is preferable to be in a form that is safe and effective for subjects, for example mammals, but the present disclosure is not particularly limited thereto.

In addition, the peptide may be in any form that is pharmaceutically acceptable.

The term "pharmaceutically acceptable" used herein refers to an amount that is sufficient to exhibit a therapeutic effect and does not cause side effects, and may be easily determined by a person skilled in the art according to factors well known in the medical field, such as the type of disease, the age, weight, health, and sex of the patient, patient's sensitivity to drugs, route of administration, an administration method, the number of administrations, a treatment period, drugs used in combination or simultaneously.

In an embodiment, the peptide may be in the form of a pharmaceutically acceptable salt thereof. The salt include: conventional acid addition salts used in the pharmaceutical field, for example, in the field of lupus therapeutics, for example, salts derived from inorganic acids such as hydrochloric acid, hydrobromic acid, sulfuric acid, sulfamic acid, phosphoric acid or nitric acid; and salts derived from organic acids such as acetic acid, propionic acid, succinic acid, glycolic acid, stearic acid, citric acid, maleic acid, malonic acid, methanesulfonic acid, tartaric acid, malic acid, phenylacetic acid, glutamic acid, benzoic acid, salicylic acid, 2-acetoxybenzoic acid, fumaric acid, toluenesulfonic acid, oxalic acid, or trifluoroacetic acid. In addition, the salt may be a base addition salt such as ammonium, dimethylamine, monomethylamine, monoethylamine, or diethylamine. In addition, the salt includes a common metal salt form, for example, a salt derived from a metal such as lithium, sodium, potassium, magnesium, or calcium. The acid addition salt, the base addition salt, or the metal salt may be prepared according to a conventional method. Pharmaceutically acceptable salts and general methodologies for the preparation thereof are well known in the art. For example, the document [P. Stahl, et al. Handbook of Pharmaceutical Salts: Properties, Selection and Use, 2nd Revised Edition (Wiley-VCH, 2011)]; [S. M. Berge, et al., "Pharmaceutical Salts," Journal of Pharmaceutical Sciences, Vol. 66, No. 1, January 1977] may be referred to.

For the condensation of the protected amino acid or peptide, various activating reagents useful in peptide synthesis, for example, triphosphonium salt, tetramethyluronium salt, carbodiimide and the like may be used. Examples of triphosphonium salts include benzotriazol-1-yloxytris (pyrrolazino)phosphonium hexafluorophosphate (PyBOP), bromotris(pyrrolazino)phosphonium hexafluorophosphate (PyBroP), and 7-azabenzotriazol-1-yloxytris(pyrrolazino) phosphonium hexafluorophosphate (PyAOP), examples of tetramethyluronium salts include 2-(1H-benzotriazol-1-yl)-1,1,3,3-tetramethyluronium hexafluorophosphate (HBTU), 2-(7-azabenzotriazol-1-yl)-1,1,3,3-tetramethyluronium hexafluorophosphate (HATU), 2-(1H-benzotriazol-1-yl)-1,1,3,3-tetramethyluronium tetrafluoroborate (TBTU), 2-(5-norbornane-2,3-dicarboxyimide)-1,1,3,3-tetramethyluronium tetrafluoroborate (TNTU), and O—(N-succimidyl)-1,1,3,3-tetramethyluronium tetrafluoroborate (TSTU), and examples of carbodiimides include N,N'-dicyclohexylcarbodiimide (DCC), N,N'-diisopropylcarbodiimide (DIPCDI), and N-ethyl-N'-(3-dimethylaminopropyl)carbodiimide hydrochloride (EDCl·HCl). For condensation using these, racemization inhibitors [for example, N-hydroxy-5-norbornene-2,3-dicarboxylic acid imide (HONB), 1-hydroxybenzotriazole (HOBt), 1-hydroxy-7-azabenzotriazole (HOAt), 3,4-dihydro-3-hydroxy-4-oxo-1,2,3-benzotriazine (HOOBt), and ethyl 2-cyano-2-(hydroxyimino)acetate (Oxyma, etc.) may be added. The solvent used for the condensation may be appropriately selected from those known to be useful for peptide condensation reactions. For example, acid amides such as anhydrous or water-containing N, N-dimethylformamide, N, N-dimethylacetamide, N-methylpyrrolidone, etc. halogenated hydrocarbons such as methylene chloride, chloroform, etc.; alcohols such as fluoroethanol, phenol, etc.; sulfoxides such as dimethyl sulfoxide, etc.; tertiary amines such as pyridine, etc.; ethers such as dioxane, tetrahydrofuran, etc.; nitriles such as acetonitrile, propionitrile, etc.; esters such as methyl acetate, ethyl acetate, etc.; suitable mixtures thereof, may be used. The reaction temperature may be appropriately selected from a range known to be usable for the peptide bonding reaction, and is usually selected from the range of about −20° C. to 90° C. Activated amino acid derivatives may be usually used in excess of 1.5 fold to 6 fold. Regarding the solid phase synthesis, when a test using a ninhydrin reaction indicates that the condensation is insufficient, sufficient condensation may be performed by repeating the condensation reaction without removing the protecting group. When condensation is still insufficient even after repeating the reaction, since the unreacted amino acid can be acetylated with an acid anhydride, acetylimidazole or the like, the influence thereof on the subsequent reaction may be avoided.

Examples of protecting groups for the amino group of the starting amino acid are benzyloxycarbonyl (Z), tert-butoxycarbonyl (Boc), tert-pentyloxycarbonyl, isobornyloxycarbonyl, 4-methoxybenzyloxy Carbonyl, 2-chlorobenzyloxycarbonyl (Cl—Z), 2-bromobenzyloxycarbonyl (Br—Z), adamantyloxycarbonyl, trifluoroacetyl, phthaloyl, formyl, 2-nitrophenylsulfenyl, diphenylphosphinothioyl, 9-fluorenylmethyloxycarbonyl (Fmoc), and trityl.

Examples of carboxyl-protecting groups for starting amino acids include, in addition to $C_{1-6}$ alkyl groups, $C_{3-10}$ cycloalkyl groups, and $C_{7-14}$ aralkyl groups described above, aryl, 2-adamantyl, 4-nitrobenzyl, 4-methoxybenzyl, 4-chlorobenzyl, fenacil, benzyloxycarbonylhydrazide, tert-butoxycarbonylhydrazide, and trityl hydrazide.

The hydroxyl groups of serine or threonine may be protected by, for example, esterification or etherification. Examples of groups suitable for esterification include groups derived from lower ($C_{2-4}$) alkanoyl groups such as acetyl groups, aroyl groups such as benzoyl groups, organic acids and the like. Additionally, examples of groups suitable for etherification include benzyl, tetrahydropyranyl, tert-butyl ($Bu^t$), trityl (Trt), and the like.

Examples of protecting groups for the phenolic hydroxyl group of tyrosine include Bzl, 2,6-dichlorobenzyl, 2-nitrobenzyl, Br-Z, tert-butyl, and the like.

Examples of protecting groups for imidazole of histidine include p-toluenesulfonyl (Tos), 4-methoxy-2,3,6-trimethylbenzenesulfonyl (Mtr), dinitrophenyl (DNP), benzyloxymethyl (Bom), tert-butoxymethyl (Bum), Boc, Trt, Fmoc, and the like.

Examples of protecting groups for the guanidino group of arginine include Tos, Z, 4-methoxy-2,3,6-trimethylbenzenesulfonyl (Mtr), p-methoxybenzenesulfonyl (MBS), 2,2,5,7,8-pentamethylchroman-6-sulfonyl (Pmc), mesitylene-2-sulfonyl (Mts), 2,2,4,6,7-pentamethyldihydrobenzofuran-5-sulfonylphonyl (Pbf), Boc, Z, $NO_2$, and the like.

Examples of protecting groups for side chain amino groups of lysine include Z, Cl—Z, trifluoroacetyl, Boc, Fmoc, Trt, Mtr, 4,4-dimethyl-2,6-dioxocyclohexylidenyl (Dde), and the like.

Examples of protecting groups for indolyl of tryptophan include formyl (For), Z, Boc, Mts, Mtr, and the like.

Examples of protecting groups for asparagine and glutamine include Trt, xantyl (Xan), 4,4'-dimethoxybenzhydryl (Mbh), 2,4,6-trimethoxybenzyl (Tmob), and the like.

Examples of activated carboxyl groups in the starting material include corresponding acid anhydrides, azides, active esters [esters with alcohols (for example, pentachlorophenol, 2,4,5-trichlorophenol, 2,4-dinitrophenol, cyanomethyl alcohol, paranitrophenol, HONB, N-hydroxysuccimide, 1-hydroxybenzotriazole (HOBt), 1-hydroxy-7-azabenzotriazole (HOAt))], etc. Examples of activated amino groups in the starting material include a corresponding phosphorus amide.

Examples of methods of removing the protecting group include: a catalytic reduction in a hydrogen stream in the presence of a catalyst such as Pd-black or Pd-carbon; an acid treatment using anhydrous hydrogen fluoride, methanesulfonic acid, trifluoromethanesulfonic acid, trifluoroacetic acid (TFA), trimethylsilyl bromide (TMSBr), trimethylsilyl trifluoromethanesulfonate, tetrafluoroboric acid, tris(trifluoro) boric acid, boron tribromide, or a mixture solution thereof; a base treatment using diisopropylethylamine, triethylamine, piperidine, piperazine, etc.; and a reduction using sodium in liquid ammonia; and the like. The removal reaction by acid treatment described above is generally carried out at a temperature of −20° C. to 40° C., and the acid treatment may be efficiently performed by adding anisole, phenol, thioanisole, metacresol, and paracresol; or a cation scavenger such as dimethylsulfide, 1,4-butanedithiol, 1,2-ethanedithiol, triisopropylsilane, and the like. In addition, the 2,4-dinitrophenyl group used as the protecting group of the imidazole of histidine is removed by thiophenol treatment; and the formyl group used as a protecting group for the indole of tryptophan is removed by deprotection performed by not only an acid treatment in the presence of 1,2-ethanedithiol and 1,4-butanedithiol, but also an alkali treatment with diluted sodium hydroxide and diluted ammonia.

Protection of a functional group that should not be involved in the reaction between the starting material and the protecting group, the removal of the protecting group, the activation of a functional group involved in the reaction, and the like could be appropriately selected from known protecting groups and known means.

For the peptides described herein, the left end is the N-terminus (amino terminus) and the right end is the C-terminus (carboxyl terminus), according to conventional peptide markings. The C-terminus of the peptide may be one of amide (—$CONH_2$), a carboxyl group (—COOH), carboxylate (—COO—), alkylamide (—CONHR' where R' is alkyl), and ester (—COOR' where R' is an alkyl or an aryl).

In the method for preparing an amide of a peptide, it is formed by solid phase synthesis using a resin for amide synthesis, or the α-carboxyl group of a carboxy terminal amino acid is amidated, and a peptide in which the peptide chain is elongated toward the amino group in a desired chain length. and then, the protecting group for the N-terminal a-amino group of the peptide chain only is removed and a peptide in which only the protecting group for the C-terminal carboxyl group is removed from the peptide chain, are prepared, and these two peptides are condensed in the mixed solvents described above. Regarding the details of the condensation reaction, the same as described above applies herein. After the protected peptide obtained by condensation is purified, all protecting groups may be removed by the method described above to obtain the desired peptide. By purifying this peptide using various publicly known means for purification of the major fraction and freeze-drying, the desired amide of the peptide may be prepared.

In an embodiment, the peptide may be in the form of a solvate thereof. The term "solvate" used herein refers to a case where the peptide or a salt thereof forms a complex with solvent molecules.

In an embodiment, the composition may be a pharmaceutical composition for preventing or treating lupus-associated disease, including: a pharmaceutically acceptable excipient; and a peptide including an amino acid sequence of any one of SEQ ID NOs: 1 to 102 in a pharmaceutically effective amount.

In an embodiment, the peptide may be in the form of a long-acting conjugate. The conjugate exhibits activity equal to or higher than that of native-type ligand (that is, native-type glucagon, native-type GLP-1 and native-type GIP), and at the same time, increased potency persistence, compared to a native-type ligand or a derivative thereof to which a carrier (or a biocompatible material) is not bound. The term "long-acting conjugate" used herein refers to a conjugate with increased durability compared to native-type ligand, to which a biocompatible material is not bound, or derivatives thereof. Therefore, the conjugate may be used interchangeably with "long-acting glucagon/GLP-1/GIP triple agonist conjugate," "long-acting glucagon/GLP-1/GIP triple agonist," "long-acting glucagon/GLP-1/GIP conjugate," "long-acting GCG/GLP-1/GIP conjugate," "triple agonist conjugate," "long-acting conjugate of triple agonist," "long-acting conjugate," or "conjugate." Such conjugates include not only the above-described forms, but also forms encapsulated in biodegradable nanoparticles.

The conjugate may be an isolated conjugate.

The conjugate may be a non-naturally occurring conjugate.

In an embodiment, the peptide may be in the form of a conjugate in which a biocompatible material, which increases the half-life in vivo, is bound. Therefore, the pharmaceutical composition may include a conjugate in which the glucagon/GLP-1/GIP triple agonist and a biocompatible material that increases half-life in vivo are bound to each other. The biocompatible material may be used interchangeably with a carrier.

In an embodiment, the long-acting conjugate may be represented by Formula 1:

X-L-F Formula 1 where X is a glucagon/GLP-1/GIP triple agonist,

L is a linker;

F is a biocompatible material that increases the half-life of X in vivo, and

- represents a bonding linkage between X and L and a bonding linkage between L and F.

The glucagon/GLP-1/GIP triple agonist in Formula 1 is the same as described above.

L in Formula 1 may be La, where a is 0 or a natural number, wherein, when a is 2 or more, and respective L may each independently from each other.

The biocompatible material may be bonded to the glucagon/GLP-1/GIP triple agonist through a covalent chemical bond or a non-covalent chemical bond, and may be bound to each other through a linker (L) by a covalent chemical bond, a non-covalent chemical bond, or a combination thereof. In an embodiment, - may represent a covalent bonding linkage between X and L or a covalent bonding linkage between L and F.

One or more amino acid side chains within the glucagon/GLP-1/GIP triple agonist may be conjugated to these biocompatible materials to increase solubility and/or half-life in vivo and/or increase bioavailability. Such modifications may reduce clearance of therapeutic proteins and peptides. The biocompatible materials may be water soluble (amphiphilic or hydrophilic) and/or non-toxic and/or pharmaceutically acceptable.

The biocompatible material may be selected from the group consisting of high-molecular-weight polymers, fatty acids, cholesterol, albumin and fragments thereof, albumin binding substances, polymers of repeating units of specific amino acid sequences, antibodies, antibody fragments, FcRn binding substances, in vivo connective tissues, nucleotides, fibronectin, transferrin, saccharides, heparin, and elastin, but the present disclosure is not particularly limited thereto.

Examples of the polymers include a high-molecular-weight polymer selected from the group consisting of polyethylene glycol (PEG), polypropylene glycol, ethylene glycol-propylene glycol copolymers, polyoxyethylated polyols, polyvinyl alcohol, polysaccharides, polyvinyl ethyl ether, biodegradable polymers, lipid polymers, chitin, hyaluronic acid, oligonucleotides, and combinations thereof, and the polysaccharides may be dextran, but the present disclosure is not particularly limited thereto.

The polyethylene glycol is a term encompassing all types of ethylene glycol homopolymers, PEG copolymers, and monomethyl-substituted PEG polymers (mPEG), but the present disclosure is not particularly limited thereto.

The fatty acid may have a binding force with albumin in vivo, but the present disclosure is not particularly limited thereto.

The biocompatible material includes, but is not limited to, poly-amino acids such as poly-lysine, poly-aspartic acid and poly-glutamic acid.

In the case of the elastin, human tropoelastin, which is a water-soluble prewncursor, may be used, and a polymer of some sequences or some repeating units thereof may be used. For example, all elastin-like polypeptides may be included. However, the present disclosure is not particularly limited thereto.

In an embodiment, the biocompatible material may be an FcRn binding material. For example, the FcRn binding material may be an immunoglobulin Fc region, for example, an IgG Fc region, or a non-glycosylated IgG4 Fc region, but the present disclosure is not particularly limited thereto.

The term "immunoglobulin Fc region" used herein refers to a region including constant region 2(CH2) of the heavy chain and/or constant region 3 (CH3) of the heavy chain, excluding the variable region of the heavy chain and the variable region of the light chain of immunoglobulin. The immunoglobulin Fc region may be one component constituting a moiety of a conjugate according to one aspect.

Such an immunoglobulin Fc region may include a hinge portion in a constant region of the heavy chain, but the present disclosure is not limited thereto.

In an embodiment, an immunoglobulin Fc region may include a specific hinge sequence at the N-terminus thereof.

The term "hinge sequence" refers to a site located in the heavy chain to form a dimer of an immunoglobulin Fc fragment through an inter disulfide bond.

In an embodiment, the hinge sequence may be mutated such that a part of the hinge sequence having the following amino acid sequence is deleted to leave only one cysteine residue:

```
                                        (SEQ ID NO: 119)
Glu-Ser-Lys-Tyr-Gly-Pro-Pro-Cys-Pro-Ser-Cys-Pro.
```

The hinge sequence may include a case where only one cysteine residue remains by deletion of the 8th or 11th cysteine residue of the hinge sequence of SEQ ID NO: 119. A hinge sequence according to an embodiment may consist of 3 to 12 amino acids including only one cysteine residue, but the present disclosure is not limited thereto. For example, the hinge sequence according to an embodiment may have the following sequence: Glu-Ser-Lys-Tyr-Gly-Pro-Pro-Pro-Ser-Cys-Pro(SEQ ID NO: 120), Glu-Ser-Lys-Tyr-Gly-Pro-Pro-Cys-Pro-Ser-Pro(SEQ ID NO: 121), Glu-Ser-Lys-Tyr-Gly-Pro-Pro-Cys-Pro-Ser(SEQ ID NO: 122), Glu-Ser-Lys-Tyr-Gly-Pro-Pro-Cys-Pro-Pro(SEQ ID NO: 123), Lys-Tyr-Gly-Pro-Pro-Cys-Pro-Ser(SEQ ID NO: 124), Glu-Ser-Lys-Tyr-Gly-Pro-Pro-Cys(SEQ ID NO: 125), Glu-Lys-Tyr-Gly-Pro-Pro-Cys(SEQ ID NO: 126), Glu-Ser-Pro-Ser-Cys-Pro(SEQ ID NO: 127), Glu-Pro-Ser-Cys-Pro(SEQ ID NO: 128), Pro-Ser-Cys-Pro(SEQ ID NO: 129), Glu-Ser-Lys-Tyr-Gly-Pro-Pro-Ser-Cys-Pro(SEQ ID NO: 130), Lys-Tyr-Gly-Pro-Pro-Pro-Ser-Cys-Pro(SEQ ID NO: 131), Glu-Ser-Lys-Tyr-Gly-Pro-Ser-Cys-Pro(SEQ ID NO: 132), Glu-Ser-Lys-Tyr-Gly-Pro-Pro-Cys(SEQ ID NO: 133), Lys-Tyr-Gly-Pro-Pro-Cys-Pro(SEQ ID NO: 134), Glu-Ser-Lys-Pro-Ser-Cys-Pro(SEQ ID NO: 135), Glu-Ser-Pro-Ser-Cys-Pro (SEQ ID NO: 136), Glu-Pro-Ser-Cys(SEQ ID NO: 137), or Ser-Cys-Pro(SEQ ID NO: 138).

For example, the hinge sequence may include an amino acid sequence of SEQ ID NO: 129 (Pro-Ser-Cys-Pro) or SEQ ID NO: 138 (Ser-Cys-Pro), but is not limited thereto.

The immunoglobulin Fc region according to an embodiment may have a form in which two molecules of the immunoglobulin Fc chain form a dimer due to the presence of a hinge sequence. In addition, in the conjugate of Formula 1 according to an embodiment, one end of the linker may be linked to one chain of the immunoglobulin Fc region of the dimer, but the present disclosure is not limited thereto.

The term "N-terminus" used herein refers to the amino terminus of a protein or a polypeptide, may include the most terminal of the amino terminus, or up to 1, 2, 3, 4, 5, 6, 7, 8, 9, 10 or more amino acids from the most terminal. The immunoglobulin Fc fragment of the present disclosure may include a hinge sequence at the N-terminus, but is not limited thereto.

In addition, as long as having substantially the same as the native-type or improved effect compared thereto, the immunoglobulin Fc region may be an extended Fc region including some or all constant region 1 (CH1) of the heavy chain and/or constant region 1 (CL1) of the light chain, except for the variable region of the heavy chain and the variable region of the light chain. In addition, the immunoglobulin Fc region may be a region from which a relatively long amino acid sequence corresponding to CH2 and/or CH3 is removed.

For example, the immunoglobulin Fc region may be selected from the group consisting of: (a) a CH1 domain, a CH2 domain, a CH3 domain, and a CH4 domain; (b) a CH1 domain and a CH2 domain; (c) a CH1 domain and a CH3 domain; (d) a CH2 domain and a CH3 domain; (e) a combination of one or more of the CH1 domain, the CH2 domain, the CH3 domain, and the CH4 domain with an immunoglobulin hinge region or a portion of a hinge region; and (f) a dimer between each domain of the heavy chain constant region and the light chain constant region, but the present disclosure is not limited thereto.

The immunoglobulin Fc region may be in a dimeric form, and one molecule of the glucagon/GLP-1/GIP triple agonist may be covalently linked to one Fc region of the dimer form, wherein the immunoglobulin Fc and the glucagon/GLP-1/GIP triple agonist may be linked to each other by a non-peptide polymer. In an embodiment, two molecules of glucagon/GLP-1/GIP triple agonist may bind symmetrically to one Fc region in the dimeric form. In this case, the immunoglobulin Fc and the glucagon/GLP-1/GIP triple agonist may be linked to each other by a non-peptide linker. However, the present disclosure is not limited to the embodiments described above.

In addition, the immunoglobulin Fc region includes, in addition to native-type amino acid sequences, sequence derivatives thereof. The term “amino acid sequence derivative” used herein refers to a case where one or more amino acid residues in a natural amino acid sequence have different sequences due to deletion, insertion, non-conservative or conservative substitution, or a combination thereof.

For example, in the case of IgG Fc, 214th to 238th, 297th to 299th, 318th to 322nd, or 327th to 331st amino acid residues, which are known to be important for binding, may be used as suitable sites for modification. In addition, various derivatives may be obtained by removing a site capable of forming a disulfide bond, removing some amino acids at the N-terminus of native-type Fc, or adding a methionine residue to the N-terminus of native-type Fc. In addition, in order to eliminate the effector function, a complement binding site, for example, a C1q binding site, may be removed, and an antibody dependent cell mediated cytotoxicity (ADCC) site may be removed. Techniques for preparing sequence derivatives of the immunoglobulin Fc region are disclosed in International Patent Publication No. WO 97/34631 and International Patent Publication No. 96/32478.

Amino acid exchanges in proteins and peptides that do not entirely change the activity of the molecule are known in the art (H. Neurath, R. L. Hill, The Proteins, Academic Press, New York, 1979). The most commonly occurring exchanges are exchanges between amino acid residues Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly. In some cases, modification may be made by phosphorylation, sulfation, acrylation, glycosylation, methylation, farnesylation, acetylation, and amidation.

The Fc derivatives may exhibit biological activity equivalent to that of the Fc region, and of which structural stability of the Fc region against heat and pH may be increased.

In addition, such an Fc region may be obtained from a native-type isolated in vivo from human and an animal such as cow, goat, pig, mouse, rabbit, hamster, rat, or guinea pig, or may be recombinant or a derivative thereof, obtained from transformed animal cells or microorganisms. In this regard, a method of obtaining from the native-type may be a method in which whole immunoglobulin is isolated from a living body of a human or animal, and then treated with a proteolytic enzyme. When treated with papain, Fab and Fc are used for cleavage, and when treated with pepsin, pF'c and $F(ab)_2$ are used for cleavage. Fc or pF'c may be separated using size-exclusion chromatography or the like. In a more specific embodiment, the human-derived Fc region may be a recombinant immunoglobulin Fc region obtained from a microorganism.

In addition, the immunoglobulin Fc region may be in the form of a native-type glycan, a glycan which is increased compared to a native-type glycan, a glycan which is reduced compared to a native-type glycan, or a glycan-free form. For the increase or decrease in the immunoglobulin Fc glycan, conventional methods such as chemical methods, enzymatic methods, and genetic engineering methods using microorganisms may be used. In this regard, the immunoglobulin Fc region that is deglycosylated from Fc, has significantly reduced binding ability to complement (c1q), and the antibody-dependent cytotoxicity or complement-dependent cytotoxicity of the immunoglobulin Fc region is reduced or eliminated. Accordingly, unnecessary immune responses may not be caused in vivo. In this respect, a form that is more suitable for its original purpose as a drug carrier, may be an immunoglobulin Fc region that is deglycosylated or aglycosylated.

“Deglycosylation” used herein refers to an Fc region from which glucoses are removed by an enzyme, and “aglycosylation” used herein refers to an Fc region that is produced in a prokaryotic animal, for example, *Escherichia coli* and thus is not glycosylated.

In addition, the immunoglobulin Fc region may be an Fc region derived from IgG, IgA, IgD, IgE, or IgM, a combination thereof, or a hybrid thereof. In an embodiment, the immunoglobulin Fc region may be derived from IgG or IgM, which is most abundant in human blood. In an embodiment, and in a more specific embodiment, the immunoglobulin Fc region may be derived from IgG that is known to improve the half-life of ligand binding proteins. In an embodiment, the immunoglobulin Fc region may be an IgG4 Fc region, and in an embodiment, the immunoglobulin Fc region may be an aglycosylated Fc region derived from human IgG4, but the present disclosure is not limited thereto.

The term “combination” refers to a case where, when dimers or multimers are formed, a polypeptide encoding single-chain immunoglobulin Fc region of a same origin form bonds with a single-chain polypeptide of a different origin. That is, dimers or multimers may be prepared from two or more fragments selected from the group consisting of Fc fragments of IgG Fc, IgA Fc, IgM Fc, IgD Fc, and IgE.

The glucagon/GLP-1/GIP triple agonist may be linked to a biocompatible material through a linker.

The linker may be a peptide linker or a non-peptide linker.

When the linker is a peptide linker, the linker may include at least one amino acid, for example, 1 amino acid to 1,000 amino acids, but embodiments are not particularly limited thereto. The peptide linker may include Gly, Asn, and Ser residues, and may also include neutral amino acids such as Thr and Ala. For the linkage between the biocompatible material and the GIP derivative, various known peptide linkers may be used. In addition, the number of copies “n” may be adjusted in consideration of linker optimization to achieve proper separation between functional moieties or to maintain essential inter-moiety interactions. Other soluble linkers are known in the art, and for example, a GS linker, in which not only a polar amino acid residue is added to improve water solubility, but also amino acid residues, such as T and A, are added to maintain flexibility may be used. Therefore, in an embodiment, the linker may be a flexible linker including G, S, and/or T residues. The linker may have a general formula selected from (GpSs)n and (SpGs)n, wherein, independently, p may be an integer of 1 to 10, s may be an integer of 0 to 10, the sum of p and S may be an integer of 20 or less, and n may be an integer of 1 to 20. In detail, the linker may have, for example, a general formula of (GGGGS)n (SEQ ID NO: 139), (SGGGG)n (SEQ ID NO: 140), (SRSSG)n (SEQ ID NO: 141), (SGSSC)n (SEQ ID NO: 142), (GKSSGSGSESKS)n (SEQ ID NO: 143), (RPPPPC)n (SEQ ID NO: 144), (SSPPPPC)n (SEQ ID NO: 145), (GSTSGSGKSSEGKG)n (SEQ ID NO: 146), (GSTSGSGKSSEGSGSTKG)n (SEQ ID NO: 147), (GSTSGSGKPGSGEGSTKG)n (SEQ ID NO: 148), or (EGKSSGSGSESKEF)n (SEQ ID NO: 149), wherein n may be an integer of 1 to 20 or an integer of 1 to 10.

The "non-peptide linker" includes a biocompatible polymer to which two or more repeating units are bonded. The repeating units are linked to each other through any covalent bond other than a peptide bond. The non-peptide linker may be one component constituting the moiety of the conjugate.

The "non-peptide linker" may be used interchangeably with the "non-peptide polymer."

In an embodiment, in the conjugate, a biocompatible material and the glucagon/GLP-1/GIP triple agonist may be covalently linked to each other via a non-peptide linker containing reactive groups at both ends thereof capable of binding to the biocompatible material, for example, an immunoglobulin Fc region, and the glucagon/GLP-1/GIP triple agonist.

Specifically, the non-peptide linker may be selected from the group consisting of a fatty acid, a saccharide, a high-molecular-weight polymer, a low-molecular weight compound, a nucleotide, and a combination thereof.

Although not particularly limited thereto, the non-peptide linker may be selected from the group consisting of biodegradable polymers such as polyethylene glycol, polypropylene glycol, an ethylene glycol-propylene glycol copolymer, polyoxyethylated polyol, polyvinyl alcohol, polysaccharide, polyvinyl ethyl ether, polylactic acid (PLA), polylactic-glycolic acid (PLGA); and lipid polymers, chitins, hyaluronic acid, oligonucleotides, and combinations thereof. The polysaccharide may be dextran, but is not limited thereto.

In an embodiment, the non-peptide polymer may be polyethylene glycol, but is not limited thereto. Therefore, L in Formula 1 may be a linker containing an ethylene glycol repeating unit.

For example, the linker may be polyethylene glycol (PEG) represented by Formula 2, but is not limited thereto:

Formula 2

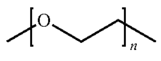

where n=10 to 2400, n=10 to 480, or n=50 to 250, but n is not limited thereto.

In the long-acting conjugate, the PEG moiety may include not only a —$(CH_2CH_2O)$n- structure but also an oxygen atom intervening between a linking element and the —$(CH_2CH_2O)$n-, but the present disclosure is not limited thereto.

The polyethylene glycol is a term encompassing all types of ethylene glycol homopolymers, PEG copolymers, and monomethyl-substituted PEG polymers (mPEG), but the present disclosure is not particularly limited thereto.

In addition, derivatives thereof already known in the art and derivatives that could be easily prepared at the level of skill in the art are also included in the scope of the present disclosure.

The non-peptide linker may be any linker that is a polymer resistant to in vivo proteolytic enzymes. The formula weight of the non-peptide polymer may be in the range of 1 kDa to 1000 kDa, specifically in the range of 1 kDa to 100 kDa, more specifically in the range of 1 kDa to 20 kDa, but is not limited thereto. In addition, for use as the non-peptide linker, not only one type of polymer but also a combination of different types of polymers may be used. In an embodiment, the formula weight of the ethylene glycol repeating unit in L may be in the range of 1 kDa to 100 kDa, for example, in the range of 1 kDa to 20 kDa.

In an embodiment, oppose ends of the non-peptide linker may bind to a biocompatible material, for example, an amine or thiol group of an immunoglobulin Fc region and an amine or thiol group of a glucagon/GLP-1/GIP triple agonist, respectively.

For example, the non-peptide polymer may include a reactive group capable of binding to a biocompatible material (for example, an immunoglobulin Fc region) and a glucagon/GLP-1/GIP triple agonist at oppose ends thereof, respectively, for example, a reactive group capable of binding to an amine group located at the N-terminus or lysine, or a thiol group of cysteine of a glucagon/GLP-1/GIP triple agonist or a biocompatible material (for example, an immunoglobulin Fc region).

In an embodiment, the reactive group of the non-peptide polymer, which is capable of binding to a biocompatible material, such as an immunoglobulin Fc region, and a glucagon/GLP-1/GIP triple agonist may be selected from the group consisting of an aldehyde group, a maleimide group, and a succinimide derivative. However, the present disclosure is not limited thereto. In the above, examples of the aldehyde group include propione aldehyde group or butyl aldehyde group, but are not limited thereto. The succinimide derivatives include succinimidyl valerate, succinimidyl methylbutanoate, succinimidyl methylpropionate, succinimidyl butanoate, succinimidyl propionate, N-hydroxysuccinimide, hydroxy succinimidyl, succinimidyl carboxymethyl, or succinimidyl carbonate, but are not limited thereto.

In addition, end products produced by reductive alkylation by aldehyde linkages are much more stable than those linked by amide linkages. The aldehyde reactive group reacts selectively at the N-terminus at low pH, and may form a covalent bond with a lysine residue at high pH, for example, pH 9.0.

In addition, the reactive groups at oppose ends of the non-peptide linker may be the same or different from each other, and for example, a maleimide group may be located at one end and an aldehyde group, a propionaldehyde group, or a butyl aldehyde group may be located at the other end. However, the present disclosure is not limited thereto as long as a biocompatible material, for example, an immunoglobulin Fc region, and a glucagon/GLP-1/GIP triple agonist could be respectively bound to ends of the non-peptide linker. For example, one end of the non-peptide linker may include a maleimide group as a reactive group, and the other end thereof may include an aldehyde group, a propione aldehyde group, or a butyl aldehyde group.

When the non-peptide polymer is a polyethylene glycol having hydroxyl groups at oppose ends, long-acting conjugates may be prepared by activating the hydroxy groups using various reactive groups by a known chemical reaction, or by using a polyethylene glycol having modified reactive groups, which is commercially available.

In an embodiment, the non-peptide polymer may be linked to a cysteine residue of the glucagon/GLP-1/GIP triple agonist, for example, to a —SH group of cysteine, but the present disclosure is not limited thereto.

When maleimide-PEG-aldehyde is used, the maleimide group is linked to the —SH group of the glucagon/GLP-1/GIP triple agonist through a thioether bond, and the aldehyde group may be linked to the biocompatible material, for example, to the $NH_2$ group of the immunoglobulin Fc through a reductive alkylation reaction. However, this method is only an example.

In addition, in the conjugate, the reactive group of the non-peptide polymer may be linked to —$NH_2$ located at the N-terminus of the immunoglobulin Fc region, but this structure is an example only.

In an embodiment, the long-acting conjugate may be represented by Formula 1:

X-L-F Formula 1 wherein X is a peptide including an amino acid sequence of any one of SEQ ID NOs: 1 to 102;

L is a linker containing an ethylene glycol repeating unit,

F is an immunoglobulin Fc region, and

- represents a covalent bonding linkage between X and L and a covalent bonding linkage between L and F.

In an embodiment, the peptide may include an amino acid sequence selected from the group consisting of SEQ ID NOs: 21, 22, 42, 43, 50, 64, 66, 67, 70, 71, 76, 77, 96, 97 and 100.

In an embodiment, the peptide may include an amino acid sequence selected from the group consisting of SEQ ID NOs: 21, 22, 42, 43, 50, 66, 67, 77, 96, 97, and 100.

In an embodiment, the peptide may include an amino acid sequence selected from the group consisting of SEQ ID NOs: 21, 22, 42, 43, 50, 77, and 96.

The glucagon/GLP-1/GIP triple agonist or a conjugate thereof was confirmed to improve edema and restore skin lesions, as well as reduce the weight and size of enlarged spleen due to inflammatory response in a lupus disease model mouse. As such, it was confirmed that the triple agonist with activity on glucagon, GLP-1, and GIP, as well as a long-acting conjugate thereof, can be used for the prevention or treatment of lupus-associated disease.

The glucagon/GLP-1/GIP triple agonist or a conjugate thereof has activity on the glucagon receptor, the GLP-1 receptor, and the GIP receptor, and the activity on the glucagon receptor thereof may be higher than the activity on the GLP-1 receptor or the GIP receptor. For example, the peptides represented by SEQ ID NO: 21, 22, 42, 43, 66, 70, 96, and 97 have very high activity on the glucagon receptor. Glucagon targets the liver. Accordingly, when the activity on the glucagon receptor is high, glucagon may be more secreted and thus, the effect on the liver may be increased. However, since many long-acting conjugates of triple agonists are present in the blood upon administration, their effects are not limited thereto and may be suitable for controlling systemic inflammatory diseases such as lupus.

The term "prevention" used herein refers to any action that inhibits or delays the onset of lupus-associated disease by administering the composition.

The term "treatment" used herein refers to any action that alleviates the symptoms of lupus-associated disease by administration of the composition.

"Lupus" is an autoimmune disease. Inflammation appears throughout the body as the white blood cells, immune cells, of our body attack our body and tissues are damaged. Lupus, meaning "red rash," is a disease that occurs not only on the skin but also throughout the body, called systemic lupus erythematosus, or lupus for short. This disease is characterized by the fact that 90% of patients are women and it occurs in the reproductive age group of 20 to 50 years old. An autoimmune disease may cause inflammation anywhere in the body, and symptoms appear in various ways according thereto, and also, the diagnosis thereof is not easy because the symptoms change over time.

Autoimmune reactions can cause inflammation anywhere in the body and produce various symptoms depending on where the inflammation occurs. As a common example, inflammation in the joints may cause joint pain, inflammation throughout the body may cause fever, and inflammation in the skin may cause a rash. Inflammation in the kidneys may lead to proteinuria, while inflammation of the membrane surrounding the lungs and heart may cause chest pain. Other possible symptoms include photosensitivity, hair loss, blood cell abnormalities, Raynaud's phenomenon, seizures, and mouth ulcers.

"Lupus" generally refers to systemic lupus erythematosus (SLE). The SLE is also called systemic lupus erythematosus or S.L.E., and is a chronic inflammatory autoimmune disease and a systemic disease that affects various organs of the body, such as connective tissue, skin, joints, blood, and kidneys. SLE may not always cause symptoms throughout the entire body and may only cause mild symptoms in some parts of the body. Lupus is also be classified as a type of small vessel vasculitis. However, unlike vasculitis, which only affects a specific area, for example, blood vessels, lupus targets all tissues in the body. Therefore, drugs that are effective in treating vasculitis may not necessarily be effective in treating lupus and vice versa.

"Lupus-associated diseases" include SLE or systemic lupus erythematosus and refer to diseases or symptoms that are associated with or co-occur with lupus. The lupus-associated disease may cause symptoms on one or more organs of the lungs, heart, muscles, and joints. The lupus-associated disease may be accompanied by skin lesions. Thus, the lupus-associated disease diagnosed based on a skin lesion score. A pharmaceutical composition according to an embodiment may reduce skin lesions in patients, thus effectively treating lupus-associated diseases.

Examples of lupus-associated diseases include systemic lupus erythematosus (SLE), discoid lupus erythematosus (DLE), drug-induced lupus, and neonatal lupus.

DLE, also known as chronic discoid lupus erythematosus or cutaneous lupus erythematosus, may cause rashes on the skin such as the face, limbs. Depending on the progression, it may be accompanied by follicular plugging and pigmentation.

The "drug-induced lupus" refers to lupus caused by administration of a specific drug.

The "neonatal lupus" is lupus that occurs in a newborn baby born to a mother who suffered from lupus during pregnancy.

Furthermore, lupus-related conditions may include lupus nephritis, pericarditis, pleuritis, interstitial pneumonia, and arthritis, which are conditions that co-occur with lupus.

In addition, the lupus-associated disease may include, for example, lupus-associated symptoms such as butterfly rash, pernio-like rash, Raynaud's phenomenon, oral ulcers, photosensitivity, and livedo.

In an embodiment, the lupus-associated disease may be systemic lupus erythematosus, discoid lupus erythematosus, drug-induced lupus, neonatal lupus, lupus nephritis, butterfly rash, or pernio-like rash, but are not limited to these.

In an embodiment, the pharmaceutical composition may reduce skin lesions. The pharmaceutical composition may reduce the skin lesion score increased by lupus-associated disease.

The pharmaceutical composition may further include a pharmaceutically acceptable carrier. Pharmaceutically acceptable carriers may include, in the case of oral administration, a binder, a lubricant, a disintegrant, an excipient, a solubilizer, a dispersant, a stabilizer, a suspending agent, a pigment, a flavor, etc.; in the case of injections, a combination of a buffer, a preservative, a painless agent, a solubilizing agent, an isotonic agent, a stabilizer, etc.; and in the case of topical administration, a base, an excipient, a lubricant, a preservative, etc.

Formulations of the pharmaceutical composition may be variously prepared by mixing with pharmaceutically acceptable carriers as described above. For example, in the case of oral administration, the formulation may be in the form of tablets, troches, capsules, elixirs, suspensions, syrups, wafers, etc., and in the case of injections, the formulation may be prepared in the form of unit dose ampoules or multiple doses. In addition, the formulation may be prepared in the form of solutions, suspensions, tablets, pills, capsules, and sustained-release preparations.

On the other hand, examples of carriers, excipients and diluents suitable for formulation include lactose, dextrose, sucrose, sorbitol, mannitol, xylitol, erythritol, maltitol, starch, acacia, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate, or mineral oil may be used. In addition, fillers, anti-coagulants, lubricants, wetting agents, flavoring agents, emulsifiers, and preservatives may be further included.

The pharmaceutical composition may further include one or more other agents for treating lupus-associated disease. In an embodiment, the other agents may be an anti-inflammatory or an immunosuppressant, but are not limited thereto. In an embodiment, the other agents may be a therapeutic agent for lupus, but are not limited thereto.

"Anti-inflammatory agent" used herein refers to a compound for the treatment of an inflammatory disease or conditions related thereto. Anti-inflammatory agents include, but are not limited to, non-steroidal anti-inflammatory drugs (NSAIDs, for example, aspirin, ibuprofen, naproxen, methyl salicylate, diflunisal, indomethacin, sulindac, diclofenac, ketoprofen, ketorolac, carprofen, fenoprofen, mefenamic acid, piroxicam, meloxicam, methotrexate, celecoxib, valdecoxib, parecoxib, etoricoxib, and nimesulide), corticosteroids (for example, prednisone, betamethasone, budesonide, cortisone, dexamethasone, hydrocortisone, methylprednisolone, prednisolone, triamcinolone, and fluticasone), rapamycin (for example, see the documents [Migita et al., Clin. Exp. Immunol. (1997) 108: 199-203]; [Migita et al., Clin. Exp. Immunol. (1996) 104: 86-91]; and [Foroncewicz et al., Transpl. Int. (2005) 18: 366-368]), high-density lipoprotein (HDL) and HDL-cholesterol raising compounds (for example, see the documents [Birjmohun et al. (2007) Arterioscler. Thromb. Vasc. Biol., 27: 1153-1158]; and [Nieland et al. (2007) J. Lipid Res., 48:1832-1845]; [Bloedon et al. (2008) J. Lipid Res., Samaha et al. (2006) Arterioscler. Thromb. Vasc. Biol., 26:1413-1414] disclosing the use of rosiglitazone as an anti-inflammatory agent, and [Duffy et al. (2005) Curr. Opin. Cardiol., 20:301-306]), rho-kinase inhibitors (for example, document [Hu, E. (2006) Rec. Patents Cardiovasc. Drug Discov., 1: 249-263]), antimalarial drugs (for example, hydroxychloroquine and chloroquine), acetaminophen, glucocorticoids, steroids, beta-agonists, anticholinergics, methylxanthines, gold injection (for example, sodium orothiomalate), sulfasalazine, penicillamine, antiangiogenic agents, dapsone, soralen, antiviral agents, statins (for example, see the document [Paraskevas et al. (2007) Curr. Pharm. Des., 13: 3622-36]; [Paraskevas, K. I. (2008) Clin. Rheumatol. 27: 281-287]), and antibiotics (for example, tetracycline). In embodiments, the anti-inflammatory agent is a statin, or high-density lipoprotein (HDL) or a HDL-cholesterol raising compound.

The "immunosuppressant" and the "immunosuppressive agent" include compounds or compositions that suppress an immune response or symptoms related thereto. Immunosuppressants include, but are not limited to, purine analogs (for example, azathioprine), methotrexate, cyclosporine (for example, cyclosporin A), cyclophosphamide, leflunomide, mycophenolate (mycophenolate mofetil), steroids (for example, glucocorticoids, corticosteroids), methylprednisone, prednisone, nonsteroidal anti-inflammatory drugs (NSAIDs), chloroquine, hydroxychloroquine, chlorambucil, CD20 antagonists (for example, rituximab, ocrelizumab, veltuzumab, or ofatumumab), abatacept, TNF antagonists (for example, infliximab, adalimumab, etanercept), macrolides (for example, pimecrolimus, tacrolimus (FK506)), and sirolimus), dihydroepiandrosterone, lenalidomide, CD40 antagonist (for example, anti-CD40L antibody), avetimus sodium, BLys antagonist (for example, anti-BLyS (for example, belimumab)), dactinomycin, bucillamine, penicillamine, leflunomide, mercaptopurine, pyrimidine analogs (for example, cytosine arabinoside), mizoribine, alkylating agents (for example, nitrogen mustard, phenylalanine mustard, busulfan, and cyclophosphamide), folic acid antagonists (for example, aminopterin and methotrexate), antibiotics (for example, rapamycin, actinomycin D, mitomycin C, furamycin, and chloramphenicol), human IgG, anti-lymphocyte globulin (ALG), antibody (for example, anti-CD3 (OKT3), anti-CD4 (OKT4), anti-CD5, anti-CD7, an anti-IL-2 receptor (for example, daclizumab and basiliximab), anti-alpha/beta TCR, anti-ICAM-1, muromonab-CD3, anti-IL-12, alemutuzumab, and antibodies to immunotoxins), 1-methyltryptophan, and derivatives and analogues thereof. In embodiments, the immunosuppressant may be selected from the group consisting of methotrexate, hydroxychloroquine, a CD20 antagonist (for example, rituximab, ocrelizumab, veltuzumab, or ofatumumab), abatacept, a TNF antagonist (for example, infliximab, adalimumab, etanercept), sirolimus, and BLyS antagonist (for example, anti-BLyS (for example, belimumab)).

The "therapeutic agent for lupus" includes a compound or composition that suppresses or treats lupus-associated symptoms. For use as a therapeutic agent for lupus, any known material may be used.

The dosage and frequency of the pharmaceutical composition are determined according to the type of drug as an active ingredient, together with various related factors such as the disease to be treated, the route of administration, the age, sex, and weight of the patient, and the severity of the disease.

Since the pharmaceutical composition has excellent in vivo persistence and potency, the number and frequency of administration can be significantly reduced.

Another aspect provides a method of preventing or treating lupus-associated disease, including administering an effective amount of the glucagon/GLP-1/GIP triple agonist, a pharmaceutically acceptable salt thereof, a solvate thereof, or a conjugate thereof, or the pharmaceutical composition to a subject in need thereof.

The glucagon/GLP-1/GIP triple agonist or a conjugate thereof, the pharmaceutically acceptable salt thereof, the solvate thereof, the conjugate, the pharmaceutical composition, and lupus-associated disease are the same as described above.

The "effective amount" or "pharmaceutically effective amount" refers to an amount or dosage of the glucagon/GLP-1/GIP triple agonist, a pharmaceutically acceptable salt thereof, a solvate thereof, or a conjugate thereof, which, when administered to a patient in a single dose or multiple doses, provides a desired effect in a patient under diagnosis or treatment. The effective amount may be easily determined by the attending physicians as a person skilled in the art by using known techniques or by observing results obtained under similar circumstances. An effective amount for a patient may be determined in consideration of: mammalian species or sizes, age and general health conditions thereof; the specific disease or disorder involved; degree of involvement or severity of the disease or disorder; individual patient responses; specific compounds being administered; administration modes; bioavailability characteristics of the administered agent; the selected dosing regimen; use of concomitant medication; and other relevant circumstances. However, conditions to be considered are not limited thereto, and a number of other factors may be further taken into account by attending physicians.

"Subject" refers to a target in need of treatment of a disease, for example, a mammal such as a human or non-human primate, mouse, rat, dog, cat, horse, and cow.

"Administering" refers to introducing a substance into a patient by any suitable method. The route of administration may be any general route capable of allowing to reach a target in vivo in a patient. The administration may be, for example, intraperitoneal administration, intravenous administration, intramuscular administration, subcutaneous administration, intradermal administration, oral administration, topical administration, intranasal administration, or intrarectal administration, but is not limited thereto.

The administration refers to the administration of the composition according to an embodiment in an amount of 0.0001 mg to 1,000 mg, for example, 0.1 mg to 1,000 mg, mg to 500 mg, 0.1 mg to 100 mg, 0.1 mg to 50 mg, 0.1 mg to 25 mg, 1 mg to 1,000 mg, 1 mg to 500 mg, 1 mg to 100 mg, 1 mg to 50 mg, or 1 mg to 25 mg. However, the dosage may be prescribed in various ways depending on factors such as formulation method, administration method, the age, weight, and sex of the patient, pathological condition, food, administration time, administration route, excretion rate, and response sensitivity, and those skilled in the art may appropriately adjust in consideration of these factors. The number of administrations may be once a day or two or more times within the range of clinically acceptable side effects, and administration may be performed at one or two or more sites, daily or at intervals of 2 to 5 days. The number of administration days may be from 1 day to 30 days per treatment. If necessary, the same treatment can be repeated after a titration period. For non-human animals, the same dosage per kg as for humans is used, or the dosage is adjusted based on the volume ratio (for example, average value) of the human organ (heart, etc.) to the organ of the target animal, and then, administered.

In the method, an effective amount of the glucagon/GLP-1/GIP triple agonist, a pharmaceutically acceptable salt thereof, a solvate thereof, or a conjugate thereof may be administered simultaneously, separately, or sequentially with an effective amount of one or more other active ingredients. The one or more other active ingredients may be one or more other agents for treating lupus-associated disease, but are not limited thereto.

Another aspect provides use of the glucagon/GLP-1/GIP triple agonist, a pharmaceutically acceptable salt thereof, the solvate thereof, or the conjugate thereof for use in preparing a drug for preventing or treating lupus-associated disease.

The glucagon/GLP-1/GIP triple agonist or a conjugate thereof, the pharmaceutically acceptable salt thereof, the solvate thereof, the conjugate, and lupus-associated disease are the same as described above.

Each description and embodiment disclosed herein may also be applied to other descriptions and embodiments. That is, all combinations of the various elements disclosed herein fall within the scope of the present disclosure. In addition, it cannot be said that the scope of the present disclosure is limited by the specific description described below.

Advantageous Effects of Disclosure

The glucagon/GLP-1/GIP triple agonist according to an aspect or a long-acting conjugate thereof, alleviates edema, restores skin lesions, and reduces the weight and size of the spleen enlarged due to inflammatory response, in lupus disease model mice. Accordingly, the glucagon/GLP-1/GIP triple agonist or a conjugate thereof can be used for the prevention or treatment of lupus-associated disease.

BEST MODE

Figure 1:
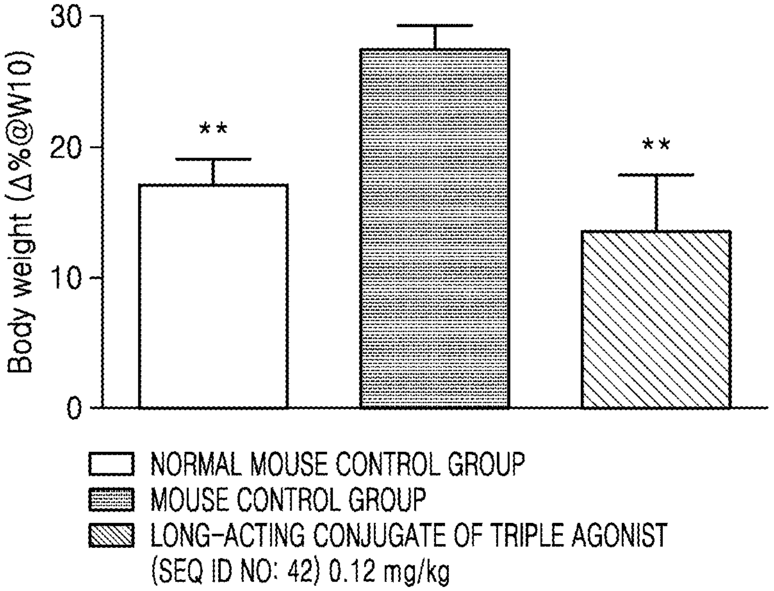
FIG. 1 is a graph showing the change rate (%) in body weight after 10 weeks in a normal mouse control group, a disease model (MRL/Ipr) mouse control group, and a triple-agonist long-acting conjugate-administered group.

Hereinafter, the present disclosure will be described in more detail through examples. However, these examples are intended to illustrate the present disclosure for illustrative purpose, and the scope of the present disclosure is not limited to these examples.

Example 1: Preparation of Glucagon/GLP-1/GIP Triple Agonist

A glucagon/GLP-1/GIP triple agonist exhibiting activity on all of a glucagon receptor, a GLP-1 receptor, and a GIP receptor was prepared and sequences thereof are shown in Table 1 below.

TABLE 1

| Sequence number | Sequence | Information |
|---|---|---|
| 1 | H X Q G T F T S D V S S Y L D G Q A A K E F I A W L V K G C | |
| 2 | H X Q G T F T S D V S S Y L D G Q A Q K E F I A W L V K G C | |
| 3 | H X Q G T F T S D V S S Y L L G Q A A K Q F I A W L V K G G G P S S G A<br>P P P S C | |
| 4 | H X Q G T F T S D V S S Y L L G Q Q Q K E F I A W L V K G C | |
| 5 | H X Q G T F T S D V S S Y L L G Q Q Q K E F I A W L V K G G G P S S G A<br>P P P S C | |
| 6 | H X Q G T F T S D V S S Y L D G Q A A K E F V A W L L K G C | |
| 7 | H X Q G T F T S D V S K Y L D G Q A A K E F V A W L L K G C | |
| 8 | H X Q G T F T S D V S K Y L D G Q A A Q E F V A W L L K G C | |
| 9 | H X Q G T F T S D V S K Y L D G Q A A Q E F V A W L L A G C | |
| 10 | H X Q G T F T S D V S K Y L D G Q A A Q E F V A W L L A G G G P S S G<br>A P P P S C | |
| 11 | C A G E G T F T S D L S K Y L D S R R Q Q L F V Q W L K A G G P S S G A<br>P P P S H G | |
| 12 | C A G E G T F IS D L S K Y M D E Q A V Q L F V E W L M A G G P S S G A<br>P P P S H G | |
| 13 | C A G E G T F IS D Y S I Q L D E I A V Q D F V E W L L A Q K P S S G A P<br>P P S H G | |
| 14 | C A G Q G T F T S D Y S I Q L D E I A V R D F V E W L K N G G P S S G A<br>P P P S H G | |
| 15 | C A G Q G T F T S D L S K Q M D E E A V R L F I E W L K N G G P S S G A<br>P P P S H G | |
| 16 | C A G Q G T F T S D L S K Q M D S E A Q Q L F I E W L K N G G P S S G A<br>P P P S H G | |
| 17 | C A G Q G T F T S D L S K Q M D E E R A R E F I E W L L A Q K P S S G A<br>P P P S H G | |
| 18 | C A G Q G T F T S D L S K Q M D S E R A R E F I E W L K N T G P S S G A<br>P P P S H G | |
| 19 | C A G Q G T F T S D L S I Q Y D S E H Q R D F I E W L K D T G P S S G A<br>P P P S H G | |
| 20 | C A G Q G T F T S D L S I Q Y E E E A Q Q D F V E W L K D T G P S S G A<br>P P P S H G | |
| 21 | Y X Q G T F T S D Y S K Y L D E C R A K E F V Q W L L D H H P S S G Q P<br>P P S | Ring formation |
| 22 | Y X Q G T F T S D Y S K C L D E K R A K E F V Q W L L D H H P S S G Q P<br>P P S | Ring formation |
| 23 | Y X Q G T F T S D Y S K Y L D E C R A K E F V Q W L L A Q K G K K N D<br>W K H N I T | Ring formation |
| 24 | Y X Q G T F T S D Y S K Y L D E C R A K E F V Q W L K N G G P S S G A P<br>P P S | Ring formation |
| 25 | H X Q G T F T S D C S K Y L D E R A A Q D F V Q W L L D G G P S S G A<br>P P P S | |
| 26 | H X Q G T F T S D C S K Y L D S R A A Q D F V Q W L L D G G P S S G A<br>P P P S | |
| 27 | H X Q G T F T S D Y S K Y L D E R A C Q D F V Q W L L D Q G G P S S G<br>A P P P S | |
| 28 | H X Q G T F T S D Y S K Y L D E K R A Q E F V C W L L A Q K G K K N D<br>W K H N I T | |

TABLE 1-continued

| Sequence number | Sequence | Information |
|---|---|---|
| 29 | H X Q G T F T S D Y S K Y L D E K A A K E F V Q W L L N T C | Ring formation |
| 30 | H X Q G T F T S D Y S K Y L D E K A Q K E F V Q W L L D T C | Ring formation |
| 31 | H X Q G T F T S D Y S K Y L D E K A C K E F V Q W L L A Q | Ring formation |
| 32 | H X Q G T F T S D Y S K Y L D E K A C K D F V Q W L L D G G P S S G A P<br>P P S | Ring formation |
| 33 | H X Q G T F T S D Y S I A M D E I H Q K D F V N W L L A Q K C | Ring formation |
| 34 | H X Q G T F T S D Y S K Y L D E K R Q K E F V N W L L A Q K C | Ring formation |
| 35 | H X Q G T F T S D Y S I A M D E I H Q K D F V N W L L N T K C | Ring formation |
| 36 | H X Q G T F T S D Y S K Y L C E K R Q K E F V Q W L L N G G P S S G A P<br>P P S G | Ring formation |
| 37 | H X Q G T F T S D Y S K Y L D E C R Q K E F V Q W L L N G G P S S G A<br>P P P S G | Ring formation |
| 38 | C A X Q G T F T S D K S S Y L D E R A A Q D F V Q W L L D G G P S S G A<br>P P P S S | |
| 39 | H X Q G T F T S D Y S K Y L D G Q H A Q C F V A W L L A G G G P S S G<br>A P P P S | |
| 40 | H X Q G T F T S D K S K Y L D E R A C Q D F V Q W L L D G G P S S G A<br>P P P S | |
| 41 | H X Q G T F T S D K S K Y L D E C A A Q D F V Q W L L D G G P S S G A<br>P P P S | |
| 42 | Y X Q G T F T S D Y S K Y L D E K R A K E F V Q W L L D H H P S S G Q P<br>P P S C | Ring formation |
| 43 | Y X Q G T F T S D Y S K Y L D E K R A K E F V Q W L L D H H C S S G Q P<br>P P S | Ring formation |
| 44 | H G Q G T F T S D C S K Q L D G Q A A Q E F V A W L L A G G P S S G A<br>P P P S | |
| 45 | H G Q G T F T S D C S K Y M D G Q A A Q D F V A W L L A G G P S S G A<br>P P P S | |
| 46 | H G Q G T F T S D C S K Y L D E Q H A Q E F V A W L L A G G P S S G A<br>P P P S | |
| 47 | H G Q G T F T S D C S K Y L D G Q R A Q E F V A W L L A G G P S S G A<br>P P P S | |
| 48 | H G Q G T F T S D C S K Y L D G Q R A Q D F V N W L L A G G P S S G A<br>P P P S | |
| 49 | C A X Q G T F T S D Y S I C M D E I H Q K D F V N W L L N T K | Ring formation |
| 50 | H X Q G T F T S D Y S K Y L D E K R A K E F V Q W L L D H H P S S G Q P<br>P P S C | Ring formation |
| 51 | H X Q G T F T S D Y S K Y L D E K R Q K E F V Q W L L N T C | Ring formation |
| 52 | H X Q G T F T S D Y S K Y L D E K R Q K E F V Q W L L D T C | Ring formation |
| 53 | H X E G T F T S D Y S I A M D E I H Q K D F V N W L L A Q C | Ring formation |
| 54 | H X E G T F T S D Y S I A M D E I H Q K D F V D W L L A E C | Ring formation |

TABLE 1-continued

| Sequence number | Sequence | Information |
|---|---|---|
| 55 | H X Q G T F T S D Y S I A M D E I H Q K D F V N W L L A Q C | Ring formation |
| 56 | H X Q G T F T S D Y S K Y L D E K R Q K E F V N W L L A Q C | Ring formation |
| 57 | H X Q G T F T S D Y S I A M D E I H Q K D F V N W L L N T C | Ring formation |
| 58 | H X Q G T F T S D Y S K Y L D E K R Q K E F V Q W L L N T K C | Ring formation |
| 59 | C A X Q G T F T S D Y S I C M D E K H Q K D F V N W L L N T K | Ring formation |
| 60 | C A X Q G T F T S D Y S I A M D E K H C K D F V N W L L N T K | Ring formation |
| 61 | C A X Q G T F T S D Y S I A M D E I A C K D F V N W L L N T K | Ring formation |
| 62 | C A X Q G T F T S D K S K Y L D E R A A Q D F V Q W L L D G G P S S G A P P P S | |
| 63 | C A X Q G T F T S D C S K Y L D E R A A Q D F V Q W L L D G G P S S G A P P P S | |
| 64 | Y X Q G T F T S D Y S K Y L D E C A A K E F V Q W L L D H H P S S G Q P P P S | Ring formation |
| 65 | H X Q G T F T S D Y S K C L D E K R A K E F V Q W L L D H H P S S G Q P P P S | Ring formation |
| 66 | Y X Q G T F T S D Y S K Y L D E C R A K D F V Q W L L D H H P S S G Q P P P S | Ring formation |
| 67 | Y X Q G T F T S D Y S K Y L D E C A A K D F V Q W L L D H H P S S G Q P P P S | Ring formation |
| 68 | Y X Q G T F T S D Y S K C L D E K A A K E F V Q W L L D H H P S S G Q P P P S | Ring formation |
| 69 | Y X Q G T F T S D Y S K C L D E R A A K E F V Q W L L D H H P S S G Q P P P S | Ring formation |
| 70 | Y X Q G T F T S D Y S K C L D E K R A K D F V Q W L L D H H P S S G Q P P P S | Ring formation |
| 71 | Y X Q G T F T S D Y S K Y L D E R A C K D F V Q W L L D H H P S S G Q P P P S | Ring formation |
| 72 | Y X Q G T F T S D C S K Y L D E R A A K D F V Q W L L D H H P S S G Q P P P S | Ring formation |
| 73 | C A X Q G T F T S D Y S K Y L D E C R A K E F V Q W L L D H H P S S G Q P P P S | Ring formation |
| 74 | C A X Q G T F T S D Y S K C L D E K R A K E F V Q W L L D H H P S S G Q P P P S | Ring formation |
| 75 | Y X Q G T F T S D Y S K Y L D E K A A K E F V Q W L L D H H P S S G Q P P P S C | Ring formation |
| 76 | Y X Q G T F T S D Y S K Y L D E K R A K D F V Q W L L D H H P S S G Q P P P S C | Ring formation |
| 77 | Y X Q G T F T S D Y S K Y L D E K A A K D F V Q W L L D H H P S S G Q P P P S C | Ring formation |
| 78 | H X Q G T F T S D Y S K Y L D E K R Q K E F V Q W L L D T K C | Ring formation |
| 79 | H X E G T F T S D Y S I A M D E I H Q K D F V N W L L A Q K C | Ring formation |

TABLE 1-continued

| Sequence number | Sequence | Information |
|---|---|---|
| 80 | H X E G T F T S D Y S I A M D E I H Q K D F V D W L L A E K C | Ring formation |
| 81 | C A X Q G T F T S D Y S K Y L D E K R Q K E F V Q W L L N T C | Ring formation |
| 82 | C A X Q G T F T S D Y S K Y L D E K R Q K E F V Q W L L D T C | Ring formation |
| 83 | C A X E G T F T S D Y S I A M D E I H Q K D F V N W L L A Q C | Ring formation |
| 84 | C A X E G T F T S D Y S I A M D E I H Q K D F V D W L L A E C | Ring formation |
| 85 | C A X Q G T F T S D Y S I A M D E I H Q K D F V N W L L A Q C | Ring formation |
| 86 | C A X Q G T F T S D Y S K Y L D E K R Q K E F V N W L L A Q C | Ring formation |
| 87 | C A X Q G T F T S D Y S I A M D E I H Q K D F V N W L L N T C | Ring formation |
| 88 | C A X Q G T F T S D Y S K Y L D E K R Q K E F V Q W L L N T K C | Ring formation |
| 89 | C A X Q G T F T S D Y S K Y L D E K R Q K E F V Q W L L D T K C | Ring formation |
| 90 | C A X E G T F T S D Y S I A M D E I H Q K D F V N W L L A Q K C | Ring formation |
| 91 | C A X E G T F T S D Y S I A M D E I H Q K D F V D W L L A E K C | Ring formation |
| 92 | C A X Q G T F T S D Y S I A M D E I H Q K D F V N W L L A Q K C | Ring formation |
| 93 | C A X Q G T F T S D Y S K Y L D E K R Q K E F V N W L L A Q K C | Ring formation |
| 94 | C A X Q G T F T S D Y S I A M D E I H Q K D F V N W L L N T K C | Ring formation |
| 95 | Y X Q G T F T S D Y S K Y L D E K R A K E F V Q W L L C H H P S S G Q P P P S | Ring formation |
| 96 | Y X Q G T F T S D Y S K Y L D E K R A K E F V Q W L L D H C P S S G Q P P P S | Ring formation |
| 97 | Y X Q G T F T S D Y S K Y L D E K R A K E F V Q W L L D C H P S S G Q P P P S | Ring formation |
| 98 | Y X Q G T F T S D Y S K A L D E K A A K E F V N W L L D H H P S S G Q P P P S C | Ring formation |
| 99 | Y X Q G T F T S D Y S K A L D E K A A K D F V N W L L D H H P S S G Q P P P S C | Ring formation |
| 100 | Y X Q G T F T S D Y S K A L D E K A A K E F V Q W L L D Q H P S S G Q P P P S C | Ring formation |
| 101 | Y X Q G T F T S D Y S K A L D E K A A K E F V N W L L D Q H P S S G Q P P S C | Ring formation |
| 102 | Y X Q G T F T S D Y S K A L D E K A A K D F V N W L L D Q H P S S G Q P P P S C | Ring formation |

From among the sequences shown in Table 1, the amino acid indicated by X is Aib (aminoisobutyric acid), which is a non-native-type amino acid, and the underlined amino acid indicates that the underlined amino acids form a ring with each other. In addition, CA in Table 1 indicates 4-imidazoacetyl and Y indicates tyrosine.

For use as the triple agonist peptide, a triple agonist in which the C-terminus is amidated, may be used, if necessary.

Example 2: Preparation of Long-Acting Conjugates of Triple Agonists

To pegylate 10 kDa of PEG having a maleimide group and an aldehyde group at oppose ends thereof, that is, maleimide-PEG-aldehyde (10 kDa, NOF, Japan) to the cysteine residue of the triple agonist of Example 1 (SEQ ID NOs: 21, 22, 42, 43, 50, 77, and 96), the triple agonist was reacted with maleimide-PEG-aldehyde at low temperature for 0.5 hour to 3 hours in such conditions that the molar ratio of the triple agonist to maleimide-PEG-aldehyde was 1:1 to 3, and the protein concentration was 1 mg/ml to 5 mg/ml. In this regard, this reaction was performed in an environment in which 20% to % isopropanol was added to 50 mM tris buffer (pH 7.5). After the reaction was completed, the reaction solution was applied to SP Sepharose HP (GE healthcare, USA) to purify the triple agonist that is mono-PEGylated to cysteine.

Next, the reaction was caused to occur at 4° C. to 8° C. for 12 hours to 18 hours in such conditions that the molar ratio of the purified mono-PEGylated triple agonist to immunoglobulin Fc was 1:1 to 5 and a protein concentration was 10 mg/ml to 50 mg/ml. The reaction was performed in an environment in which 10 mM to 50 mM sodium cyanoborohydride and 10% to 30% isopropanol were added as reducing agents to 100 mM potassium phosphate buffer (pH 6.0). After the reaction was completed, the reaction solution was applied to a Butyl Sepharose FF purification column (GE healthcare, USA) and a Source ISO purification column (GE healthcare, USA) to purify a conjugate containing the triple agonist and immunoglobulin Fc.

After preparation, the purity of the obtained product was analyzed using reverse phase chromatography, size exclusion chromatography, and ion exchange chromatography, and the obtained purity level was more than 95%.

In this regard, the conjugate in which the triple agonist of SEQ ID NO: 21 and immunoglobulin Fc are linked through PEG is called “conjugate containing SEQ ID NO: 21 and immunoglobulin Fc” or “long-acting conjugate of SEQ ID NO: 21” and these two terms can be used interchangeably herein.

In this regard, the conjugate in which the triple agonist of SEQ ID NO: 22 and immunoglobulin Fc are linked through PEG is called “conjugate containing SEQ ID NO: 22 and immunoglobulin Fc” or “long-acting conjugate of SEQ ID NO: 22” and these two terms can be used interchangeably herein.

In this regard, the conjugate in which the triple agonist of SEQ ID NO: 42 and immunoglobulin Fc are linked through PEG is called “conjugate containing SEQ ID NO: 42 and immunoglobulin Fc” or “long-acting conjugate of SEQ ID NO: 42” and these two terms can be used interchangeably herein.

In this regard, the conjugate in which the triple agonist of SEQ ID NO: 43 and immunoglobulin Fc are linked through PEG is called “conjugate containing SEQ ID NO: 43 and immunoglobulin Fc” or “long-acting conjugate of SEQ ID NO: 43” and these two terms can be used interchangeably herein.

In this regard, the conjugate in which the triple agonist of SEQ ID NO: 50 and immunoglobulin Fc are linked through PEG is called “conjugate containing SEQ ID NO: 50 and immunoglobulin Fc” or “long-acting conjugate of SEQ ID NO: 50” and these two terms can be used interchangeably herein.

In this regard, the conjugate in which the triple agonist of SEQ ID NO: 77 and immunoglobulin Fc are linked through PEG is called “conjugate containing SEQ ID NO: 77 and immunoglobulin Fc” or “long-acting conjugate of SEQ ID NO: 77” and these two terms can be used interchangeably herein.

In this regard, the conjugate in which the triple agonist of SEQ ID NO: 96 and immunoglobulin Fc are linked through PEG is called “conjugate containing SEQ ID NO: 96 and immunoglobulin Fc” or “long-acting conjugate of SEQ ID NO: 96” and these two terms can be used interchangeably herein.

Experimental Example 1: Measurement of In Vitro Activity of Triple Agonist and Long-Acting Conjugate Thereof In order to measure the activity of the triple agonists and long-acting conjugates thereof prepared according to Examples 1 and 2, the in-vitro cell activity was measured using cell lines transformed with GLP-1 receptor, glucagon (GCG) receptor, and GIP receptor, respectively.

The cell lines were transformed to express human GLP-1 receptor, human GCG receptor and human GIP receptor genes in Chinese hamster ovary (CHO), respectively, and are suitable for measuring the activities of GLP-1, GCG, and GIP. Therefore, the activity for each part was measured using each transformed cell line.

To measure the GLP-1 activity of the triple agonists and long-acting conjugates prepared according to Examples 1 and 2, human GLP-1 was diluted from 50 nM to nM by 4-fold serial dilution, and the triple agonists and long-acting conjugates thereof prepared according to Examples 1 and 2 were diluted from 400 nM to 0.00038 nM by 4-fold serial dilution. The culture medium was removed from the cultured human GLP-1 receptor-expressing CHO cells, 5 μl of each of the serially diluted materials was added to the cells, and then 5 μl of buffer containing cAMP antibody was added to the cells, followed by 15 minutes of incubation at room temperature. Then, cells were lysed by adding 10 μl of detection mix containing cell lysis buffer, and reacted at room temperature for 90 minutes. The cell lysate after the reaction had been completed, was applied to the LANCE cAMP kit (PerkinElmer, USA) to calculate the $EC_{50}$ value through the accumulated cAMP, and then compared with each other. Relative titers compared to human GLP-1 are shown in Tables 2 and 3 below.

To measure the GCG activity of the triple agonists and long-acting conjugates prepared according to Examples 1 and 2, human GCG was diluted from 50 nM to nM by 4-fold serial dilution, and the triple agonists and long-acting conjugates thereof prepared according to Examples 1 and 2 were diluted from 400 nM to 0.00038 nM by 4-fold serial dilution. The culture medium was removed from the cultured human GCG receptor-expressing CHO cells, 5 μl of each of the serially diluted materials was added to the cells, and then 5 μl of buffer containing cAMP antibody was added to the cells, followed by 15 minutes of incubation at room temperature. Then, cells were lysed by adding 10 µl of detection mix containing cell lysis buffer, and reacted at room temperature for 90 minutes. The cell lysate after the reaction had been completed, was applied to the LANCE cAMP kit (PerkinElmer, USA) to calculate the $EC_{50}$ value through the accumulated cAMP, and then compared with each other. Relative titers compared to human GCG are shown in Tables 2 and 3 below.

To measure the GIP activity of the triple agonists and long-acting conjugates thereof prepared according to Examples 1 and 2, human GIP was diluted from 50 nM to nM by 4-fold serial dilution, and the triple agonists and long-acting conjugates thereof prepared according to Examples 1 and 2 were diluted from 400 nM to 0.00038 nM by 4-fold serial dilution. The culture medium was removed from the cultured human GIP receptor-expressing CHO cells, 5 µl of each of the serially diluted materials was added to the cells, and then 5 µl of buffer containing cAMP antibody was added to the cells, followed by 15 minutes of incubation at room temperature. Then, cells were lysed by adding 10 µl of detection mix containing cell lysis buffer, and reacted at room temperature for 90 minutes. The cell lysate after the reaction had been completed, was applied to the LANCE cAMP kit (PerkinElmer, USA) to calculate the $EC_{50}$ value through the accumulated cAMP, and then compared with each other. Relative titers compared to human GIP are shown in Tables 2 and 3 below.

TABLE 2

| Triple agonist Sequence | In vitro activity compared to native peptide (%) | | |
|---|---|---|---|
| number | vs GLP-1 | vs Glucagon | vs GIP |
| 1 | 3.2 | <0.1 | <0.1 |
| 2 | 5.9 | <0.1 | <0.1 |
| 3 | 1.8 | <0.1 | <0.1 |
| 4 | 8.5 | <0.1 | <0.1 |
| 5 | 42.1 | <0.1 | <0.1 |
| 6 | 17.0 | <0.1 | <0.1 |
| 7 | 13.7 | <0.1 | <0.1 |
| 8 | 14.2 | 0.10 | <0.1 |
| 9 | 32.1 | 0.13 | <0.1 |
| 10 | 46.0 | <0.1 | <0.1 |
| 11 | 1.4 | <0.1 | <0.1 |
| 12 | 0.4 | <0.1 | <0.1 |
| 13 | <0.1 | <0.1 | <0.1 |
| 14 | 28.0 | <0.1 | <0.1 |
| 15 | 79.2 | <0.1 | <0.1 |
| 16 | 2.1 | <0.1 | <0.1 |
| 17 | 0.2 | <0.1 | <0.1 |
| 18 | <0.1 | <0.1 | <0.1 |
| 19 | <0.1 | <0.1 | <0.1 |
| 20 | <0.1 | <0.1 | <0.1 |
| 21 | 17.8 | 267 | 22.7 |
| 22 | 20.1 | 140 | 59.7 |
| 23 | 4.01 | 9.3 | <0.1 |
| 24 | 41.2 | 9.3 | <0.1 |
| 25 | 82.6 | 0.1 | <0.1 |
| 26 | 64.5 | 0.2 | <0.1 |
| 27 | 83.1 | 0.8 | 0.9 |
| 28 | 17.2 | 1.6 | <0.1 |
| 29 | 38.5 | 6.0 | <0.1 |
| 30 | 142 | 0.7 | 0.8 |
| 31 | 135 | 2.2 | 2.4 |
| 32 | 151 | 1.7 | 8.8 |
| 33 | 24.5 | <0.1 | 10.4 |
| 34 | 19.1 | 0.92 | 0.6 |
| 35 | 7.5 | <0.1 | 1.3 |
| 36 | 37.4 | 0.39 | 0.2 |
| 37 | 236 | 6.21 | 2.2 |
| 38 | 2.3 | — | — |
| 39 | 13.9 | 0.53 | <0.1 |
| 40 | 75.2 | <0.1 | <0.1 |
| 41 | 34.3 | <0.1 | <0.1 |

TABLE 2-continued

| Triple agonist Sequence | In vitro activity compared to native peptide (%) | | |
|---|---|---|---|
| number | vs GLP-1 | vs Glucagon | vs GIP |
| 42 | 33.9 | 205.8 | 7.8 |
| 43 | 12.6 | 88.4 | 3.70 |
| 44 | 1.3 | <0.1 | <0.1 |
| 45 | 6.6 | <0.1 | <0.1 |
| 46 | 1.4 | <0.1 | <0.1 |
| 47 | 2.4 | <0.1 | <0.1 |
| 48 | 1.5 | <0.1 | <0.1 |
| 49 | 29.8 | <0.1 | 3.3 |
| 50 | 67.4 | 50.5 | 2.7 |
| 51 | 14.4 | 2.0 | 0.1 |
| 52 | 44.1 | 7.5 | 0.3 |
| 53 | 161 | 8.4 | 1.3 |
| 54 | 30.6 | 1.4 | 0.1 |
| 55 | 27.1 | 0.7 | 2.4 |
| 56 | 57.9 | 4.9 | 0.8 |
| 57 | 11.7 | <0.1 | 0.3 |
| 58 | 39.1 | 2.6 | 0.2 |
| 59 | 40.3 | <0.1 | 4.0 |
| 60 | 106.2 | <0.1 | 18.2 |
| 61 | 59.8 | <0.1 | 2.8 |
| 62 | 5.2 | <0.1 | <0.1 |
| 63 | 15.3 | <0.1 | <0.1 |
| 64 | 64.6 | 60.1 | 92.9 |
| 65 | 95.4 | 25.2 | 11.6 |
| 66 | 15.8 | 172 | 17.2 |
| 67 | 28.5 | 46.2 | 39.8 |
| 68 | 27.9 | 8.8 | 107 |
| 69 | 24.3 | 9.6 | 62.8 |
| 70 | 15.1 | 71.3 | 64.4 |
| 71 | 90.1 | 12.7 | 94.7 |
| 72 | 11.5 | 1.0 | 1.6 |
| 73 | 22.6 | 5.4 | 3.0 |
| 74 | 12.9 | 0.9 | 1.0 |
| 75 | 35.1 | 8.5 | 18.0 |
| 76 | 10.3 | 47.6 | 11.7 |
| 77 | 38.7 | 12.2 | 35.5 |
| 78 | 51.0 | 14.0 | 0.12 |
| 79 | 41.5 | 4.9 | 1.4 |
| 80 | 8.1 | 0.0 | 0.1 |
| 81 | 7.8 | 0.3 | <0.1 |
| 82 | 9.5 | 1.1 | <0.1 |
| 83 | 47.3 | 1.3 | 0.4 |
| 84 | 4.2 | <0.1 | <0.1 |
| 85 | 4.3 | <0.1 | 0.3 |
| 86 | 28.4 | 0.4 | 0.2 |
| 87 | 0.9 | <0.1 | <0.1 |
| 88 | 9.6 | 0.3 | <0.1 |
| 89 | 7.1 | 0.7 | <0.1 |
| 90 | 7.4 | <0.1 | <0.1 |
| 91 | 31.9 | 16.8 | 0.3 |
| 92 | 0.8 | <0.1 | 0.4 |
| 93 | 5.7 | 0.3 | 0.7 |
| 94 | 0.5 | <0.1 | <0.1 |
| 95 | 2.1 | 0.4 | <0.1 |
| 96 | 34.4 | 194.8 | 5.2 |
| 97 | 10.5 | 62.8 | 2.6 |
| 98 | 28.1 | 8.2 | 47.1 |
| 99 | 20.9 | 14.9 | 57.7 |
| 100 | 42.2 | 12.7 | 118.5 |
| 101 | 23.2 | 13.9 | 40.1 |
| 102 | 23.3 | 29.5 | 58.0 |

TABLE 3

| Long-acting | In vitro activity compared to native peptide (%) | | |
|---|---|---|---|
| conjugate | vs GLP-1 | vs Glucagon | vs GIP |
| 21 | 0.1 | 1.6 | 0.2 |
| 22 | 0.1 | 0.9 | 0.5 |
| 42 | 3.1 | 23.1 | 1.2 |

TABLE 3-continued

| Long-acting | In vitro activity compared to native peptide (%) | | |
|---|---|---|---|
| conjugate | vs GLP-1 | vs Glucagon | vs GIP |
| 43 | 2.1 | 13.5 | 0.6 |
| 50 | 15.4 | 6.9 | 0.7 |
| 77 | 6.7 | 1.7 | 6.6 |
| 96 | 0.3 | 4.0 | 0.3 |

The long-acting conjugates of the triple agonists prepared above can function as a triple agonist that activates all of the GLP-1 receptor, GIP receptor, and glucagon receptor.

Experimental Example 2: Confirmation of Efficacy of Long-Acting Conjugate of Triple Agonist in Lupus Disease Model MRL/Ipr mice were used to confirm the efficacy of the long-acting triple agonist conjugate on lupus in a disease model.

There were a normal mouse control group and a disease model control group, each administered with excipient, and a test group administered with 0.12 mg/kg of a long-acting triple agonist conjugate. The excipient and the long-acting conjugate of the triple agonist were administered every 2 days, and the experiment was terminated on the 10th week. As the long-acting conjugate of the triple agonist, the long-acting conjugate prepared according to Example 2 (SEQ ID NO: 42) was used.

During the treatment period, body weight was measured, and the severity of skin lesions was scored by observing the mouths, ears, areas around the wings, and eyes at weekly intervals starting from week 4. After the experiment was completed, the spleen was taken through autopsy, and the weight was measured and observed.

FIG. 1 is a graph showing the change rate (%) in body weight after 10 weeks in a normal mouse control group, a disease model (MRL/Ipr) mouse control group, and a triple-agonist long-acting conjugate-administered group.

As shown in FIG. 1, it was confirmed that the disease model has increased body weight compared to normal mice. In patients with lupus, weight gain is a common feature due to systemic edema caused by inflammatory responses, and the disease model also shows a similar characteristic. In addition, in the case of the test group administered with the long-acting conjugate of the triple agonist, the body weight was reduced compared to the disease model mouse control group, indicating an improvement in edema.

Figure 2:
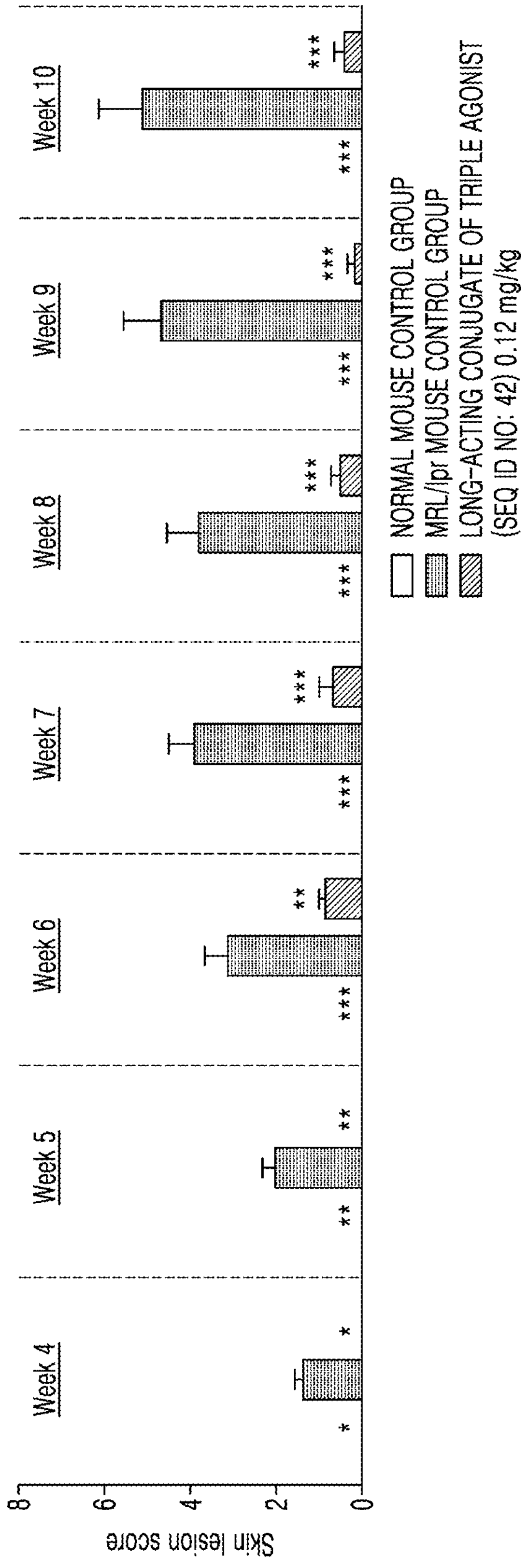
FIG. 2 is a graph showing the skin lesion scores during 10 weeks in a normal mouse control group, a disease model (MRL/Ipr) mouse control group, and a triple-agonist long-acting conjugate-administered group.

FIG. 2 is a graph showing the skin lesion scores after 10 weeks in a normal mouse control group, a disease model (MRL/Ipr) mouse control group, and a triple-agonist long-acting conjugate-administered group.

As shown in FIG. 2, it was confirmed that skin lesions in the disease model control group worsened over time. However, in the case of the triple-agonist long-acting conjugate-administered group, the severity of skin lesions was restored to a level similar to that of the normal mouse.

Figure 3A:
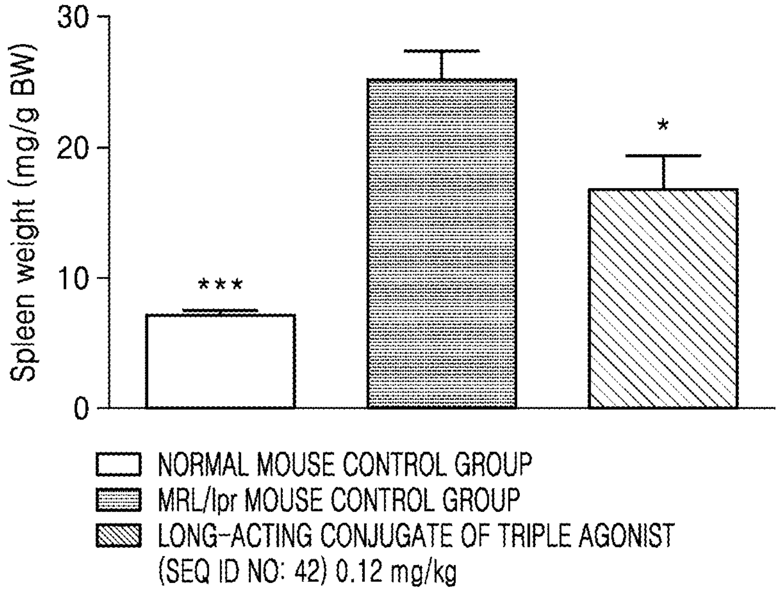
FIG. 3A is a graph showing the weight of spleen after 10 weeks in a normal mouse control group, a disease model (MRL/Ipr) mouse control group, and a triple-agonist long-acting conjugate-administered group.

FIG. 3A is a graph showing the weight of spleen after 10 weeks in a normal mouse control group, a disease model (MRL/Ipr) mouse control group, and a triple-agonist long-acting conjugate-administered group.

Figure 3B:
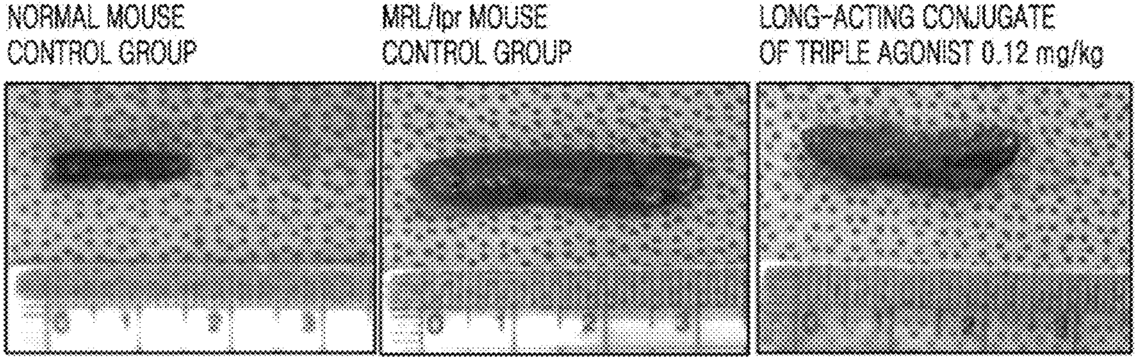
FIG. 3B is a graph showing the size of spleen after 10 weeks in a normal mouse control group, a disease model (MRL/Ipr) mouse control group, and a triple-agonist long-acting conjugate-administered group.

FIG. 3B is a graph showing the size of spleen after 10 weeks in a normal mouse control group, a disease model (MRL/Ipr) mouse control group, and a triple-agonist long-acting conjugate-administered group.

As shown in FIGS. 3A and 3B, the disease model control group showed a characteristic of a significantly enlarged spleen due to inflammatory responses. In the case of the triple-agonist long-acting conjugate-administered group, it was confirmed that the weight and size of the spleen were decreased compared to the disease model control group.

Therefore, it can be seen that the long-acting conjugate of the triple agonist has therapeutic or ameliorative effects on lupus-related diseases.

The invention claimed is:

1. A method for treating, or reducing the likelihood of developing, a lupus-associated disease in a subject in need thereof, said method comprising administering to the subject an effective amount of a pharmaceutical composition comprising:

a pharmaceutically acceptable excipient; and a pharmaceutically effective amount of a peptide comprising an amino acid sequence of any one of SEQ ID NOs: 1 to 102.

2. The method of claim 1, wherein the peptide is in a form of a long-acting conjugate, and the long-acting conjugate is represented by Formula 1:

X-L-F    Formula 1 wherein X is a peptide comprising an amino acid sequence of any one of SEQ ID NOs: 1 to 102;

L is a linker containing an ethylene glycol repeating unit,

F is an immunoglobulin Fc region, and

- represents a covalent bonding linkage between X and L and a covalent bonding linkage between L and F.

3. The method of claim 1, wherein the peptide is amidated at a C-terminus thereof.

4. The method of claim 1, wherein the peptide comprises an amino acid sequence selected from the group consisting of SEQ ID NOs: 21, 22, 42, 43, 50, 64, 66, 67, 70, 71, 76, 77, 96, 97 and 100.

5. The method of claim 4, wherein the peptide comprises an amino acid sequence selected from the group consisting of SEQ ID NOs: 21, 22, 42, 43, 50, 66, 67, 77, 96, 97, and 100.

6. The method of claim 5, wherein the peptide comprises an amino acid sequence selected from the group consisting of SEQ ID NOs: 21, 22, 42, 43, 50, 77, and 96.

7. The method of claim 1, wherein a 16th amino acid and a 20th amino acid, from an N-terminus of the peptide sequence, form a ring with each other.

8. The method of claim 2, wherein a formula weight of the ethylene glycol repeating unit in L is in a range of 1 kDa to 100 kDa.

9. The method of claim 2, wherein F is an IgG Fc region.

10. The method of claim 1, wherein the lupus-associated disease is characterized by the appearance of symptoms in any one or more organs among the lugs, heart, muscles, and joints.

11. The method of claim 1, wherein the lupus-associated disease is systemic lupus erythematosus (SLE), discoid lupus erythematosus (DLE), drug-induced lupus, neonatal lupus, lupus nephritis, butterfly rash, or pernio-like rash.

12. The method of claim 1, wherein the pharmaceutical composition reduces skin lesions.

13. The method of claim 2, wherein the peptide is amidated at a C-terminus thereof.

14. The method of claim 2, wherein the peptide comprises an amino acid sequence selected from the group consisting of SEQ ID NOs: 21, 22, 42, 43, 50, 64, 66, 67, 70, 71, 76, 77, 96, 97 and 100.

15. The method of claim 14, wherein the peptide comprises an amino acid sequence selected from the group consisting of SEQ ID NOs: 21, 22, 42, 43, 50, 66, 67, 77, 96, 97, and 100.

16. The method of claim 15, wherein the peptide comprises an amino acid sequence selected from the group consisting of SEQ ID NOs: 21, 22, 42, 43, 50, 77, and 96.

17. The method of claim 2, wherein a 16th amino acid and a 20th amino acid, from an N-terminus of the peptide sequence, form a ring with each other.

18. The method of claim 2, wherein a formula weight of the ethylene glycol repeating unit in L is in a range of 1 kDa to 100 kDa; or wherein Fis an IgG Fc region.

19. The method of claim 2, wherein the lupus-associated disease is characterized by the appearance of symptoms in any one or more organs among the lugs, heart, muscles, and joints; or wherein the lupus-associated disease is systemic lupus erythematosus (SLE), discoid lupus erythematosus (DLE), drug-induced lupus, neonatal lupus, lupus nephritis, butterfly rash, or pernio-like rash.

20. The method of claim 1, wherein the administration of the pharmaceutical composition to the subject reduces skin lesions.

* * * * *